United States Patent [19]
Garfinkel et al.

[11] Patent Number: 6,008,193
[45] Date of Patent: *Dec. 28, 1999

[54] METHODS OF USING HUMAN VON WILLEBRAND FACTOR GPIB BINDING DOMAIN POLYPEPTIDES

[75] Inventors: Leonard Garfinkel, Rehovot; Tamar Richter, Nes Ziona, both of Israel

[73] Assignee: Bio-Technology General Corp., Iselin, N.J.

[ * ] Notice: This patent is subject to a terminal disclaimer.

[21] Appl. No.: 08/463,682

[22] Filed: Jun. 5, 1995

Related U.S. Application Data

[62] Division of application No. 08/347,594, Nov. 30, 1994, and a continuation of application No. 08/080,690, Jun. 22, 1993, abandoned, which is a continuation of application No. 07/753,815, Sep. 3, 1991, abandoned, which is a continuation-in-part of application No. PCT/US91/01416, Mar. 1, 1991, which is a continuation-in-part of application No. 07/487,767, Mar. 2, 1990, abandoned.

[51] Int. Cl.[6] .................................................. A61K 38/00
[52] U.S. Cl. ................................. 514/12; 514/2
[58] Field of Search ............................ 514/2, 12

[56] References Cited

U.S. PATENT DOCUMENTS

| | | | |
|---|---|---|---|
| 4,620,948 | 11/1986 | Builder et al. | 530/419 |
| 4,666,884 | 5/1987 | Hawiger et al. | 514/13 |
| 5,200,510 | 4/1993 | Kumar et al. | 530/383 |
| 5,238,919 | 8/1993 | Zimmerman et al. | 514/8 |
| 5,321,127 | 6/1994 | Handin | 530/383 |
| 5,340,727 | 8/1994 | Ruggeri et al. | 435/69.6 |
| 5,344,783 | 9/1994 | Scarborough et al. | 436/501 |

FOREIGN PATENT DOCUMENTS

| | | |
|---|---|---|
| 0160457 | 11/1985 | European Pat. Off. . |
| 169562 | 1/1986 | European Pat. Off. . |
| 197592 | 10/1986 | European Pat. Off. . |
| 8606096 | 10/1986 | European Pat. Off. . |
| 8606745 | 11/1986 | European Pat. Off. . |
| 0 255 206 | 2/1988 | European Pat. Off. . |
| 255206 | 2/1988 | European Pat. Off. . |
| 294025 | 12/1988 | European Pat. Off. . |
| 317278 | 5/1989 | European Pat. Off. . |
| 319315 | 6/1989 | European Pat. Off. . |
| 9109614 | 7/1991 | European Pat. Off. . |

OTHER PUBLICATIONS

Pietu et al. "Production in *Escherichia coli* of a Biologically Active Subfragment of von Willebrand Factor Corresponding to the Platelet Clycoprotein Ib, Collagen And Heparin Binding Domains", Biochemical and Biophysical Research Communications, vol. 1, Nov. 15, 1989.

Andrews et al. "Cross–Linking of a Monomeric 39/34–kDa Dispase Fragment of von Willebrand Factor (Leu–480/Val–48—Gly–718) to the N–Terminal Region of the alpha–Chain of Membrane Glycoprotein Ib on Intact Platelets with Bis(sulfosuccinimidyl) Suberate", 1989.

Kitigawa et al. "Involvement of Platelet Membrane Glycoprotein Ib and Glycoprotein IIb/IIIa Complex in Thrombin–Dependent and –Independent Platelet Aggregations Induced by Tumor Cells", Cancer Research, vol. 49, pp. 537–541, Feb. 1, 1989.

(List continued on next page.)

*Primary Examiner*—Ardin H. Marschel
*Attorney, Agent, or Firm*—John P. White; Cooper & Dunham LLP

[57] ABSTRACT

The subject invention provides non-glycosylated, biologically active polypeptides which comprise the vWF (von Willebrand Factor) GP1b binding domain. These polypeptides may be used to inhibit platelet adhesion and aggregation in the treatment of subjects with conditions such as cerebrovascular disorders and cardiovascular disorders. This invention also provides expression plasmids encoding these polypeptides as well as methods of producing by transforming a bacterial cell and recovering such polypeptides. In addition, the subject invention provides methods of treating and preventing cerebrovascular, cardiovascular and other disorders using these polypeptides to inhibit platelet aggregation.

4 Claims, 32 Drawing Sheets

```
  1 Met Leu His Asp Phe Tyr Cys Ser Arg Leu Leu Asp Leu Val Phe Leu    16
  1 ATG TTG CAC GAT TTC TAC TGC AGC AGG CTA CTG GAC CTG GTC TTC CTG    48

17 Leu Asp Gly Ser Ser Arg Leu Ser Gln Ala Glu Phe Glu Val Leu Lys    32
 49 CTG GAT GGC TCC TCC AGG CTG TCC GAG GCT GAG TTT GAA GTG CTG AAG    96

33 Ala Phe Val Val Asp Met Met Glu Arg Leu Arg Ile Ser Gln Lys Trp    48
 97 GCC TTT GTG GTG GAC ATG ATG GAG CGG CTG CGC ATC TCC CAG AAG TGG   144

49 Val Arg Val Ala Val Val Glu Tyr His Asp Gly Ser His Ala Tyr Ile    64
145 GTC CGC GTG GCC GTG GTG GAG TAC CAC GAC GGC TCC CAC GCC TAC ATC   192

65 Gly Leu Lys Asp Arg Lys Arg Pro Ser Glu Leu Arg Arg Ile Ala Ser    80
193 GGG CTC AAG GAC CGG AAG CGA CCA TCA GAG CTG CGG CGC ATT GCC AGC   240

81 Gln Val Lys Tyr Ala Gly Ser Gln Val Ala Ser Thr Ser Glu Val Leu    96
241 CAG GTG AAG TAT GCG GGC AGC CAG GTG GCC TCC ACC AGC GAG GTC TTG   288

97 Lys Tyr Thr Leu Phe Gln Ile Phe Ser Lys Ile Asp Arg Pro Glu Ala   112
289 AAA TAC ACA CTG TTC CAA ATC TTC AGC AAG ATC GAC CGC CCT GAA GCC   336

113 Ser Arg Ile Ala Leu Leu Leu Met Ala Ser Gln Glu Pro Gln Arg Met   128
337 TCC CGC ATC GCC CTG CTC CTG ATG GCC AGC CAG GAG CCC CAA CGG ATG   384

129 Ser Arg Asn Phe Val Arg Tyr Val Gln Gly Leu Lys Lys Lys Lys Val   144
385 TCC CGG AAC TTT GTC CGC TAC GTC CAG GGC CTG AAG AAG AAG AAG GTC   432

145 Ile Val Ile Pro Val Gly Ile Gly Pro His Ala Asn Leu Lys Gln Ile   160
433 ATT GTG ATC CCG GTG GGC ATT GGG CCC CAT GCC AAC CTC AAG CAG ATC   480

161 Arg Leu Ile Glu Lys Gln Ala Pro Glu Asn Lys Ala Phe Val Leu Ser   176
481 CGC CTC ATC GAG AAG CAG GCC CCT GAG AAC AAG GCC TTC GTG CTG AGC   528

177 Ser Val Asp Glu Leu Glu Gln Gln Arg Asp Glu Ile Val Ser Tyr Leu   192
529 AGT GTG GAT GAG CTG GAG CAG CAA AGG GAC GAG ATC GTT AGC TAC CTC   576

193 Cys Asp Leu Ala Pro Glu Ala Pro Pro Pro Thr Leu Pro Pro Asp Met   208
577 TGT GAC CTT GCC CCT GAA GCC CCT CCT CCT ACT CTG CCC CCC GAC ATG   624

209 Ala Gln Val Thr Val Gly Pro Gly Leu Leu Gly Val Ser Thr Leu Gly   224
625 GCA CAA GTC ACT GTG GGC CCG GGA CTC TTG GGG GTT TCG ACC CTG GGG   672

225 Pro Lys ***
673 CCC AAG TAA
```

OTHER PUBLICATIONS

Karpatkin et al. "Role of Adhesive Proteins in Platelet Tumor Inateraction In Vitro and Metastasis Formation in Vivo", Journal of Clinical Investigation, vol. 81, No. 4, pp. 1012–1019, 1988.

McBride et al. "Restenosis After Successful Coronary Angioplasty", The New England Journal of Medicine, vol. 318, No. 26, pp. 1734–1737, Jun. 30, 1988.

Bellinger et al. "Prevention of Occlusive Coronary Artery Thrombosis by a Murine Monoclonal Antibody to Porcine von Willebrand Factor", Proceedings of the National Academy of Sciences USA, vol. 84, pp. 8100–8104, Nov. 1988.

Sadler, et al., PNAS USA 82: 6394–6398 (Oct. 1985).

Girma, et al., Blood, 67: 1356–1366, (May 1986).

Houdijk, et al. "Thrombosis and Haemostasis", 56:(3): 391–396 (Sep. 1986).

Mohri, et al., J. Biological Chemistry, 264 (29): 17361–17367, (Oct. 1989).

Sixma, et al., J. Clinical Investigations 74: 736–744, (Sep. 1984).

Pietu, et al., Biochem. Biophys. Res. Comm. 164: 1339–1347 (Nov. 1989).

Fujimura, et al., J. Biol. Chem. 261: 381–385 (Jan. 1986).

Mohri, et al., J. Biol. Chem. 263: 17901–17904 (Dec. 1988).

Sugimoto, et al., Abstract No. 2371 in Supplement to Circulation, 82: p. III–597 (Oct. 1990).

Andrews, et al., Biochemistry, 28: 8326–8336, (1989).

Sadler et al., Abstract No. 3950 in Federation Proceedings, vol. 44. No. 4, p. 1069 (Mar. 1985).

Lynch et al., Cell, vol. 41, pp. 49–56 (May 1985).

Ginsburg et al., Science, vol. 228, pp. 1401–1406 (Jun. 1985).

Verweij et al., Nucleic Acids Research, vol. 13, No. 13, pp. 4699–4717 (Jul. 1985).

Prior et al., Bio/Technology, vol. 10, pp. 66–73 (Jan. 1992).

Fujimura et al., Abstract No. 1222 in Blood, vol. 66, p. 334a (Nov. 1985).

Gralnick et al., Proc. Nalt. Acad. Sci., vol. 89, pp. 7880–7884 (1992).

Wick et al., J. Clin. Invest., vol. 80, pp. 905–910 (1987).

Peterson et al., Blood, vol. 69, pp. 625–628 (1987).

Yammamoto et al., Thrumbosis Res., vol. 39, pp. 751–759 (1985).

Harmon et al., Bio Chemistry, vol. 27, pp. 2151–2157 (1988).

Pareti et al., J. Biol. Chem. 261(32):15310–15315 (1986).

Fujimura et al., J. Biol. Chem. 262(4):1734–1739 (1987).

Grossi et al., FASEB J. 2(8):2385–2395 (1988).

Mohri et al., CA114:182561m (1990).

Mancuso et al., J. Biol. Chem. 264(33:):19514–19527 (1989).

Carruthers et al., Biochemistry 28:8337–8346 (1989).

Fuster et al., Circulation Res. 51:587–593 (1982).

FIG. 2
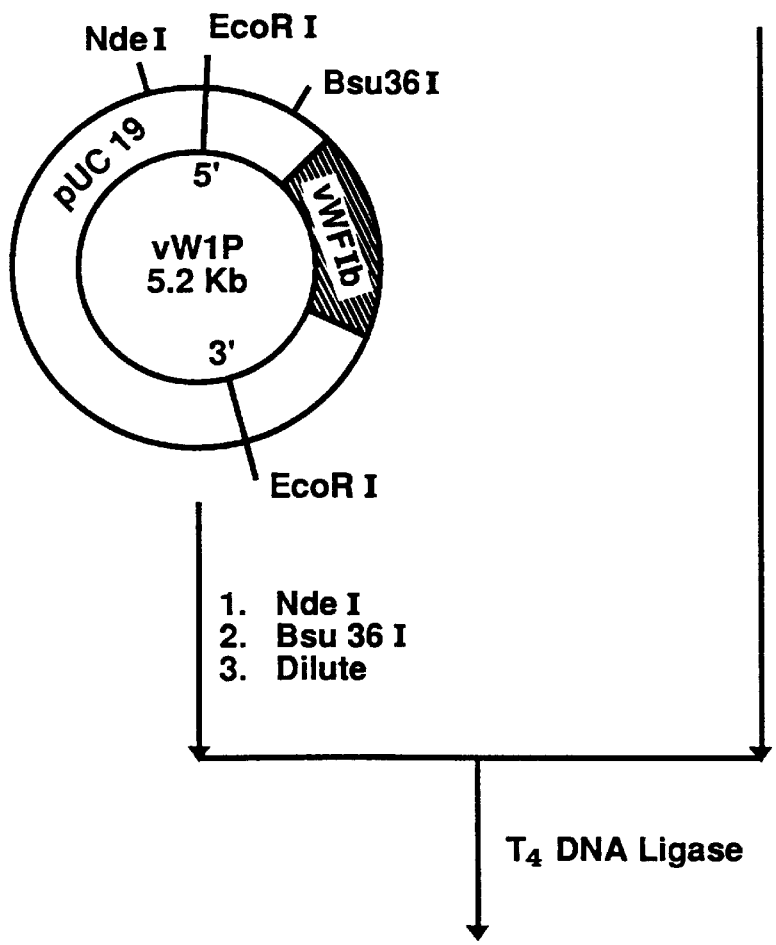
SYNTHETIC OLIGOMER
5' - TATGAGGTGGCTGGCCGGCGTTTTGCC - 3'
3' -   ACTCCACCGACCGGCCGCAAAACGGAGT - 5'
          └─NdeI─┘                    └─Bsu 36 I─┘
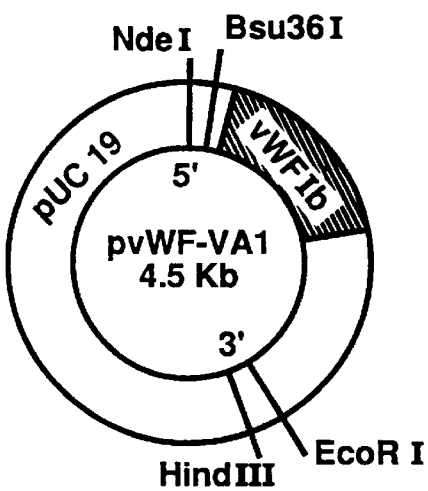

SYNTHETIC LINKER

5'-CCGGGGCTCTTGGGGGTTTCGACCCTGGGGCCCAAGTAAGATATCA-3'
3'-CCGAGAACCCCCAAAGCTGGGACCCCGGGTTCATTCTATAGTTCGA-5'

SYNTHETIC LINKER

5'-CCGGGGCTCTTGGGGTTTCGACCCTGGGGCCCAAGT<u>AAG</u>ATATCA-3'
3'-CCGAGAACCCCAAAGCTGGGACCCCGGGTTCA<u>TTC</u>TATAGTTCGA-5'

SYNTHETIC LINKER

5' - TATGTTGCACGATTTCTACTGCAGCAGGCTACTGGACC - 3'
3' - ACAACGTGCTAAAGATGACGTCGTCCGATGACCTGGA - 5'

NdeI                                Tth 111 I

FIG. 9
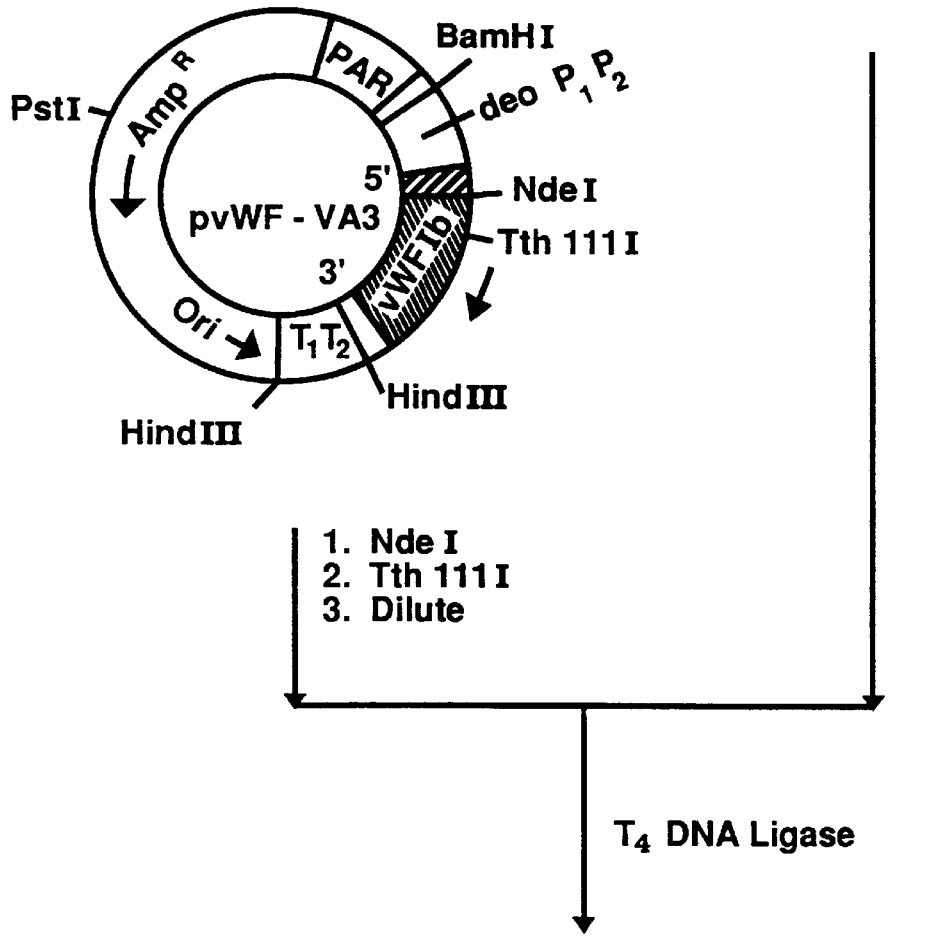
SYNTHETIC LINKERS
```
5' - TATGCTGGACC - 3'
3' -  ACGACCTGGA - 5'
         └──┘ └──┘
         NdeI  Tth 111 I
```
1. NdeI
2. Tth 111 I
3. Dilute
T₄ DNA Ligase
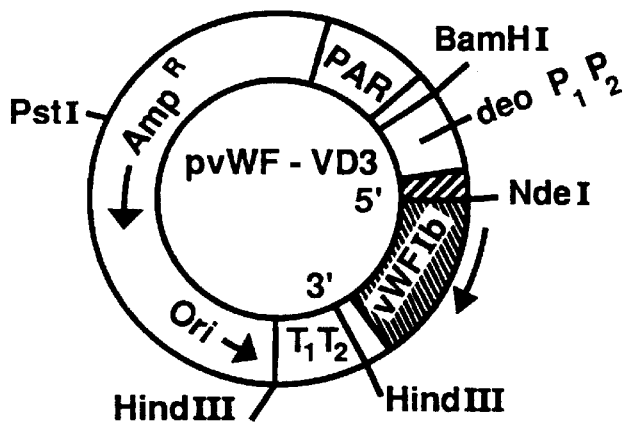

FIG. 12A

```
  1   Ser Leu Ser Cys Arg Pro Pro Met Val Lys Leu Val Cys Pro Ala Asp    16
2519  AGC CTA TCC TGT CGG CCC CCC ATG GTC AAG CTG GTG TGT CCC GCT GAC  2566

17   Asn Leu Arg Ala Glu Gly Leu Glu Cys Thr Lys Thr Cys Gln Asn Tyr    32
2567  AAC CTG CGG GCT GAA GGG CTC GAG TGT ACC AAA ACG TGC CAG AAC TAT  2614

33   Asp Leu Glu Cys Met Ser Met Gly Cys Val Ser Gly Cys Leu Cys Pro    48
2615  GAC CTG GAG TGC ATG AGC ATG GGC TGT GTC TCT GGC TGC CTC TGC CCC  2662

49   Pro Gly Met Val Arg His Glu Asn Arg Cys Val Ala Leu Glu Arg Cys    64
2663  CCG GGC ATG GTC CGG CAT GAG AAC AGA TGT GTG GCC CTG GAA AGG TGT  2710

65   Pro Cys Phe His Gln Gly Lys Glu Tyr Ala Pro Gly Glu Thr Val Lys    80
2711  CCC TGC TTC CAT CAG GGC AAG GAG TAT GCC CCT GGA GAA ACA GTG AAG  2758

81   Ile Gly Cys Asn Thr Cys Val Cys Arg Asp Arg Lys Trp Asn Cys Thr    96
2759  ATT GGC TGC AAC ACT TGT GTC TGT CGG GAC CGG AAG TGG AAC TGC ACA  2806

97   Asp His Val Cys Asp Ala Thr Cys Ser Thr Ile Gly Met Ala His Tyr   112
2807  GAC CAT GTG TGT GAT GCC ACG TGC TCC ACG ATC GGC ATG GCC CAC TAC  2854

113   Leu Thr Phe Asp Gly Leu Lys Tyr Leu Phe Pro Gly Glu Cys Gln Tyr   128
2855  CTC ACC TTC GAC GGG CTC AAA TAC CTG TTC CCC GGG GAG TGC CAG TAC  2902

129   Val Leu Val Gln Asp Tyr Cys Gly Ser Asn Pro Gly Thr Phe Arg Ile   144
2903  GTT CTG GTG CAG GAT TAC TGC GGC AGT AAC CCT GGG ACC TTT CGG ATC  2950

145   Leu Val Gly Asn Lys Gly Cys Ser His Pro Ser Val Lys Cys Lys Lys   160
2951  CTA GTG GGG AAT AAG GGA TGC AGC CAC CCC TCA GTG AAA TGC AAG AAA  2998

161   Arg Val Thr Ile Leu Val Glu Gly Gly Glu Ile Glu Leu Phe Asp Gly   176
2999  CGG GTC ACC ATC CTG GTG GAG GGA GGA GAG ATT GAG CTG TTT GAC GGG  3046

177   Glu Val Asn Val Lys Arg Pro Met Lys Asp Glu Thr His Phe Glu Val   192
3047  GAG GTG AAT GTG AAG AGG CCC ATG AAG GAT GAG ACT CAC TTT GAG GTG  3094

193   Val Glu Ser Gly Arg Tyr Ile Ile Leu Leu Leu Gly Lys Ala Leu Ser   208
3095  GTG GAG TCT GGC CGG TAC ATC ATT CTG CTG CTG GGC AAA GCC CTC TCC  3142

209   Val Val Trp Asp Arg His Leu Ser Ile Ser Val Val Leu Lys Gln Thr   224
3143  GTG GTC TGG GAC CGC CAC CTG AGC ATC TCC GTG GTC CTG AAG CAG ACA  3190

225   Tyr Gln Glu Lys Val Cys Gly Leu Cys Gly Asn Phe Asp Gly Ile Gln   240
3191  TAC CAG GAG AAA GTG TGT GGC CTG TGT GGG AAT TTT GAT GGC ATC CAG  3238

241   Asn Asn Asp Leu Thr Ser Ser Asn Leu Gln Val Glu Glu Asp Pro Val   256
3239  AAC AAT GAC CTC ACC AGC AGC AAC CTC CAA GTG GAG GAG GAC CCT GTG  3286
```

FIG. 12B

| | | | | | | | | | | | | | | | | | |
|---|---|---|---|---|---|---|---|---|---|---|---|---|---|---|---|---|---|
| 257 | Asp | Phe | Gly | Lys | Ser | Trp | Glu | Val | Ser | Ser | Gln | Cys | Ala | Asp | Thr | Arg | 272 |
| 3287 | GAC | TTT | GGG | AAG | TCC | TGG | GAA | GTG | AGC | TCG | CAG | TGT | GCT | GAC | ACC | AGA | 3334 |
| 273 | Lys | Val | Pro | Leu | Asp | Ser | Ser | Pro | Ala | Thr | Cys | His | Asn | Asn | Ile | Met | 288 |
| 3335 | AAA | GTG | CCT | CTG | GAC | TCA | TCC | CCT | GCC | ACC | TGC | CAT | AAC | AAC | ATC | ATG | 3382 |
| 289 | Lys | Gln | Thr | Met | Val | Asp | Ser | Ser | Cys | Arg | Ile | Leu | Thr | Ser | Asp | Val | 304 |
| 3383 | AAG | CAG | ACG | ATG | GTG | GAT | TCC | TCC | TGT | AGA | ATC | CTT | ACC | AGT | GAC | GTC | 3430 |
| 305 | Phe | Gln | Asp | Cys | Asn | Lys | Leu | Val | Asp | Pro | Glu | Pro | Tyr | Leu | Asp | Val | 320 |
| 3431 | TTC | CAG | GAC | TGC | AAC | AAG | CTG | GTG | GAC | CCC | GAG | CCA | TAT | CTG | GAT | GTC | 3478 |
| 321 | Cys | Ile | Tyr | Asp | Thr | Cys | Ser | Cys | Glu | Ser | Ile | Gly | Asp | Cys | Ala | Cys | 336 |
| 3479 | TGC | ATT | TAC | GAC | ACC | TGC | TCC | TGT | GAG | TCC | ATT | GGG | GAC | TGC | GCC | TGC | 3526 |
| 337 | Phe | Cys | Asp | Thr | Ile | Ala | Ala | Tyr | Ala | His | Val | Cys | Ala | Gln | His | Gly | 352 |
| 3527 | TTC | TGC | GAC | ACC | ATT | GCT | GCC | TAT | GCC | CAC | GTG | TGT | GCC | CAG | CAT | GGC | 3574 |
| 353 | Lys | Val | Val | Thr | Trp | Arg | Thr | Ala | Thr | Leu | Cys | Pro | Gln | Ser | Cys | Glu | 368 |
| 3575 | AAG | GTG | GTG | ACC | TGG | AGG | ACG | GCC | ACA | TTG | TGC | CCC | CAG | AGC | TGC | GAG | 3622 |
| 369 | Glu | Arg | Asn | Leu | Arg | Glu | Asn | Gly | Tyr | Glu | Cys | Glu | Trp | Arg | Tyr | Asn | 384 |
| 3623 | GAG | AGG | AAT | CTC | CGG | GAG | AAC | GGG | TAT | GAG | TGT | GAG | TGG | CGC | TAT | AAC | 3670 |
| 385 | Ser | Cys | Ala | Pro | Ala | Cys | Gln | Val | Thr | Cys | Gln | His | Pro | Glu | Pro | Leu | 400 |
| 3671 | AGC | TGT | GCA | CCT | GCC | TGT | CAA | GTC | ACG | TGT | CAG | CAC | CCT | GAG | CCA | CTG | 3718 |
| 401 | Ala | Cys | Pro | Val | Gln | Cys | Val | Glu | Gly | Cys | His | Ala | His | Cys | Pro | Pro | 416 |
| 3719 | GCC | TGC | CCT | GTG | CAG | TGT | GTG | GAG | GGC | TGC | CAT | GCC | CAT | TGC | CCT | CCA | 3766 |
| 417 | Gly | Lys | Ile | Leu | Asp | Glu | Leu | Leu | Gln | Thr | Cys | Val | Asp | Pro | Glu | Asp | 432 |
| 3767 | GGC | AAA | ATC | CTG | GAT | GAG | CTT | TTG | CAG | ACC | TGC | GTT | GAC | CCT | GAA | GAC | 3814 |
| 433 | Cys | Pro | Val | Cys | Glu | Val | Ala | Gly | Arg | Arg | Phe | Ala | Ser | Gly | Lys | Lys | 448 |
| 3815 | TGT | CCA | GTG | TGT | GAG | GTG | GCT | GGC | CGG | CGT | TTT | GCC | TCA | GGA | AAG | AAA | 3862 |
| 449 | Val | Thr | Leu | Asn | Pro | Ser | Asp | Pro | Glu | His | Cys | Gln | Ile | Cys | His | Cys | 464 |
| 3863 | GTC | ACC | TTG | AAT | CCC | AGT | GAC | CCT | GAG | CAC | TGC | CAG | ATT | TGC | CAC | TGT | 3910 |
| 465 | Asp | Val | Val | Asn | Leu | Thr | Cys | Glu | Ala | Cys | Gln | Glu | Pro | Gly | Gly | Leu | 480 |
| 3911 | GAT | GTT | GTC | AAC | CTC | ACC | TGT | GAA | GCC | TGC | CAG | GAG | CCG | GGA | GGC | CTG | 3958 |
| 481 | Val | Val | Pro | Pro | Thr | Asp | Ala | Pro | Val | Ser | Pro | Thr | Thr | Leu | Tyr | Val | 496 |
| 3959 | GTG | GTG | CCT | CCC | ACA | GAT | GCC | CCG | GTG | AGC | CCC | ACC | ACT | CTG | TAT | GTG | 4006 |
| 497 | Glu | Asp | Ile | Ser | Glu | Pro | Pro | Leu | His | Asp | Phe | Tyr | Cys | Ser | Arg | Leu | 512 |
| 4007 | GAG | GAC | ATC | TCG | GAA | CCG | CCG | TTG | CAC | GAT | TTC | TAC | TGC | AGC | AGG | CTA | 4054 |
| 513 | Leu | Asp | Leu | Val | Phe | Leu | Leu | Asp | Gly | Ser | Ser | Arg | Leu | Ser | Glu | Ala | 528 |
| 4055 | CTG | GAC | CTG | GTC | TTC | CTG | CTG | GAT | GGC | TCC | TCC | AGG | CTG | TCC | GAG | GCT | 4102 |

FIG. 12C

```
529  Glu Phe Glu Val Leu Lys Ala Phe Val Val Asp Met Met Glu Arg Leu  544
4103 GAG TTT GAA GTG CTG AAG GCC TTT GTG GTG GAC ATG ATG GAG CGG CTG  4150

545  Arg Ile Ser Gln Lys Trp Val Arg Val Ala Val Val Glu Tyr His Asp  560
4151 CGC ATC TCC CAG AAG TGG GTC CGC GTG GCC GTG GTG GAG TAC CAC GAC  4198

561  Gly Ser His Ala Tyr Ile Gly Leu Lys Asp Arg Lys Arg Pro Ser Glu  576
4199 GGC TCC CAC GCC TAC ATC GGG CTC AAG GAC CGG AAG CGA CCA TCA GAG  4246

577  Leu Arg Arg Ile Ala Ser Gln Val Lys Tyr Ala Gly Ser Gln Val Ala  592
4247 CTG CGG CGC ATT GCC AGC CAG GTG AAG TAT GCG GGC AGC CAG GTG GCC  4294

593  Ser Thr Ser Glu Val Leu Lys Tyr Thr Leu Phe Gln Ile Phe Ser Lys  608
4295 TCC ACC AGC GAG GTC TTG AAA TAC ACA CTG TTC CAA ATC TTC AGC AAG  4342

609  Ile Asp Arg Pro Glu Ala Ser Arg Ile Ala Leu Leu Leu Met Ala Ser  624
4343 ATC GAC CGC CCT GAA GCC TCC CGC ATC GCC CTG CTC CTG ATG GCC AGC  4390

625  Gln Glu Pro Gln Arg Met Ser Arg Asn Phe Val Arg Tyr Val Gln Gly  640
4391 CAG GAG CCC CAA CGG ATG TCC CGG AAC TTT GTC CGC TAC GTC CAG GGC  4438

641  Leu Lys Lys Lys Lys Val Ile Val Ile Pro Val Gly Ile Gly Pro His  656
4439 CTG AAG AAG AAG AAG GTC ATT GTG ATC CCG GTG GGC ATT GGG CCC CAT  4486

657  Ala Asn Leu Lys Gln Ile Arg Leu Ile Glu Lys Gln Ala Pro Glu Asn  672
4487 GCC AAC CTC AAG CAG ATC CGC CTC ATC GAG AAG CAG GCC CCT GAG AAC  4534

673  Lys Ala Phe Val Leu Ser Ser Val Asp Glu Leu Glu Gln Gln Arg Asp  688
4535 AAG GCC TTC GTG CTG AGC AGT GTG GAT GAG CTG GAG CAG CAA AGG GAC  4582

689  Glu Ile Val Ser Tyr Leu Cys Asp Leu Ala Pro Glu Ala Pro Pro Pro  704
4583 GAG ATC GTT AGC TAC CTC TGT GAC CTT GCC CCT GAA GCC CCT CCT CCT  4630

705  Thr Leu Pro Pro Asp Met Ala Gln Val Thr Val Gly Pro Gly Leu Leu  720
4631 ACT CTG CCC CCC GAC ATG GCA CAA GTC ACT GTG GGC CCG GGG CTC TTG  4678

721  Gly Val Ser Thr Leu Gly Pro Lys Arg Asn Ser Met Val Leu Asp Val  736
4679 GGG GTT TCG ACC CTG GGG CCC AAG AGG AAC TCC ATG GTT CTG GAT GTG  4726

737  Ala Phe Val Leu Glu Gly Ser Asp Lys Ile Gly Glu Ala Asp Phe Asn  752
4727 GCG TTC GTC CTG GAA GGA TCG GAC AAA ATT GGT GAA GCC GAC TTC AAC  4774

753  Arg Ser Lys Glu Phe Met Glu Glu Val Ile Gln Arg Met Asp Val Gly  768
4775 AGG AGC AAG GAG TTC ATG GAG GAG GTG ATT CAG CGG ATG GAT GTG GGC  4822

769  Gln Asp Ser Ile His Val Thr Val Leu Gln Tyr Ser Tyr Met Val Thr  784
4823 CAG GAC AGC ATC CAC GTC ACG GTG CTG CAG TAC TCC TAC ATG GTG ACC  4870

785  Val Glu Tyr Pro Phe Ser Glu Ala Gln Ser Lys Gly Asp Ile Leu Gln  800
4871 GTG GAG TAC CCC TTC AGC GAG GCA CAG TCC AAA GGG GAC ATC CTG CAG  4918
```

FIG. 12D

```
 801  Arg Val Arg Glu Ile Arg Tyr Gln Gly Gly Asn Arg Thr Asn Thr Gly   816
4919  CGG GTG CGA GAG ATC CGC TAC CAG GGC GGC AAC AGG ACC AAC ACT GGG  4966

817  Leu Ala Leu Arg Tyr Leu Ser Asp His Ser Phe Leu Val Ser Gln Gly   832
4967  CTG GCC CTG CGG TAC CTC TCT GAC CAC AGC TTC TTG GTC AGC CAG GGT  5014

833  Asp Arg Glu Gln Ala Pro Asn Leu Val Tyr Met Val Thr Gly Asn Pro   848
5015  GAC CGG GAG CAG GCG CCC AAC CTG GTC TAC ATG GTC ACC GGA AAT CCT  5062

849  Ala Ser Asp Glu Ile Lys Arg Leu Pro Gly Asp Ile Gln Val Val Pro   864
5063  GCC TCT GAT GAG ATC AAG AGG CTG CCT GGA GAC ATC CAG GTG GTG CCC  5110

865  Ile Gly Val Gly Pro Asn Ala Asn Val Gln Glu Leu Glu Arg Ile Gly   880
5111  ATT GGA GTG GGC CCT AAT GCC AAC GTG CAG GAG CTG GAG AGG ATT GGC  5158

881  Trp Pro Asn Ala Pro Ile Leu Ile Gln Asp Phe Glu Thr Leu Pro Arg   896
5159  TGG CCC AAT GCC CCT ATC CTC ATC CAG GAC TTT GAG ACG CTC CCC CGA  5206

897  Glu Ala Pro Asp Leu Val Leu Gln Arg Cys Cys Ser Gly Glu Gly Leu   912
5207  GAG GCT CCT GAC CTG GTG CTG CAG AGG TGC TGC TCC GGA GAG GGG CTG  5254

913  Gln Ile Pro Thr Leu Ser Pro Ala Pro Asp Cys Ser Gln Pro Leu Asp   928
5255  CAG ATC CCC ACC CTC TCC CCA GCA CCT GAC TGC AGC CAG CCC CTG GAC  5302

929  Val Ile Leu Leu Leu Asp Gly Ser Ser Ser Phe Pro Ala Ser Tyr Phe   944
5303  GTG ATC CTT CTC CTG GAT GGC TCC TCC AGT TTC CCA GCT TCT TAT TTT  5350

945  Asp Glu Met Lys Ser Phe Ala Lys Ala Phe Ile Ser Lys Ala Asn Ile   960
5351  GAT GAA ATG AAG AGT TTC GCC AAG GCT TTC ATT TCA AAA GCC AAT ATA  5398

961  Gly Pro Arg Leu Thr Gln Val Ser Val Leu Gln Tyr Gly Ser Ile Thr   976
5399  GGG CCT CGT CTC ACT CAG GTG TCA GTG CTG CAG TAT GGA AGC ATC ACC  5446

977  Thr Ile Asp Val Pro Trp Asn Val Val Pro Glu Lys Ala His Leu Leu   992
5447  ACC ATT GAC GTG CCA TGG AAC GTG GTC CCG GAG AAA GCC CAT TTG CTG  5494

993  Ser Leu Val Asp Val Met Gln Arg Glu Gly Gly Pro Ser Gln Ile Gly  1008
5495  AGC CTT GTG GAC GTC ATG CAG CGG GAG GGA GGC CCC AGC CAA ATC GGG  5542

1009  Asp Ala Leu Gly Phe Ala Val Arg Tyr Leu Thr Ser Glu Met His Gly  1024
5543  GAT GCC TTG GGC TTT GCT GTG CGA TAC TTG ACT TCA GAA ATG CAT GGT  5590

1025  Ala Arg Pro Gly Ala Ser Lys Ala Val Val Ile Leu Val Thr Asp Val  1040
5591  GCC AGG CCG GGA GCC TCA AAG GCG GTG GTC ATC CTG GTC ACG GAC GTC  5638

1041  Ser Val Asp Ser Val Asp Ala Ala Asp Ala Ala Arg Ser Asn Arg  1056
5639  TCT GTG GAT TCA GTG GAT GCA GCA GCT GAT GCC GCC AGG TCC AAC AGA  5686

1057  Val Thr Val Phe Pro Ile Gly Ile Gly Asp Arg Tyr Asp Ala Ala Gln  1072
5687  GTG ACA GTG TTC CCT ATT GGA ATT GGA GAT CGC TAC GAT GCA GCC CAG  5734
```

FIG. 12E

```
1073  Leu Arg Ile Leu Ala Gly Pro Ala Gly Asp Ser Asn Val Val Lys Leu  1088
5735  CTA CGG ATC TTG GCA GGC CCA GCA GGC GAC TCC AAC GTG GTG AAG CTC  5782

1089  Gln Arg Ile Glu Asp Leu Pro Thr Met Val Thr Leu Gly Asn Ser Phe  1104
5783  CAG CGA ATC GAA GAC CTC CCT ACC ATG GTC ACC TTG GGC AAT TCC TTC  5830

1105  Leu His Lys Leu Cys Ser Gly Phe Val Arg Ile Cys Met Asp Glu Asp  1120
5831  CTC CAC AAA CTG TGC TCT GGA TTT GTT AGG ATT TGC ATG GAT GAG GAT  5878

1121  Gly Asn Glu Lys Arg Pro Gly Asp Val Trp Thr Leu Pro Asp Gln Cys  1136
5879  GGG AAT GAG AAG AGG CCC GGG GAC GTC TGG ACC TTG CCA GAC CAG TGC  5926

1137  His Thr Val Thr Cys Gln Pro Asp Gly Gln Thr Leu Leu Lys Ser His  1152
5927  CAC ACC GTG ACT TGC CAG CCA GAT GGC CAG ACC TTG CTG AAG AGT CAT  5974

1153  Arg Val Asn Cys Asp Arg Gly Leu Arg Pro Ser Cys Pro Asn Ser Gln  1168
5975  CGG GTC AAC TGT GAC CGG GGG CTG AGG CCT TCG TGC CCT AAC AGC CAG  6022

1169  Ser Pro Val Lys Val Glu Glu Thr Cys Gly Cys Arg Trp Thr Cys Pro  1184
6023  TCC CCT GTT AAA GTG GAA GAG ACC TGT GGC TGC CGC TGG ACC TGC CCC  6070

1185  Cys Val Cys Thr Gly Ser Ser Thr Arg His Ile Val Thr Phe Asp Gly  1200
6071  TGC GTG TGC ACA GGC AGC TCC ACT CGG CAC ATC GTG ACC TTT GAT GGG  6118

1201  Gln Asn Phe Lys Leu Thr Gly Ser Cys Ser Tyr Val Leu Phe Gln Asn  1216
6119  CAG AAT TTC AAG CTG ACT GGC AGC TGT TCT TAT GTC CTA TTT CAA AAC  6166

1217  Lys Glu Gln Asp Leu Glu Val Ile Leu His Asn Gly Ala Cys Ser Pro  1232
6167  AAG GAG CAG GAC CTG GAG GTG ATT CTC CAT AAT GGT GCC TGC AGC CCT  6214

1233  Gly Ala Arg Gln Gly Cys Met Lys Ser Ile Glu Val Lys His Ser Ala  1248
6215  GGA GCA AGG CAG GGC TGC ATG AAA TCC ATC GAG GTG AAG CAC AGT GCC  6262

1249  Leu Ser Val Glu Leu His Ser Asp Met Glu Val Thr Val Asn Gly Arg  1264
6263  CTC TCC GTC GAG CTG CAC AGT GAC ATG GAG GTG ACG GTG AAT GGG AGA  6310

1265  Leu Val Ser Val Pro Tyr Val Gly Gly Asn Met Glu Val Asn Val Tyr  1280
6311  CTG GTC TCT GTT CCT TAC GTG GGT GGG AAC ATG GAA GTC AAC GTT TAT  6358

1281  Gly Ala Ile Met His Glu Val Arg Phe Asn His Leu Gly His Ile Phe  1296
6359  GGT GCC ATC ATG CAT GAG GTC AGA TTC AAT CAC CTT GGT CAC ATC TTC  6406

1297  Thr Phe Thr Pro Gln Asn Asn Glu Phe Gln Leu Gln Leu Ser Pro Lys  1312
6407  ACA TTC ACT CCA CAA AAC AAT GAG TTC CAA CTG CAG CTC AGC CCC AAG  6454

1313  Thr Phe Ala Ser Lys Thr Tyr Gly Leu Cys Gly Ile Cys Asp Glu Asn  1328
6455  ACT TTT GCT TCA AAG ACG TAT GGT CTG TGT GGG ATC TGT GAT GAG AAC  6502

1329  Gly Ala Asn Asp Phe Met Leu Arg Asp Gly Thr Val Thr Thr Asp Trp  1344
6503  GGA GCC AAT GAC TTC ATG CTG AGG GAT GGC ACA GTC ACC ACA GAC TGG  6550
```

FIG. 12F

```
1345  Lys Thr Leu Val Gln Glu Trp Thr Val Gln Arg Pro Gly Gln Thr Cys  1360
6551  AAA ACA CTT GTT CAG GAA TGG ACT GTG CAG CGG CCA GGA CAG ACG TGC  6598

1361  Gln Pro Ile Leu Glu Glu Gln Cys Leu Val Pro Asp Ser Ser His Cys  1376
6599  CAG CCC ATC CTG GAG GAG CAG TGT CTT GTC CCC GAC AGC TCC CAC TGC  6646

1377  Gln Val Leu Leu Leu Pro Leu Phe Ala Glu Cys His Lys Val Leu Ala  1392
6647  CAG GTC CTC CTC TTA CCA CTG TTT GCT GAA TGC CAC AAG GTC CTG GCT  6694

1393  Pro Ala Thr Phe Tyr Ala Ile Cys Gln Gln Asp Ser Ser His Gln Glu  1408
6695  CCA GCC ACA TTC TAT GCC ATC TGC CAG CAG GAC AGT TCG CAC CAG GAG  6742

1409  Gln Val Cys Glu Val Ile Ala Ser Tyr Ala His Leu Cys Arg Thr Asn  1424
6743  CAA GTG TGT GAG GTG ATC GCC TCT TAT GCC CAC CTC TGT CGG ACC AAC  6790

1425  Gly Val Cys Val Asp Trp Arg Thr Pro Asp Phe Cys Ala Met Ser Cys  1440
6791  GGG GTC TGC GTT GAC TGG AGG ACA CCT GAT TTC TGT GCT ATG TCA TGC  6838

1441  Pro Pro Ser Leu Val Tyr Asn His Cys Glu His Gly Cys Pro Arg His  1456
6839  CCA CCA TCT CTG GTC TAC AAC CAC TGT GAG CAT GGC TGT CCC CGG CAC  6886

1457  Cys Asp Gly Asn Val Ser Ser Cys Gly Asp His Pro Ser Glu Gly Cys  1472
6887  TGT GAT GGC AAC GTG AGC TCC TGT GGG GAC CAT CCC TCC GAA GGC TGT  6934

1473  Phe Cys Pro Pro Asp Lys Val Met Leu Glu Gly Ser Cys Val Pro Glu  1488
6935  TTC TGC CCT CCA GAT AAA GTC ATG TTG GAA GGC AGC TGT GTC CCT GAA  6982

1489  Glu Ala Cys Thr Gln Cys Ile Gly Glu Asp Gly Val Gln His Gln Phe  1504
6983  GAG GCC TGC ACT CAG TGC ATT GGT GAG GAT GGA GTC CAG CAC CAG TTC  7030

1505  Leu Glu Ala Trp Val Pro Asp His Gln Pro Cys Gln Ile Cys Thr Cys  1520
7031  CTG GAA GCC TGG GTC CCG GAC CAC CAG CCC TGT CAG ATC TGC ACA TGC  7078

1521  Leu Ser Gly Arg Lys Val Asn Cys Thr Thr Gln Pro Cys Pro Thr Ala  1536
7079  CTC AGC GGG CGG AAG GTC AAC TGC ACA ACG CAG CCC TGC CCC ACG GCC  7126

1537  Lys Ala Pro Thr Cys Gly Leu Cys Glu Val Ala Arg Leu Arg Gln Asn  1552
7127  AAA GCT CCC ACG TGT GGC CTG TGT GAA GTA GCC CGC CTC CGC CAG AAT  7174

1553  Ala Asp Gln Cys Cys Pro Glu Tyr Glu Cys Val Cys Asp Pro Val Ser  1568
7175  GCA GAC CAG TGC TGC CCC GAG TAT GAG TGT GTG TGT GAC CCA GTG AGC  7222

1569  Cys Asp Leu Pro Pro Val Pro His Cys Glu Arg Gly Leu Gln Pro Thr  1584
7223  TGT GAC CTG CCC CCA GTG CCT CAC TGT GAA CGT GGC CTC CAG CCC ACA  7270

1585  Leu Thr Asn Pro Gly Glu Cys Arg Pro Asn Phe Thr Cys Ala Cys Arg  1600
7271  CTG ACC AAC CCT GGC GAG TGC AGA CCC AAC TTC ACC TGC GCC TGC AGG  7318

1601  Lys Glu Glu Cys Lys Arg Val Ser Pro Pro Ser Cys Pro Pro His Arg  1616
7319  AAG GAG GAG TGC AAA AGA GTG TCC CCA CCC TCC TGC CCC CCG CAC CGT  7366
```

FIG. 12G

```
1617  Leu Pro Thr Leu Arg Lys Thr Gln Cys Cys Asp Glu Tyr Glu Cys Ala  1632
7367  TTG CCC ACC CTT CGG AAG ACC CAG TGC TGT GAT GAG TAT GAG TGT GCC  7414

1633  Cys Asn Cys Val Asn Ser Thr Val Ser Cys Pro Leu Gly Tyr Leu Ala  1648
7415  TGC AAC TGT GTC AAC TCC ACA GTG AGC TGT CCC CTT GGG TAC TTG GCC  7462

1649  Ser Thr Ala Thr Asn Asp Cys Gly Cys Thr Thr Thr Thr Cys Leu Pro  1664
7463  TCA ACC GCC ACC AAT GAC TGT GGC TGT ACC ACA ACC ACC TGC CTT CCC  7510

1665  Asp Lys Val Cys Val His Arg Ser Thr Ile Tyr Pro Val Gly Gln Phe  1680
7511  GAC AAG GTG TGT GTC CAC CGA AGC ACC ATC TAC CCT GTG GGC CAG TTC  7558

1681  Trp Glu Glu Gly Cys Asp Val Cys Thr Cys Thr Asp Met Glu Asp Ala  1696
7559  TGG GAG GAG GGC TGC GAT GTG TGC ACC TGC ACC GAC ATG GAG GAT GCC  7606

1697  Val Met Gly Leu Arg Val Ala Gln Cys Ser Gln Lys Pro Cys Glu Asp  1712
7607  GTG ATG GGC CTC CGC GTG GCC CAG TGC TCC CAG AAG CCC TGT GAG GAC  7654

1713  Ser Cys Arg Ser Gly Phe Thr Tyr Val Leu His Glu Gly Glu Cys Cys  1728
7655  AGC TGT CGG TCG GGC TTC ACT TAC GTT CTG CAT GAA GGC GAG TGC TGT  7702

1729  Gly Arg Cys Leu Pro Ser Ala Cys Glu Val Val Thr Gly Ser Pro Arg  1744
7703  GGA AGG TGC CTG CCA TCT GCC TGT GAG GTG GTG ACT GGC TCA CCG CGG  7750

1745  Gly Asp Ser Gln Ser Ser Trp Lys Ser Val Gly Ser Gln Trp Ala Ser  1760
7751  GGG GAC TCC CAG TCT TCC TGG AAG AGT GTC GGC TCC CAG TGG GCC TCC  7798

1761  Pro Glu Asn Pro Cys Leu Ile Asn Glu Cys Val Arg Val Lys Glu Glu  1776
7799  CCG GAG AAC CCC TGC CTC ATC AAT GAG TGT GTC CGA GTG AAG GAG GAG  7846

1777  Val Phe Ile Gln Gln Arg Asn Val Ser Cys Pro Gln Leu Glu Val Pro  1792
7847  GTC TTT ATA CAA CAA AGG AAC GTC TCC TGC CCC CAG CTG GAG GTC CCT  7894

1793  Val Cys Pro Ser Gly Phe Gln Leu Ser Cys Lys Thr Ser Ala Cys Cys  1808
7895  GTC TGC CCC TCG GGC TTT CAG CTG AGC TGT AAG ACC TCA GCG TGC TGC  7942

1809  Pro Ser Cys Arg Cys Glu Arg Met Glu Ala Cys Met Leu Asn Gly Thr  1824
7943  CCA AGC TGT CGC TGT GAG CGC ATG GAG GCC TGC ATG CTC AAT GGC ACT  7990

1825  Val Ile Gly Pro Gly Lys Thr Val Met Ile Asp Val Cys Thr Thr Cys  1840
7991  GTC ATT GGG CCC GGG AAG ACT GTG ATG ATC GAT GTG TGC ACG ACC TGC  8038

1841  Arg Cys Met Val Gln Val Gly Val Ile Ser Gly Phe Lys Leu Glu Cys  1856
8039  CGC TGC ATG GTG CAG GTG GGG GTC ATC TCT GGA TTC AAG CTG GAG TGC  8086

1857  Arg Lys Thr Thr Cys Asn Pro Cys Pro Leu Gly Tyr Lys Glu Glu Asn  1872
8087  AGG AAG ACC ACC TGC AAC CCC TGC CCC CTG GGT TAC AAG GAA GAA AAT  8134

1873  Asn Thr Gly Glu Cys Cys Gly Arg Cys Leu Pro Thr Ala Cys Thr Ile  1888
8135  AAC ACA GGT GAA TGT TGT GGG AGA TGT TTG CCT ACG GCT TGC ACC ATT  8182
```

FIG. 12H

```
1889  Gln Leu Arg Gly Gly Gln Ile Met Thr Leu Lys Arg Asp Glu Thr Leu  1904
8183  CAG CTA AGA GGA GGA CAG ATC ATG ACA CTG AAG CGT GAT GAG ACG CTC  8230

1905  Gln Asp Gly Cys Asp Thr His Phe Cys Lys Val Asn Glu Arg Gly Glu  1920
8231  CAG GAT GGC TGT GAT ACT CAC TTC TGC AAG GTC AAT GAG AGA GGA GAG  8278

1921  Tyr Phe Trp Glu Lys Arg Val Thr Gly Cys Pro Pro Phe Asp Glu His  1936
8279  TAC TTC TGG GAG AAG AGG GTC ACA GGC TGC CCA CCC TTT GAT GAA CAC  8326

1937  Lys Cys Leu Ala Glu Gly Gly Lys Ile Met Lys Ile Pro Gly Thr Cys  1952
8327  AAG TGT CTG GCT GAG GGA GGT AAA ATT ATG AAA ATT CCA GGC ACC TGC  8374

1953  Cys Asp Thr Cys Glu Glu Pro Glu Cys Asn Asp Ile Thr Ala Arg Leu  1968
8375  TGT GAC ACA TGT GAG GAG CCT GAG TGC AAC GAC ATC ACT GCC AGG CTG  8422

1969  Gln Tyr Val Lys Val Gly Ser Cys Lys Ser Glu Val Glu Val Asp Ile  1984
8423  CAG TAT GTC AAG GTG GGA AGC TGT AAG TCT GAA GTA GAG GTG GAT ATC  8470

1985  His Tyr Cys Gln Gly Lys Cys Ala Ser Lys Ala Met Tyr Ser Ile Asp  2000
8471  CAC TAC TGC CAG GGC AAA TGT GCC AGC AAA GCC ATG TAC TCC ATT GAC  8518

2001  Ile Asn Asp Val Gln Asp Gln Cys Ser Cys Cys Ser Pro Thr Arg Thr  2016
8519  ATC AAC GAT GTG CAG GAC CAG TGC TCC TGC TGC TCT CCG ACA CGG ACG  8566

2017  Glu Pro Met Gln Val Ala Leu His Cys Thr Asn Gly Ser Val Val Tyr  2032
8567  GAG CCC ATG CAG GTG GCC CTG CAC TGC ACC AAT GGC TCT GTT GTG TAC  8614

2033  His Glu Val Leu Asn Ala Met Glu Cys Lys Cys Ser Pro Arg Lys Cys  2048
8615  CAT GAG GTT CTC AAT GCC ATG GAG TGC AAA TGC TCC CCC AGG AAG TGC  8662

2049  Ser Lys ***
8663  AGC AAG TGA
```

FIG. 13

```
  1 Met Leu His Asp Phe Tyr Cys Ser Arg Leu Leu Asp Leu Val Phe Leu  16
  1 ATG TTG CAC GAT TTC TAC TGC AGC AGG CTA CTG GAC CTG GTC TTC CTG  48

17 Leu Asp Gly Ser Ser Arg Leu Ser Glu Ala Glu Phe Glu Val Leu Lys  32
 49 CTG GAT GGC TCC TCC AGG CTG TCC GAG GCT GAG TTT GAA GTG CTG AAG  96

33 Ala Phe Val Val Asp Met Met Glu Arg Leu Arg Ile Ser Gln Lys Trp  48
 97 GCC TTT GTG GTG GAC ATG ATG GAG CGG CTG CGC ATC TCC CAG AAG TGG 144

49 Val Arg Val Ala Val Val Glu Tyr His Asp Gly Ser His Ala Tyr Ile  64
145 GTC CGC GTG GCC GTG GTG GAG TAC CAC GAC GGC TCC CAC GCC TAC ATC 192

65 Gly Leu Lys Asp Arg Lys Arg Pro Ser Glu Leu Arg Arg Ile Ala Ser  80
193 GGG CTC AAG GAC CGG AAG CGA CCA TCA GAG CTG CGG CGC ATT GCC AGC 240

81 Gln Val Lys Tyr Ala Gly Ser Gln Val Ala Ser Thr Ser Glu Val Leu  96
241 CAG GTG AAG TAT GCG GGC AGC CAG GTG GCC TCC ACC AGC GAG GTC TTG 288

97 Lys Tyr Thr Leu Phe Gln Ile Phe Ser Lys Ile Asp Arg Pro Glu Ala 112
289 AAA TAC ACA CTG TTC CAA ATC TTC AGC AAG ATC GAC CGC CCT GAA GCC 336

113 Ser Arg Ile Ala Leu Leu Leu Met Ala Ser Gln Glu Pro Gln Arg Met 128
337 TCC CGC ATC GCC CTG CTC CTG ATG GCC AGC CAG GAG CCC CAA CGG ATG 384

129 Ser Arg Asn Phe Val Arg Tyr Val Gln Gly Leu Lys Lys Lys Lys Val 144
385 TCC CGG AAC TTT GTC CGC TAC GTC CAG GGC CTG AAG AAG AAG AAG GTC 432

145 Ile Val Ile Pro Val Gly Ile Gly Pro His Ala Asn Leu Lys Gln Ile 160
433 ATT GTG ATC CCG GTG GGC ATT GGG CCC CAT GCC AAC CTC AAG CAG ATC 480

161 Arg Leu Ile Glu Lys Gln Ala Pro Glu Asn Lys Ala Phe Val Leu Ser 176
481 CGC CTC ATC GAG AAG CAG GCC CCT GAG AAC AAG GCC TTC GTG CTG AGC 528

177 Ser Val Asp Glu Leu Glu Gln Gln Arg Asp Glu Ile Val Ser Tyr Leu 192
529 AGT GTG GAT GAG CTG GAG CAG CAA AGG GAC GAG ATC GTT AGC TAC CTC 576

193 Cys Asp Leu Ala Pro Glu Ala Pro Pro Pro Thr Leu Pro Pro Asp Met 208
577 TGT GAC CTT GCC CCT GAA GCC CCT CCT CCT ACT CTG CCC CCC GAC ATG 624

209 Ala Gln Val Thr Val Gly Pro Gly Leu Leu Gly Val Ser Thr Leu Gly 224
625 GCA CAA GTC ACT GTG GGC CCG GGG CTC TTG GGG GTT TCG ACC CTG GGG 672

225 Pro Lys ***
673 CCC AAG TAA
```

FIG. 16

| Linker | | |
|---|---|---|
| No. 1 | 5' | TATGCTCACCTGTGAAGCATGCCAGGAGCCGGGAGGCCTGTGGTGCCTCCCACAGATGCCCCGGTG |
| | 3' | ACGAGTGGACACTTCGTACGGTCCTCGGCCCTCCGGACCCACCACGGAGGGTGTCTACGGGG |
| No. 2 | 5' | AGCCCCACCACTCTGTATGTGGAGGACATCTCGAACCGCGTTGCACGATTTCTACTGCA |
| | 3' | CCACTCGGGGTGGTGAGACATACACCTCCTGTAGAGCCTTGGCGGGCAACGTGCTAAAGATG |
| No. 3 | | |
| No. 4 | | |

LTU = Light transmission units

LTU = Light transmission units

METHODS OF USING HUMAN VON WILLEBRAND FACTOR GPIB BINDING DOMAIN POLYPEPTIDES

This application is a divisional of U.S. Ser. No. 08/347,594, filed Nov. 30, 1994 and is a continuation of U.S. Ser. No. 08/080,690, filed Jun. 22, 1993, now abandoned, which is a continuation-in-part of U.S. Ser. No. 07/753,815, filed Sep. 3, 1991 now abandoned which is a continuation-in-part of the U.S. application designated in the national stage of PCT International Application No. PCT/US91/01416, filed Mar. 1, 1991; which is a continuation-in-part of U.S. Ser. No. 07/487,767, now abandoned, filed Mar. 2, 1990, the contents of which are hereby incorporated by reference into the present disclosure.

BACKGROUND OF THE INVENTION

Throughout this application various publications are referenced within parentheses. The disclosures of these publications in their entireties are hereby incorporated by reference in this application in order to more fully describe the state of the art to which this invention pertains.

This invention relates to the cloning and production of human von Willebrand Factor analogs and methods of using such analogs.

Structural Features of von Willebrand Factor

Von Willebrand Factor (vWF) is a large plasma protein which is synthesized in the endothelial cells which form the inner surface lining of the blood vessel wall, and by megakarocytes, the precursor of platelets. Large amounts of vWF are found in platelet a-granules, whose contents are released into the blood upon platelet activation. Newly synthesized vWF in endothelial cells may enter the blood via two alternative pathways. Part is secreted constitutively into the blood, mainly as disulfide-linked dimers or small multimers of a 250,000 dalton subunit. Alternatively, part enters secretory organelles called Weibel-Palade bodies. The vWF stored in Weibel-Palade bodies is highly multimeric, ranging in size from that of a dimer to multimers of 50 or more subunits, and can be released from the cells by treatment with secretatogues, such as thrombin. The highly multimeric vWF is the most effective in promoting platelet adhesion.

The gene encoding vWF has been isolated and shown to be greater than 150 kb in length. It is composed of over 20 exons. The vWF mRNA is approximately 9000 bases in length and encodes a pre-pro-vWF of 2813 amino acids. Residues 1–22 form a processed leader sequence which presumably is cleaved after entry of the protein into the rough endoplasmic reticulum. The N-terminal portion of the pro-vWF (741 amino acids) is the pro-peptide which is not present in mature vWF. This peptide is present in the blood and has been shown to be identical to a blood protein previously known as von Willebrand Antigen II (vW AgII). The pro-peptide is essential for the multimerization of vWF. Cells into which a vWF cDNA containing only mature vWF sequences have been introduced produce only dimers. No function is known for the propeptide/vW AgII.

DNA sequence analysis has demonstrated that the pro-vWF precursor is composed of repeated domain subunits. Four different domains have been identified. Mature vWF consists of three A type, three B type, and two C type domains. There are also two complete and one partial D type domain. The pro-peptide consists of two D type domains, leading to the speculation that it may have associated functions.

Mature vWF is a multivalent molecule which has binding sites for several proteins. One of the binding sites recognizes the platelet glycoprotein Ib (GPIb). Using proteolytic digests this site has been localized to the region between amino acid residues 449 and 728 of mature vWF. In addition, vWF has at least two collagen binding sites, at least two heparin binding sites, a Factor VIII binding site, and a RGD site which binds to the platelet GP IIb/IIIa receptor.

Involvement Of VWF In Platelet Adhesion To Subendothelium

Evidence that vWF, and specifically, the binding of vWF to the platelet GPIb receptor, is essential for normal platelet adhesion, is based on both clinical observations and in vitro studies. Patients with the bleeding disorder von Willebrand Disease (vWD) have reduced levels of vWF or are completely lacking in vWF. Alternatively, they may have defective vWF. Another disorder, Bernard-Soulier Syndrome (BSS), is characterized by platelets lacking GPIb receptors.

The in vitro system which most closely approximates the environment of a damaged blood vessel consists of a perfusion chamber in which an everted blood vessel segment (rabbit aorta, human post-mortem renal artery, or the human umbilical artery) is exposed to flowing blood. After stripping off the layer of endothelial cells from the vessel, blood is allowed to flow through the chamber. The extent of platelet adhesion is estimated directly by morphometry or indirectly using radiolabeled platelets. Blood from patients with VWD or BSS does not support platelet adhesion in this system while normal blood does, indicating the need for vWF and platelet GPIb. Moreover, addition of monoclonal antibodies to GPIb prevents platelet adhesion as well. The vWF-dependence of platelet adhesion is more pronounced under conditions of high shear rates, such as that present in arterial flow. Under conditions of low shear rates, platelet adhesion may be facilitated by other adhesion proteins, such as fibronectin. Possibly, the adhesive forces provided by these other proteins are not adequate to support adhesion at high shear forces, and vWF dependence becomes apparent. Also, the multimeric nature of the vWF may provide for a stronger bond by binding more sites on the platelet.

About 20% of patients from whom clots have been removed by angioplasty or by administration of tissue plasminogen activator (tPA) suffer re-occlusion. This is presumably the result of damage to the endothelium during the treatment which results in the adhesion of platelets to the affected region on the inner surface of the vessel. This is followed by the aggregation of many layers of platelets and fibrin onto the previously adhered platelets, forming a thrombus.

To date none of the anti-platelet aggregation agents described in the literature prevent the initial platelet adhesion to the exposed sub-endothelium thereby preventing subsequent clot formation.

The subject invention provides non-glycosylated, biologically active polypeptides which comprise the vWF (von Willebrand Factor) GPIb binding domain. These polypeptides may be used inter alia to inhibit platelet adhesion and aggregation in the treatment of subjects with conditions such as cerebrovascular disorders and cardiovascular disorders. This invention also provides expression plasmids encoding these polypeptides as well as methods of producing by transforming a bacterial cell and recovering such polypeptides. In addition, the subject invention provides methods of treating and preventing cerebrovascular, cardiovascular and other disorders using these polypeptides to inhibit platelet aggregation.

SUMMARY OF THE INVENTION

This invention provides a non-glycosylated, biologically active polypeptide having the amino acid sequence:

X-A-[Cys Ser Arg Leu Leu Asp Leu Val Phe Leu Leu Asp
Gly Ser Ser Arg Leu Ser Glu Ala Glu Phe Glu Val Leu
Lys Ala Phe Val Val Asp Met Met Glu Arg Leu Arg Ile
Ser Gln Lys Trp Val Arg Val Ala Val Val Glu Tyr His
Asp Gly Ser His Ala Tyr Ile Gly Leu Lys Asp Arg Lys
Arg Pro Ser Glu Leu Arg Arg Ile Ala Ser Gln Val Lys
Tyr Ala Gly Ser Gln Val Ala Ser Thr Ser Glu Val Leu
Lys Tyr Thr Leu Phe Gln Ile Phe Ser Lys Ile Asp Arg
Pro Glu Ala Ser Arg Ile Ala Leu Leu Leu Met Ala Ser
Gln Glu Pro Gln Arg Met Ser Arg Asn Phe Val Arg Tyr
Val Gln Gly Leu Lys Lys Lys Lys Val Ile Val Ile Pro Val
Gly Ile Gly Pro His Ala Asn Leu Lys Gln Ile Arg Leu
Ile Glu Lys Gln Ala Pro Glu Asn Lys Ala Phe Val Leu
Ser Ser Val Asp Glu Leu Glu Gln Gln Arg Asp Glu Ile
Val Ser Tyr Leu Cys](SEQ ID NO. 1)-B-COOH
wherein X is NH$_2$-methionine- or NH2-;

A is a sequence of at least 1, but less than 35 amino acids, which sequence is present in naturally occurring vWF, the carboxy terminal amino acid of which is the tyrosine #508 shown in FIG. 12 (SEQ ID NO. 2);

B is a sequence of at least 1, but less than 211 amino acids, which sequence is present in naturally occurring vWF, the amino terminal amino acid of which is the aspartic acid #696 shown in FIG. 12 (SEQ ID NO. 2); and the two cysteines included within the bracketed sequence are joined by a disulfide bond.

In addition, the subject invention provides a method of producing any of the above-described polypeptides which comprises transforming a bacterial cell with an expression plasmid encoding the polypeptide, culturing the resulting bacterial cell so that the cell produces the polypeptide encoded by the plasmid, and recovering the polypeptide so produced.

Furthermore, the subject invention provides a pharmaceutical composition comprising an amount of any of the above-described polypeptides effective to inhibit platelet aggregation and a pharmaceutically acceptable carrier. The subject invention also provides a method of inhibiting platelet aggregation which comprises contacting platelets with an amount of any of the above-described polypeptides effective to inhibit platelet aggregation. In addition, the subject invention provides methods of treating, preventing or inhibiting disorders such as cerebrovascular or cardiovascular disorders or thrombosis, comprising administering to the subject an amount of any of the above-described polypeptides effective to treat or prevent such disorders.

The subject invention also provides a method for recovering a purified, biologically active above-described polypeptide which comprises:

(a) producing in a bacterial cell a first polypeptide having the amino acid sequence of the polypeptide but lacking the disulfide bond;

(b) disrupting the bacterial cell so as to produce a lysate containing the first polypeptide;

(c) treating the lysate so as to obtain inclusion bodies containing the first polypeptide;

(d) contacting the inclusion bodies from step (c) so as to obtain the first polypeptide in soluble form;

(e) treating the resulting first polypeptide so as to form the biologically active polypeptide;

(f) recovering the biologically active polypeptide so formed; and (g) purifying the biologically active polypeptide so recovered.

This figure shows the construction of plasmid pvw1P. A series of vWF CDNA clones in λ gt11 (isolated from a human endothelial cell cDNA library) were isolated. One CDNA clone covering the entire GPIb binding domain was subcloned into the EcoRI site of pUC19. The resulting plasmid, pvW1P, contains a 2.5 kb CDNA insert.

FIG. 2: Construction of pvWF-VA1

This figure shows the construction of plasmid pvWF-VA1. A synthetic oligomer containing an ATG initiation codon located before the amino acid glu-437 (i.e., the 437th amino acid in the vWF protein shown in FIG. 12 (SEQ ID NO. 2)) was ligated to plasmid pvW1P digested with NdeI and Bsu36I. The resulting plasmid was designated pvWF-VA1, and has been deposited in *E. coli* strain Sφ930 under ATCC Accession No. 68530.

Figure 3:
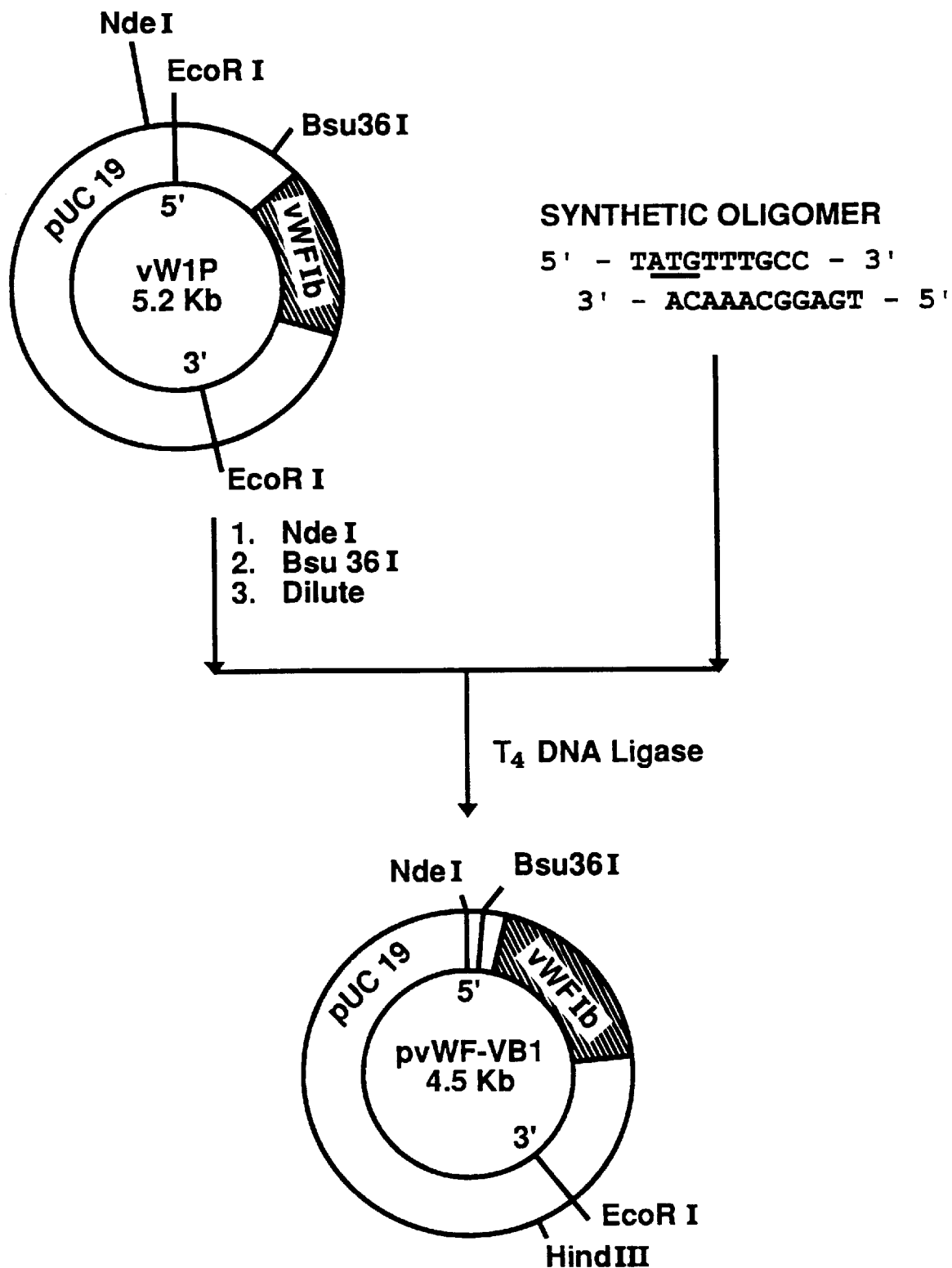

FIG. 3: Construction of pvWF-VB1

This figure shows the construction of plasmid pvWF-VB1. A synthetic oligomer containing an ATG initiation codon located before the amino acid phe-443 (see FIG. 12 (SEQ ID NO. 2)) was ligated to plasmid pvwlp digested with NdeI and Bsu36I. The resulting plasmid was designated pvWF-VB1.

Figure 4:
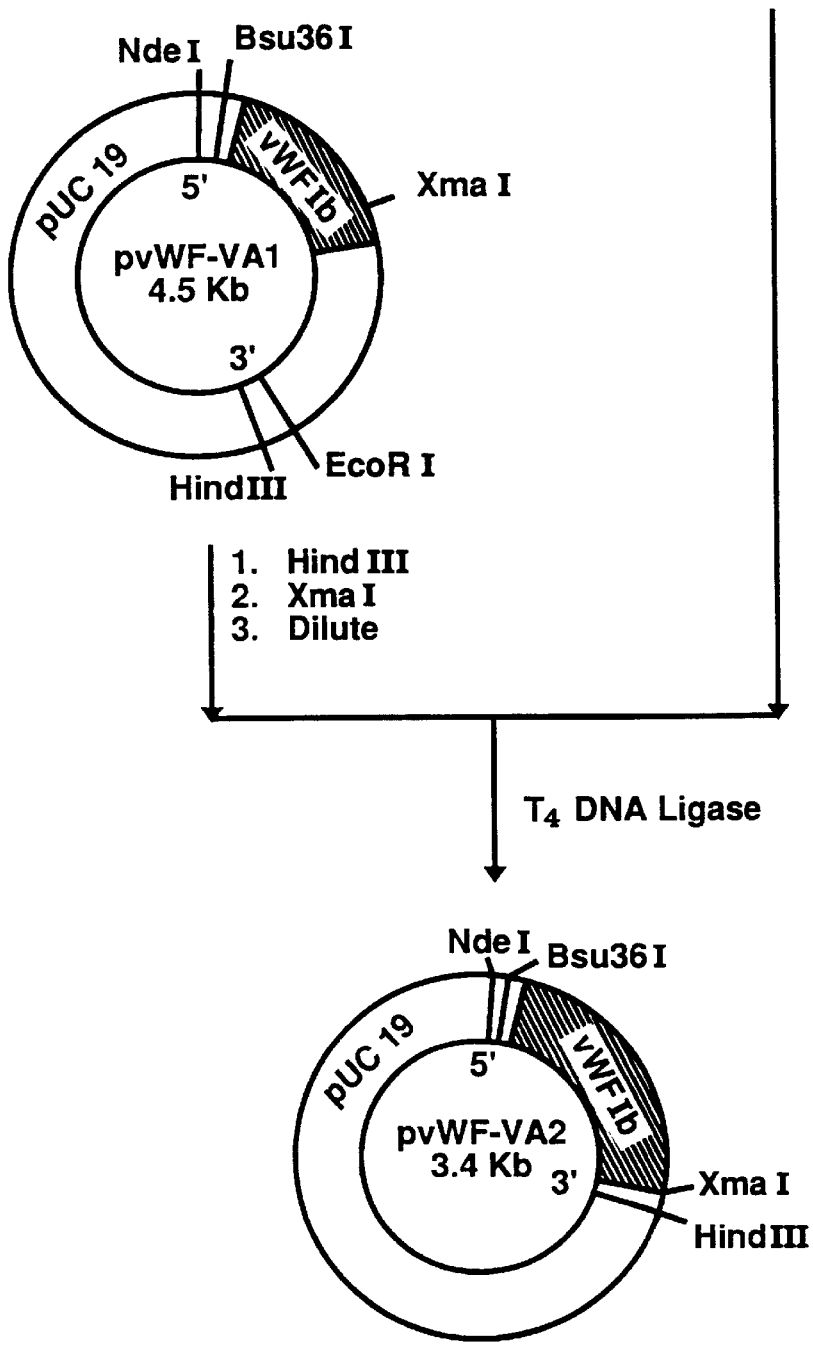

FIG. 4: Construction of pvWF-VA2

This figure shows the construction of plasmid pvWF-VA2. A synthetic oligomer containing a TAA termination codon located after the amino acid lys-728 (see FIG. 12 (SEQ ID NO. 2)) was ligated to plasmid pvWF-VA1 digested with HindIII and XmaI.

The resulting plasmid was designated pvWF-VA2.

Figure 5:
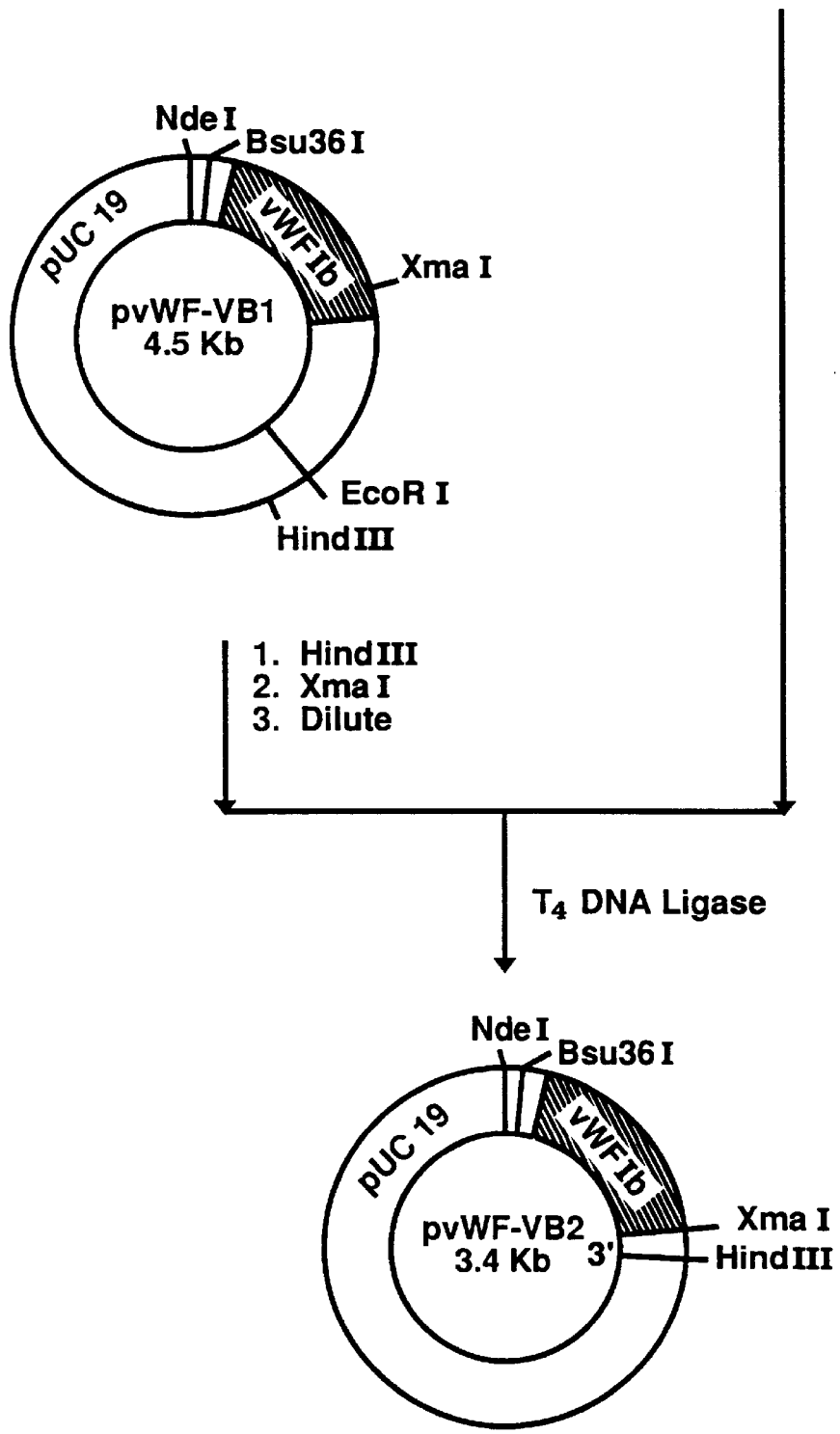

FIG. 5: Construction of pvWF-VB2

This figure shows the construction of plasmid pvWF-VB2. A synthetic oligomer containing a TAA termination codon was ligated to plasmid pvWF-VB1 digested with HindIII and XmaI. The resulting plasmid was designated pvWF-VB2.

Figure 6:
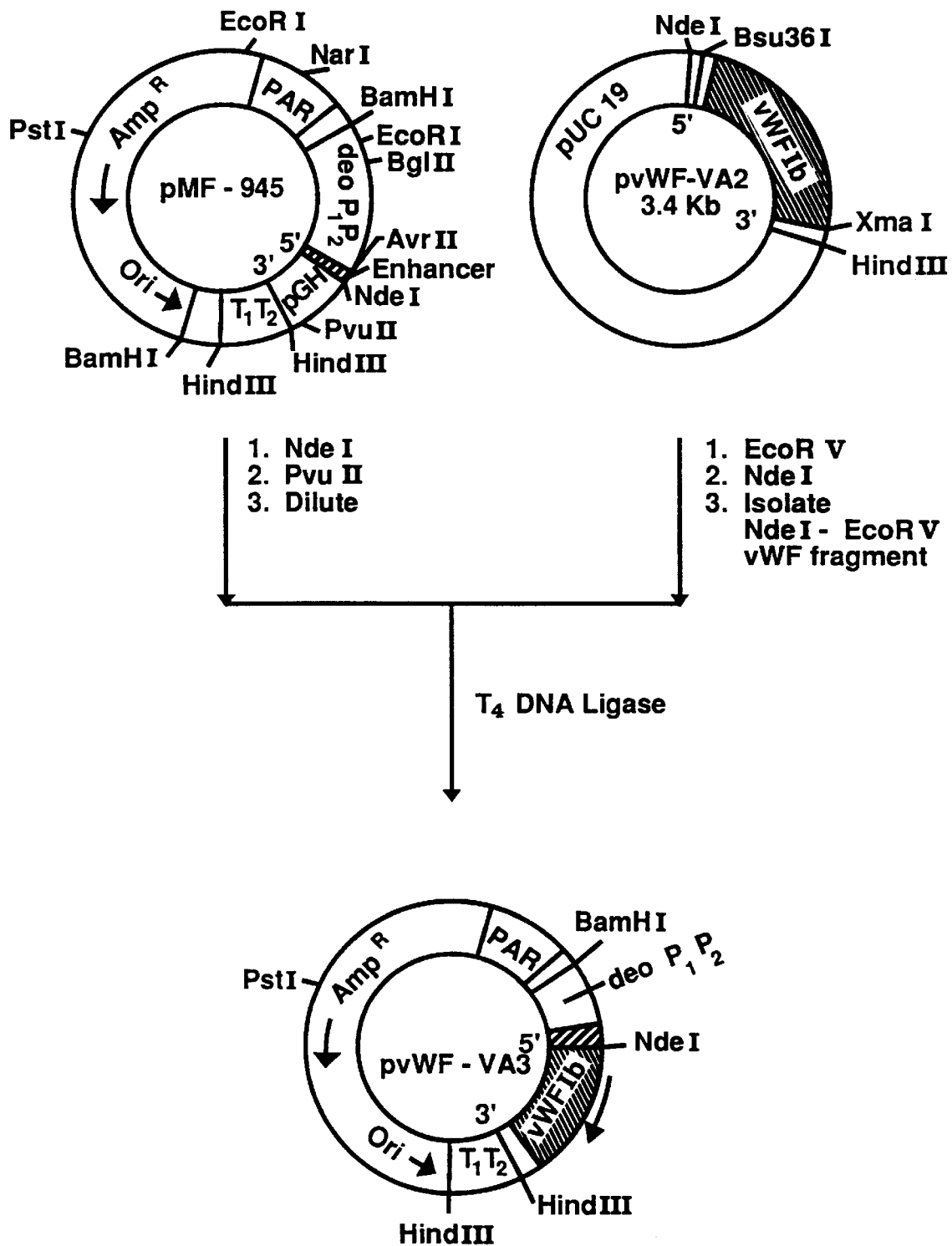

FIG. 6: Construction of pvWF-VA3

This figure shows the construction of plasmid pvWF-VA3. An NdeI-EcoRV fragment was isolated from plasmid pvWF-VA2 and ligated to plasmid pMF-945 (constructed as described in FIG. 11) digested with NdeI and PvuII. The plasmid obtained was designated pvWF-VA3. The plasmid expresses VA, a vWF GPIb binding domain polypeptide which includes amino acids 437 to 728 (see FIG. 12 (SEQ ID NO. 2)) under the control of the deo $P_1P_2$ promoter.

Figure 7:
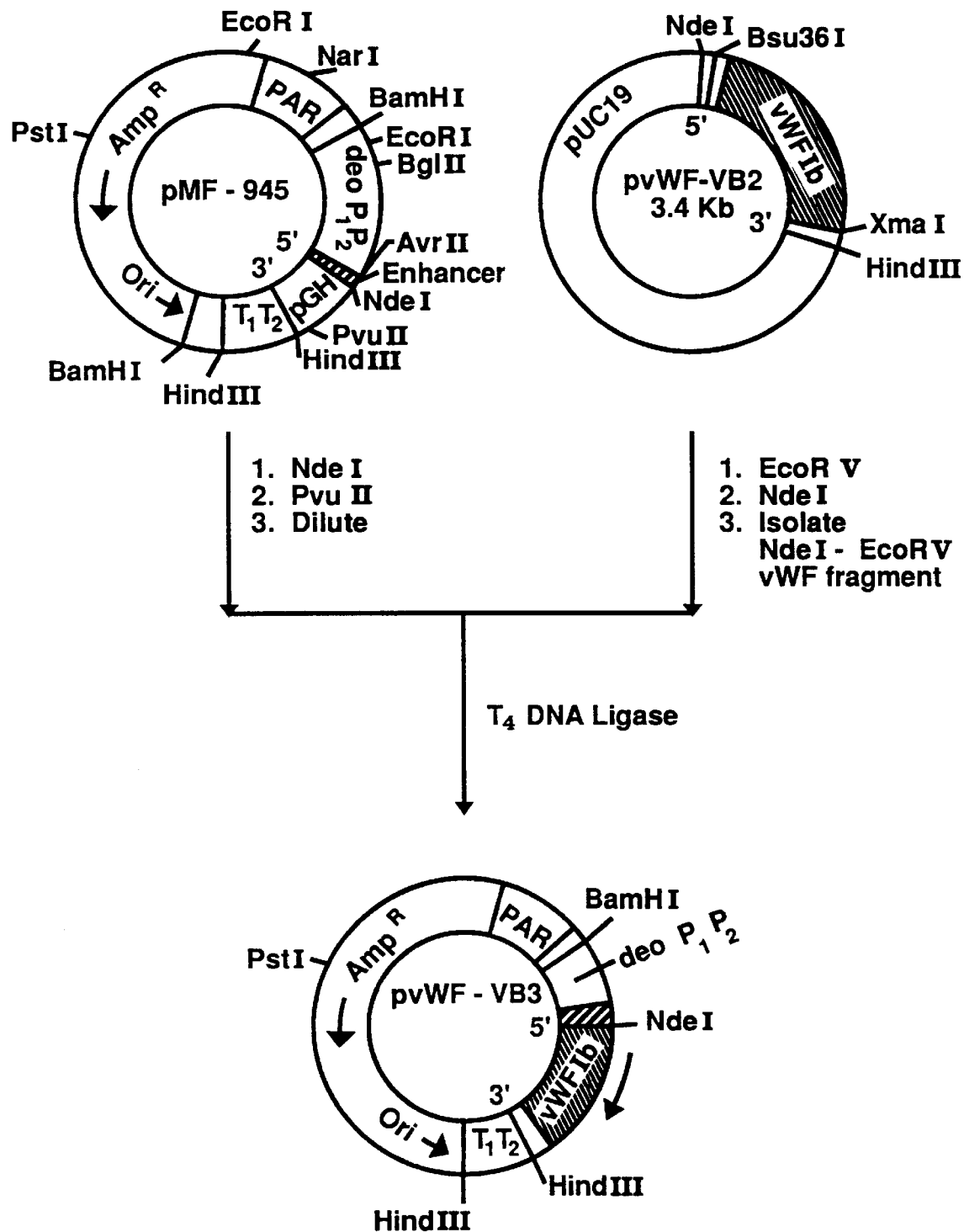

FIG. 7: Construction of pvWF-VB3

This figure shows the construction of plasmid pvWF-VB3. An NdeI-EcoRV fragment was isolated from plasmid pvWF-VB2 and ligated to plasmid pMF-945 digested with NdeI and PvuII. The plasmid obtained was designated pvWF-VB3. The plasmid expresses VB, a vWF GPIb binding domain polypeptide which includes amino acids 443 to 728 under the control of the deo $P_1P_2$ promoter.

Figure 8:
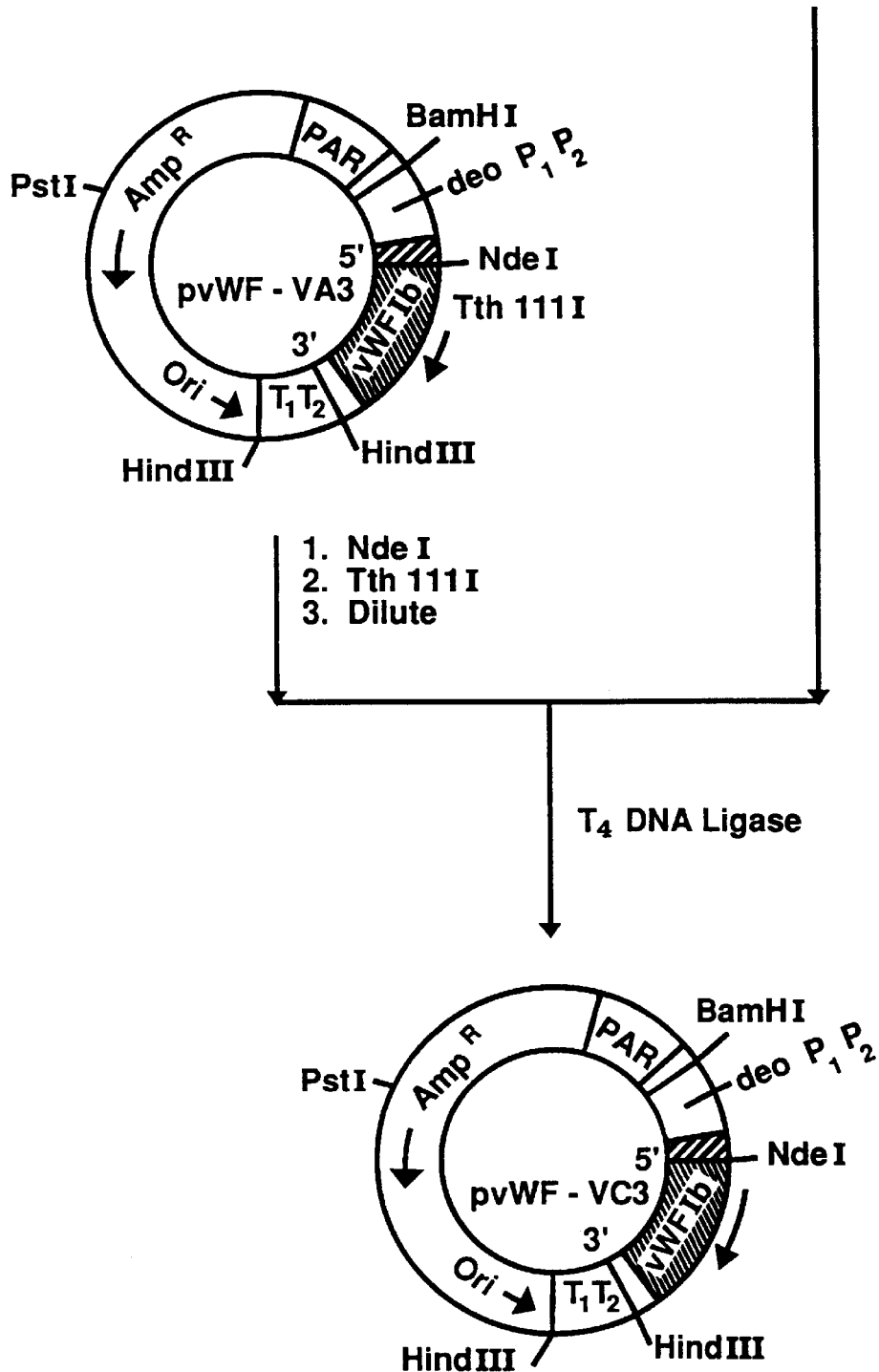

FIG. 8: Construction of pvWF-VC3

This figure shows the construction of plasmid pvWF-VC3. A synthetic linker was ligated to pvWF-VA3 digested with NdeI and Tth111I. The plasmid obtained was designated pvWF-VC3, and has been deposited with the ATCC under ATCC Accession No. 68241. The plasmid expresses VC (also referred to as VCL or VC3), a vWF GPIb binding domain polypeptide which includes amino acids 504 to 728 (see FIG. 12 (SEQ ID NO. 2)) under the control of the deo $P_1P_2$ promoter.

FIG. 9: Construction of pvWF-VD3

This figure shows the construction of plasmid pvWF-VD3. A synthetic linker was ligated to pvWF-VA3 digested with NdeI and Tth111I. The plasmid obtained was designated pvWF-VD3. The plasmid expresses VD, a vWF GPIb binding domain polypeptide which includes amino acids 513 to 728 (see FIG. 12 (SEQ ID NO. 2)) under the control of the deo $P_1P_2$ promoter.

Figure 10:
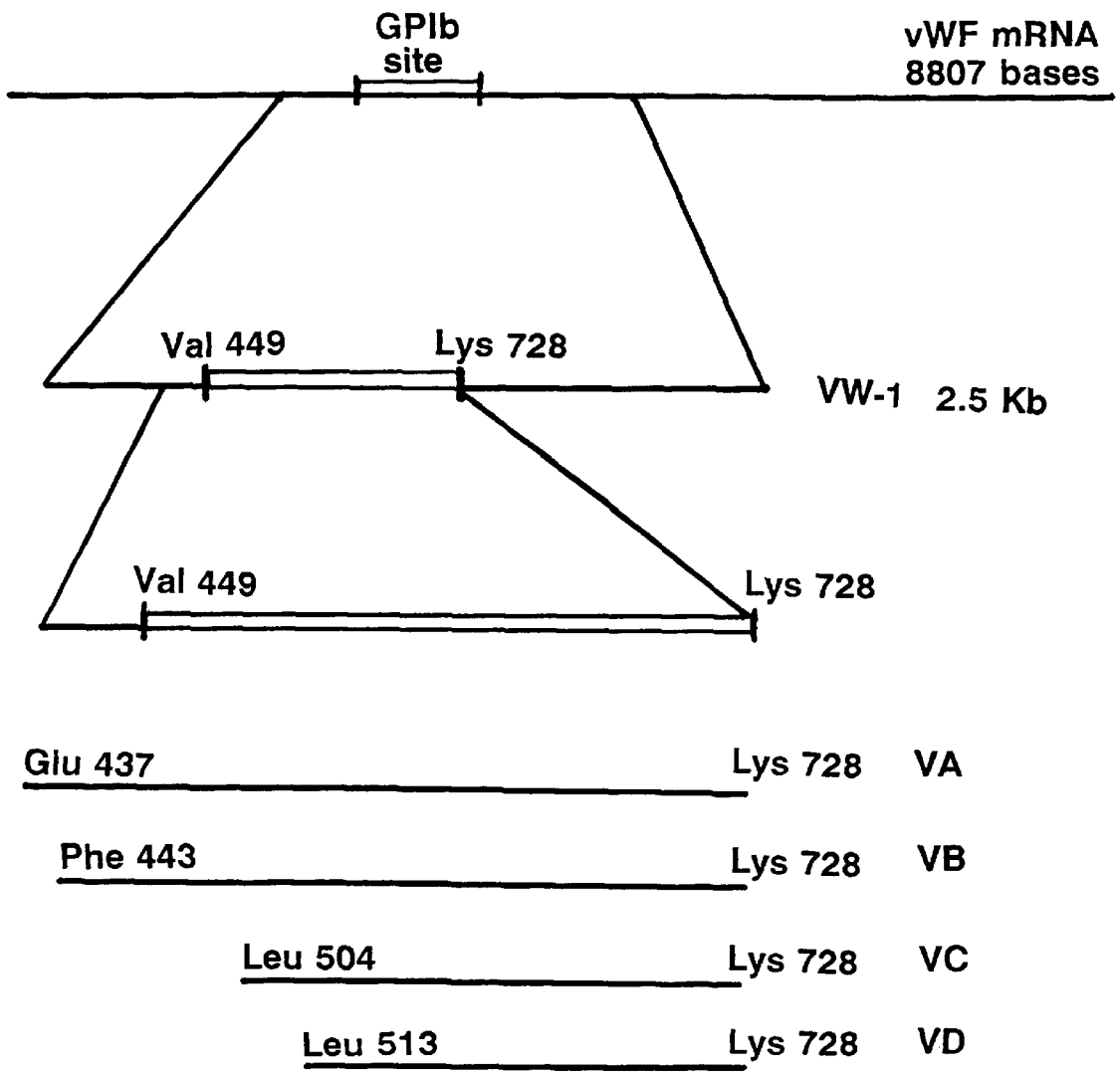

FIG. 10: Relative Alignment of Plasmids Expressing vWF-GPIb Binding Domain Polypeptides This figure shows the relative alignment of the plasmids expressing the vWF-GPIb binding domain polypeptides. Also shown on the top two lines are representations of the vWF cDNA and the location of the GPIb binding domain coding region within the cDNA.

Figure 11:
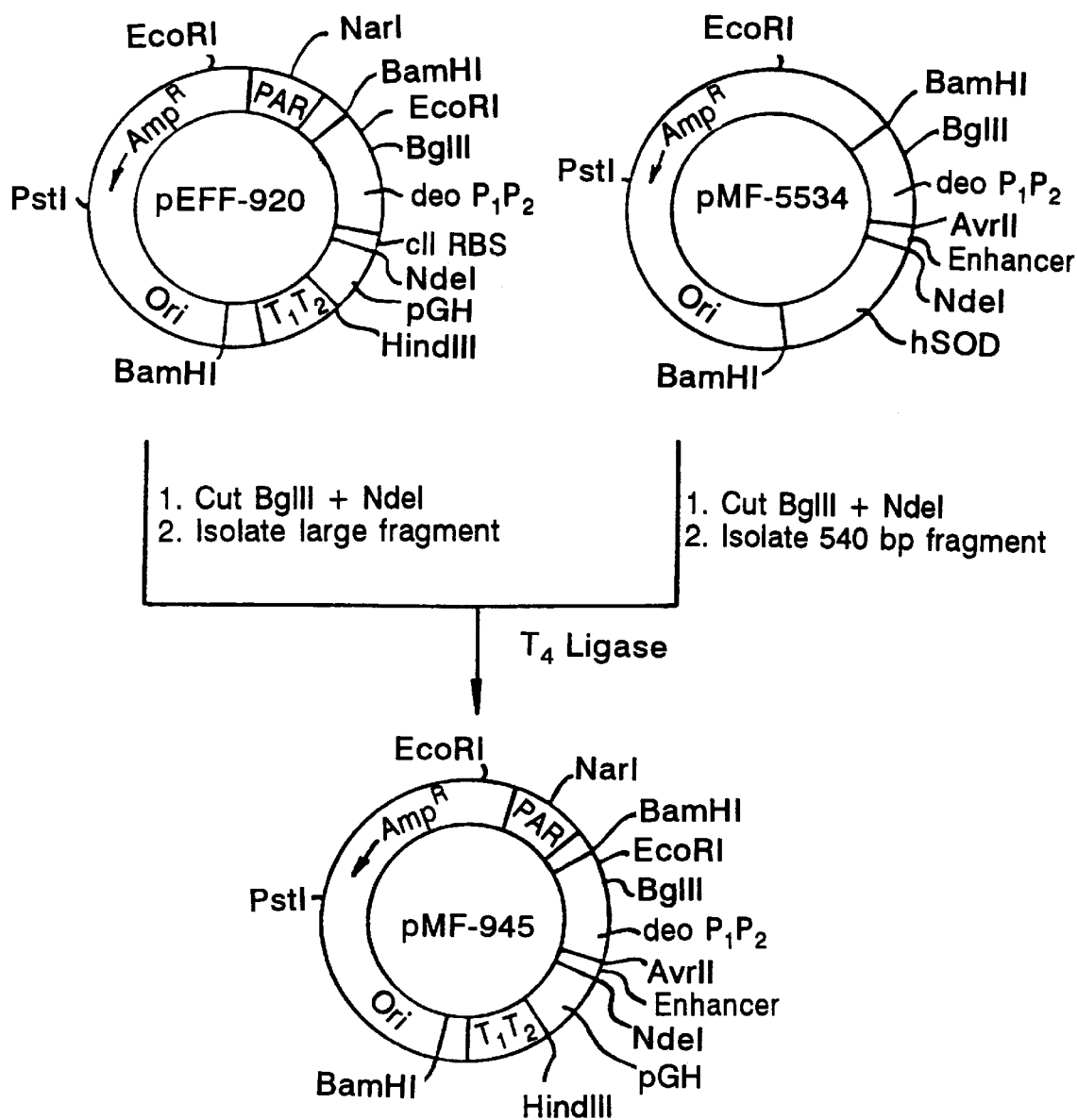

FIG. 11: Construction of Plasmid pMF-945

This figure shows the construction of plasmid pMF-945. Plasmid pEFF-920 (in *Escherichia coli* Sφ930, ATCC Accession No. 67706) was cleaved with BglII and NdeI, and the large fragment was isolated. This fragment was ligated to the small 540 bp fragment produced by cleaving plasmid pMF-5534 (ATCC Accession No. 67703) with BglII and NdeI. This produces plasmid pMF-945 which harbors the PAR sequence and in 5' and 3' order the deo $P_1P_2$ promoter sequences, the modified deo ribosomal binding site with an enhancer sequence, a pGH analog coding sequence and the $T_1T_2$ transcription termination sequences. Plasmid pMF-945 is a high level expressor of pGH analog protein.

FIGS. 12A–12H (SEQ ID NO. 2): Translated CDNA Sequence of Mature Human vWF

This figure which consists of FIGS. 12A, 12B, 12C, 12D, 12E, 12F, 12G and 12H shows the translated cDNA sequence of mature human von Willebrand Factor.

This sequence was compiled using the data disclosed by Verweij, C. L., et al., EMBO Journal 5: 1839–1847 (1986) and Sadler, J. E., et al., Proc. Natl. Acad. Sci. 82: 6394–6398 (1985). This nucleotide sequence commences with nucleotide number 2519 (where nucleotide 1 relates to the start of the coding sequence for the signal peptide) and terminates with nucleotide 8668, a total of 6150 nucleotides encoding mature vWF consisting of 2050 amino acids. The translated amino acid sequence commences with amino acid number 1 and terminates with amino acid number 2050. The corresponding nucleotide and amino acid designations are used throughout this application.

FIG. 13: Translated Sequence of VC, the vWF GPIb Binding Domain Polypeptide Expressed by Plasmids pvWF-VC3 and pvWF-VCL This figure shows the translated sequence of the von Willebrand Factor GPIb binding domain polypeptide expressed by plasmids pvWF-VC3 (ATCC Accession No. 68241) and pvWF-VCL (ATCC Accession No. 68242).

The first codon ATG encoding the translation initiation codon methionine has been added to the nucleotide sequence corresponding to nucleotides 4028 to 4702 of the sequence of FIG. 12. This sequence encodes a polypeptide containing 225 amino acids (plus the initiation methionine) corresponding to amino acid Leu 504 to amino acid Lys 728 of FIG. 12, i.e. 226 amino acids in total.

Figure 14:
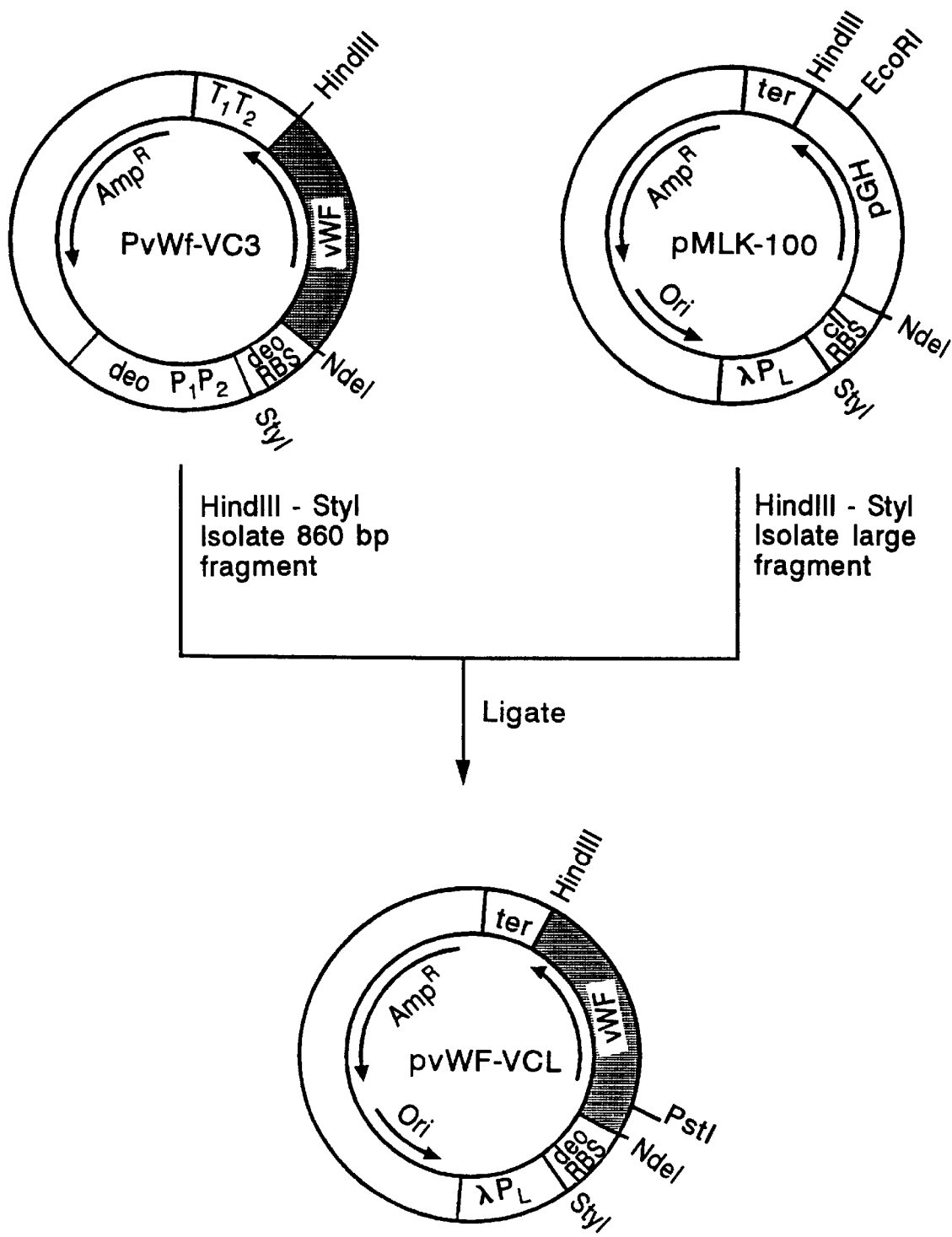

FIG. 14: Construction of pvWF-VCL

This figure shows the construction of plasmid pvWF-VCL. Plasmid pvWF-VC3 was digested with HindIII and StyI and the 860 base pair fragment isolated. This fragment was ligated with the large fragment isolated from the HindIII-StyI digest of plasmid pMLK-100. The resulting plasmid was designated pvWF-VCL and deposited in *E.coli* 4300(F⁻) with the ATCC under ATCC Accession No. 68242. This plasmid expresses VCL, the same vWF GPIb binding domain polypeptide as pvWF-VC3 (methionine plus amino acids 504–728), however under control of the $\lambda P_L$ promoter and the deo ribosomal binding site.

Figure 15:
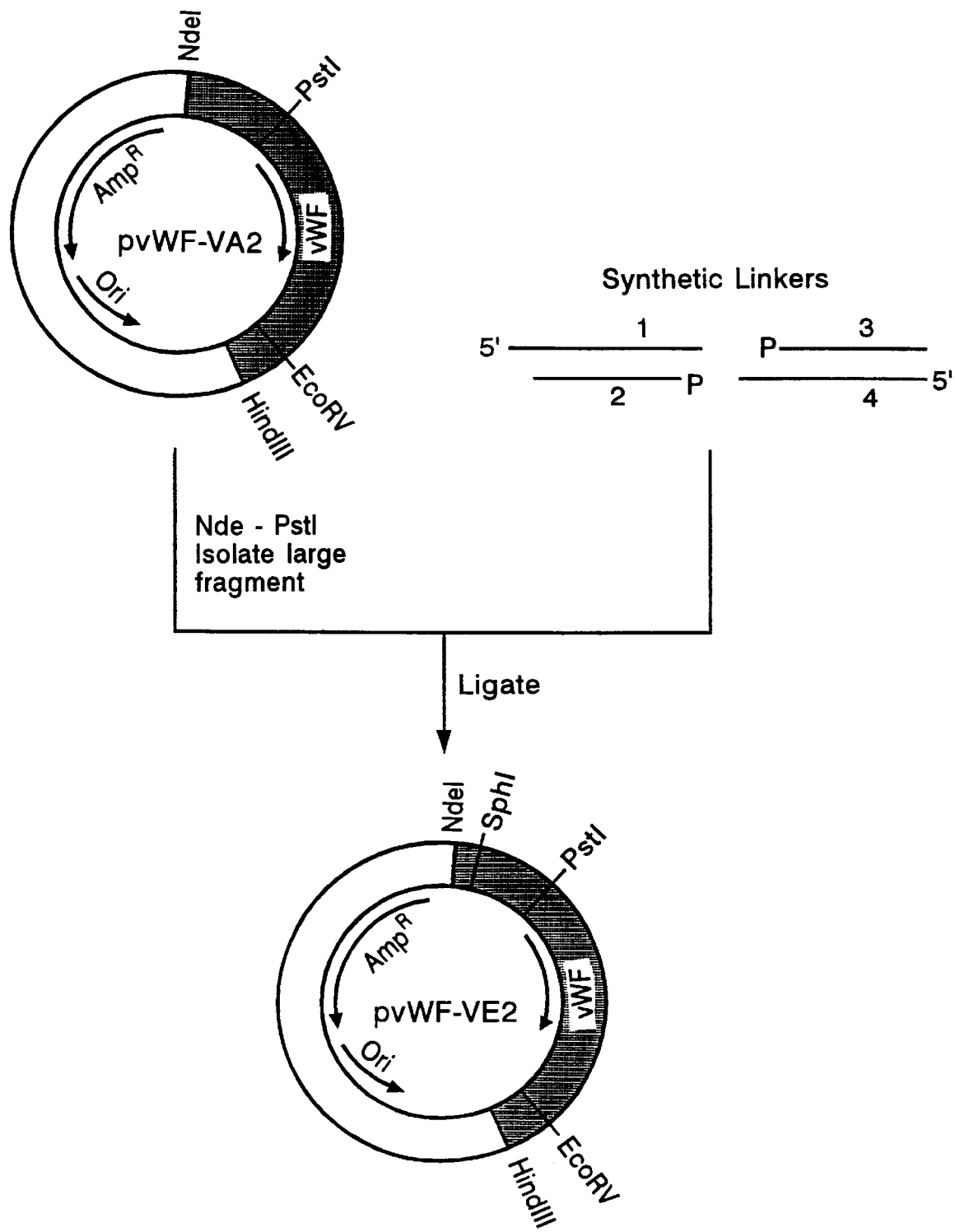

FIG. 15: Construction of Plasmid pvWF-VE2

Plasmid pvWF-VA2 was digested with NdeI and PstI and the large fragment isolated. Synthetic oligomers No. 2 and No. 3 (shown in FIG. 16) were treated with T4 polynucleotide kinase. The large pvWF-VA2 fragment was then ligated with synthetic oligomers No. 1 and No. 4, (shown in FIG. 16) (SEQ ID NO. 21, for No. 1 and Seq ID NO. 25 for No. 4) and with kinased oligomers No. 2 and No. 3. The resulting plasmid was designated pvWF-VE2.

FIG. 16: Synthetic Oligomers Used in Construction of pvWF-VE2.

This figure shows the four synthetic linkers (Nos. 1–4) used in construction of pvWF-VE2.

Figure 17:
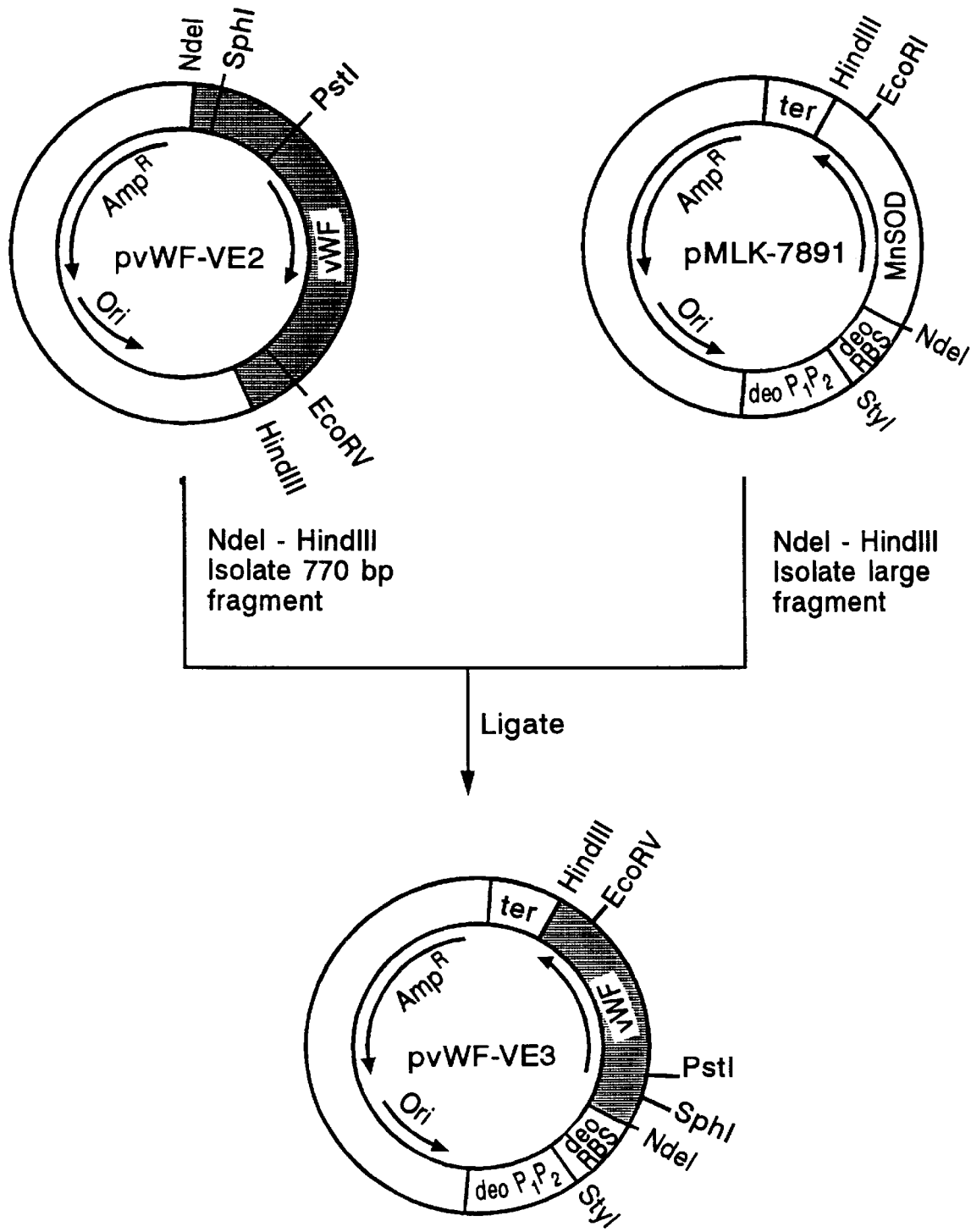

FIG. 17: Construction of Plasmid pvWF-VE3

Plasmid pvWF-VE2 was digested with NdeI and HindIII and the small 770 bp fragment isolated and ligated with the large fragment isolated from the NdeI-HindIII digest of plasmid pMLK-7891. The resulting plasmid was designated pvWF-VE3.

Figure 18:
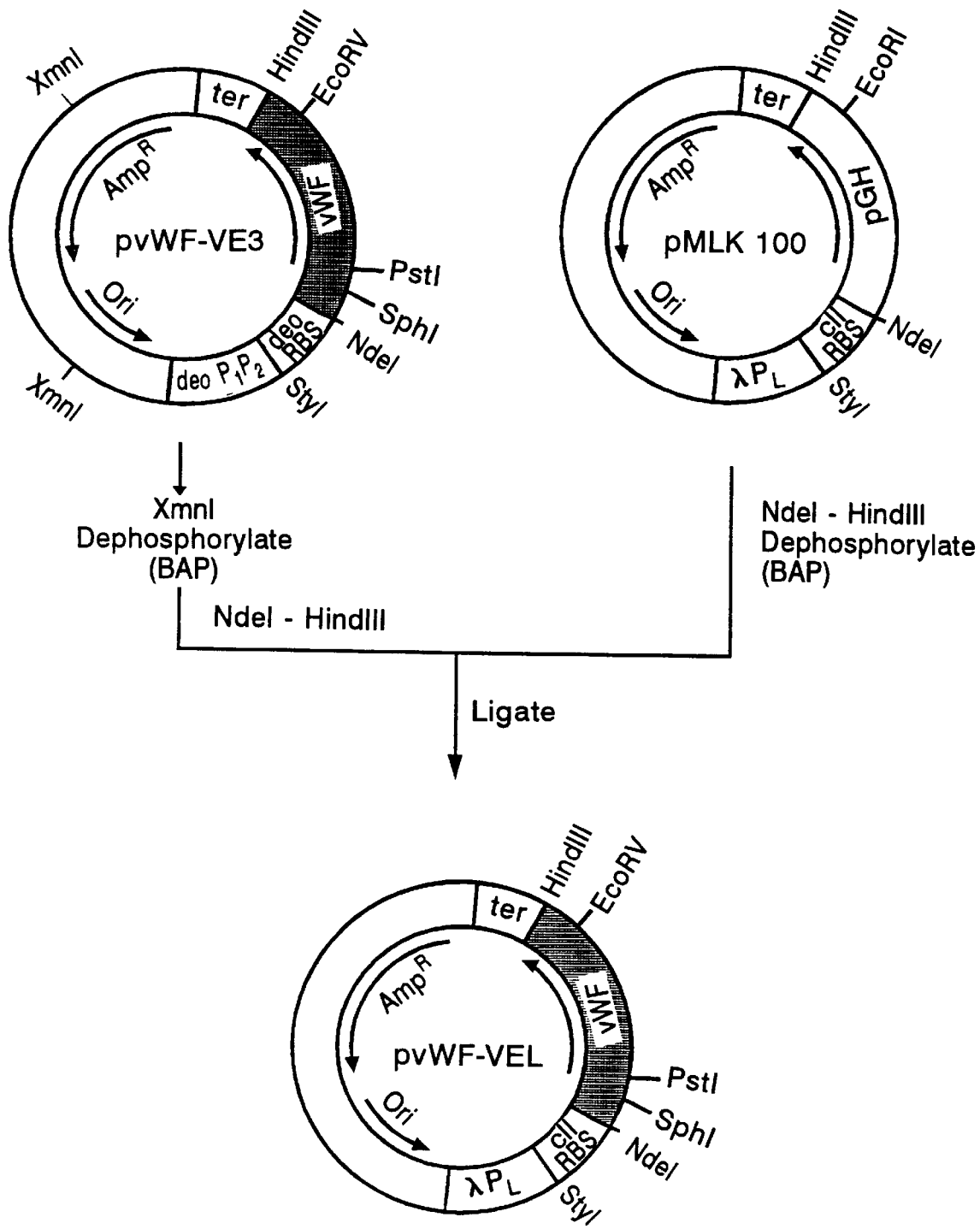

FIG. 18: Construction of Plasmid pvWF-VEL

Plasmid pvWF-VE3 was digested with XmnI, treated with bacterial alkaline phosphatase (BAP), and further digested with NdeI and HindIII. Plasmid pMLK-100 was digested with NdeI and HindIII and treated with BAP. The two digests were mixed and ligated, producing plasmid pvWF-VEL which expresses the DNA sequence corresponding to amino acids 469–728 of mature vWF under the control of the $\lambda P_L$ promoter and the cII ribosomal binding site.

Figure 19:
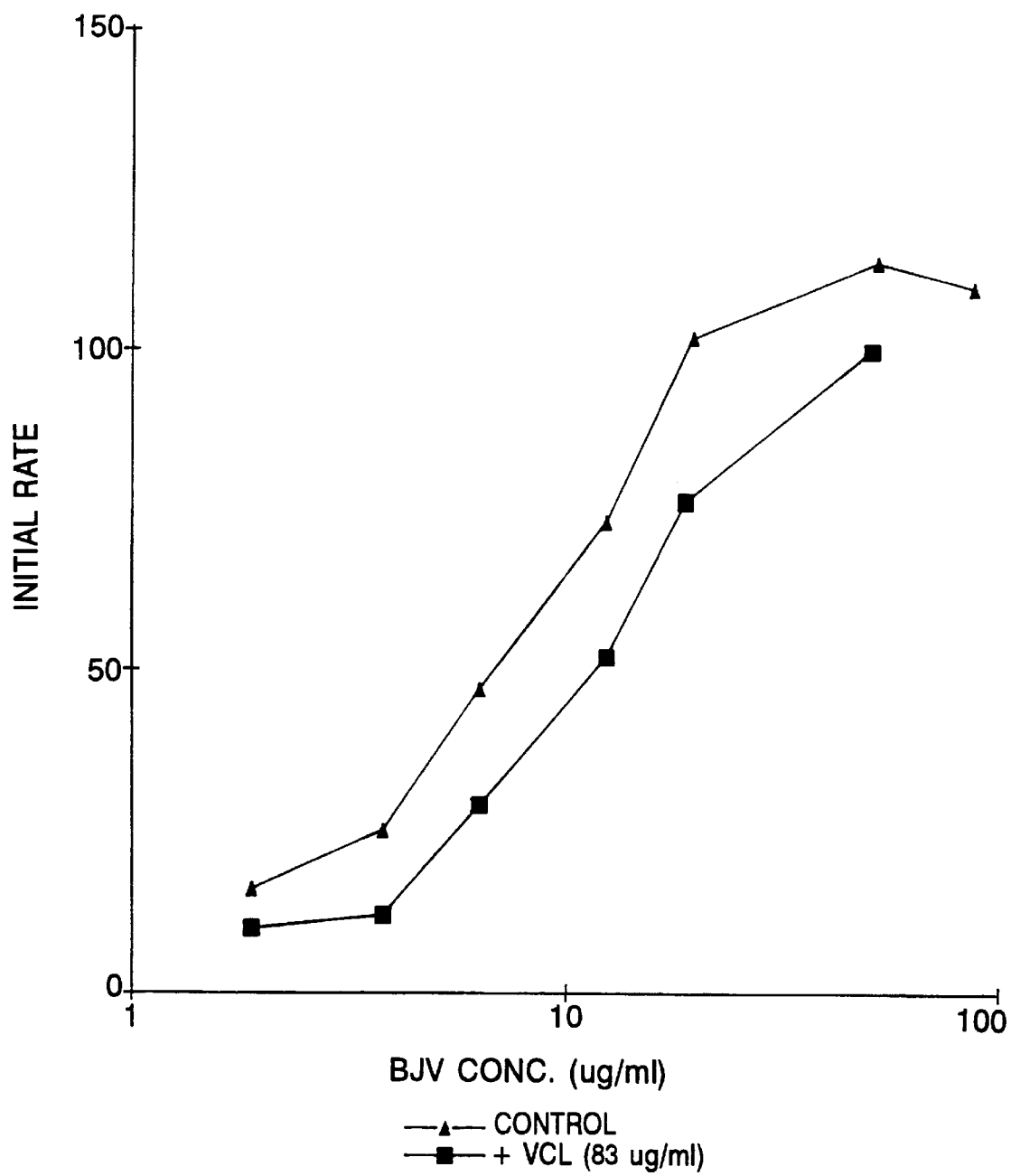

FIG. 19: The Effect of VCL on BJV-Induced Aggregation in Human Platelet Rich Plasma (PRP)

This figure provides the results of a standardized von Willebrand Factor (vWF)-dependent aggregation assay using human PRP.

Figure 20:
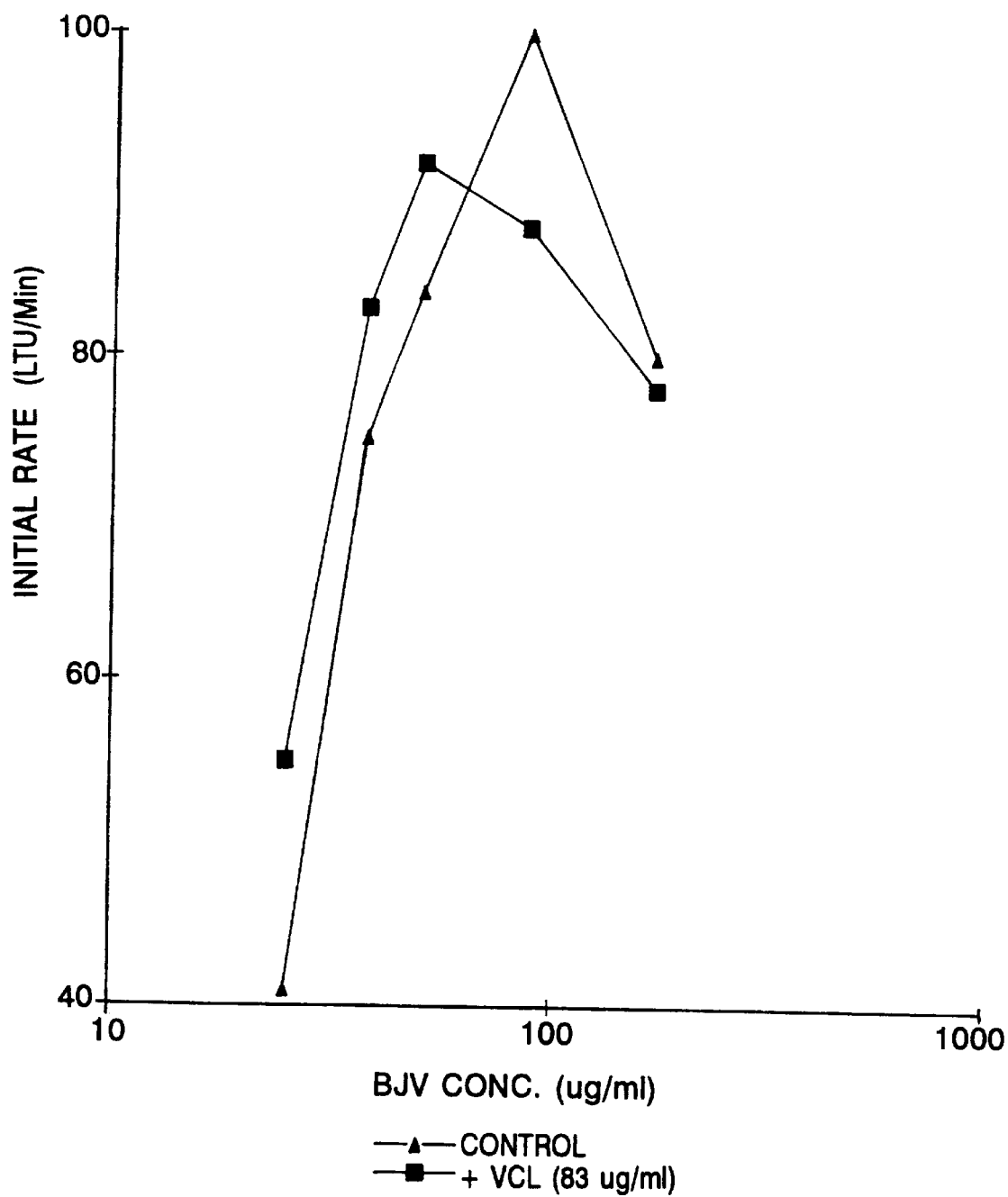

FIG. 20: The Effect of VCL on BJV-Induced Aggregation in Rat PRP

This figure provides the results of a standardized von Willebrand Factor (vWF)-dependent aggregation assay using rat PRP.

Figure 21:
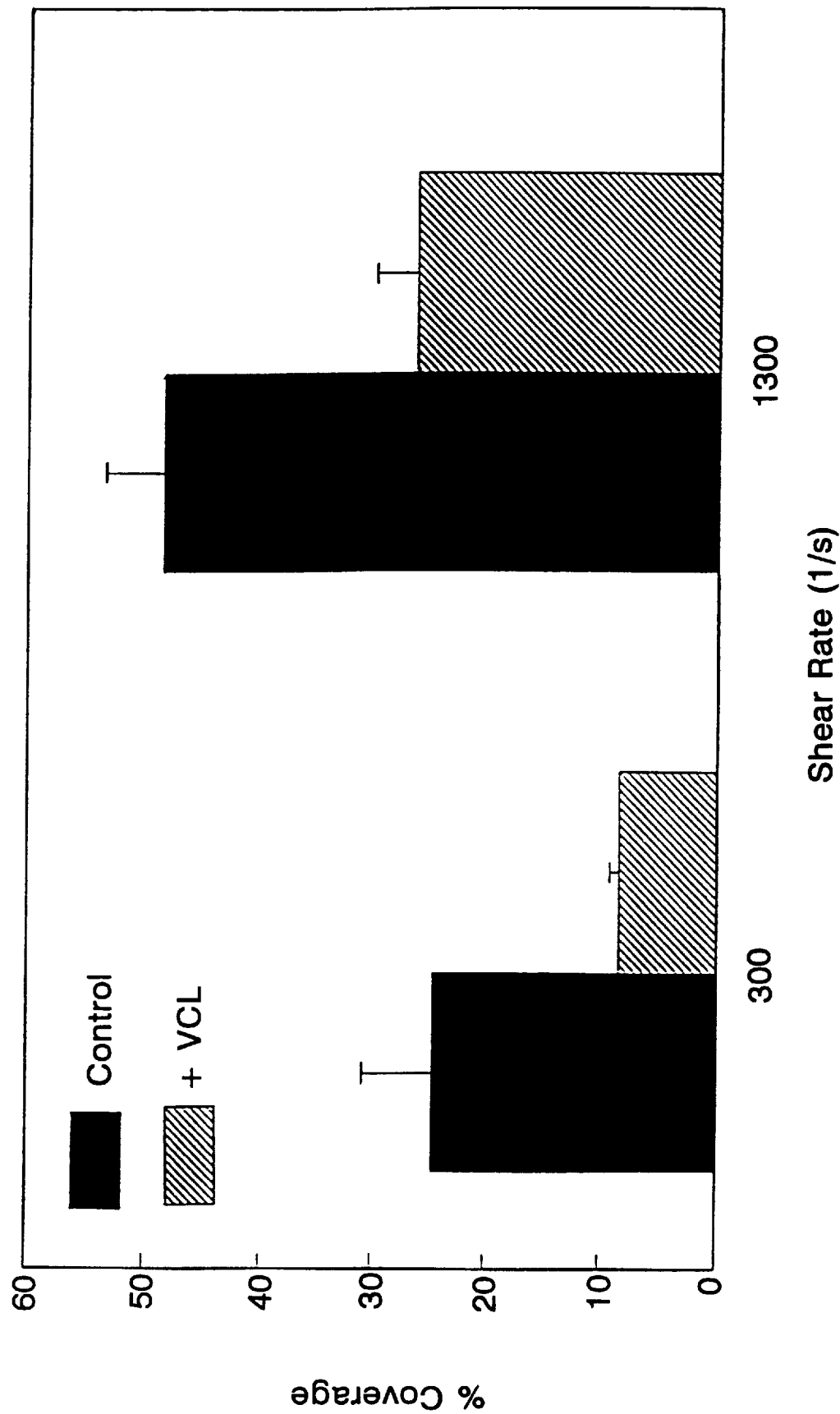

FIG. 21: Inhibition of Platelet Adhesion to Endothelial cell Extracellular Matrix (ECM) by the GPIb Binding Domain Polypeptide VCL This figure shows the effect of VCL on binding of platelets to immobilized ECM as described in Example 9. At both low and high shear rates, VCL is effective in reducing platelet adhesion to ECM in vitro.

Figure 22:
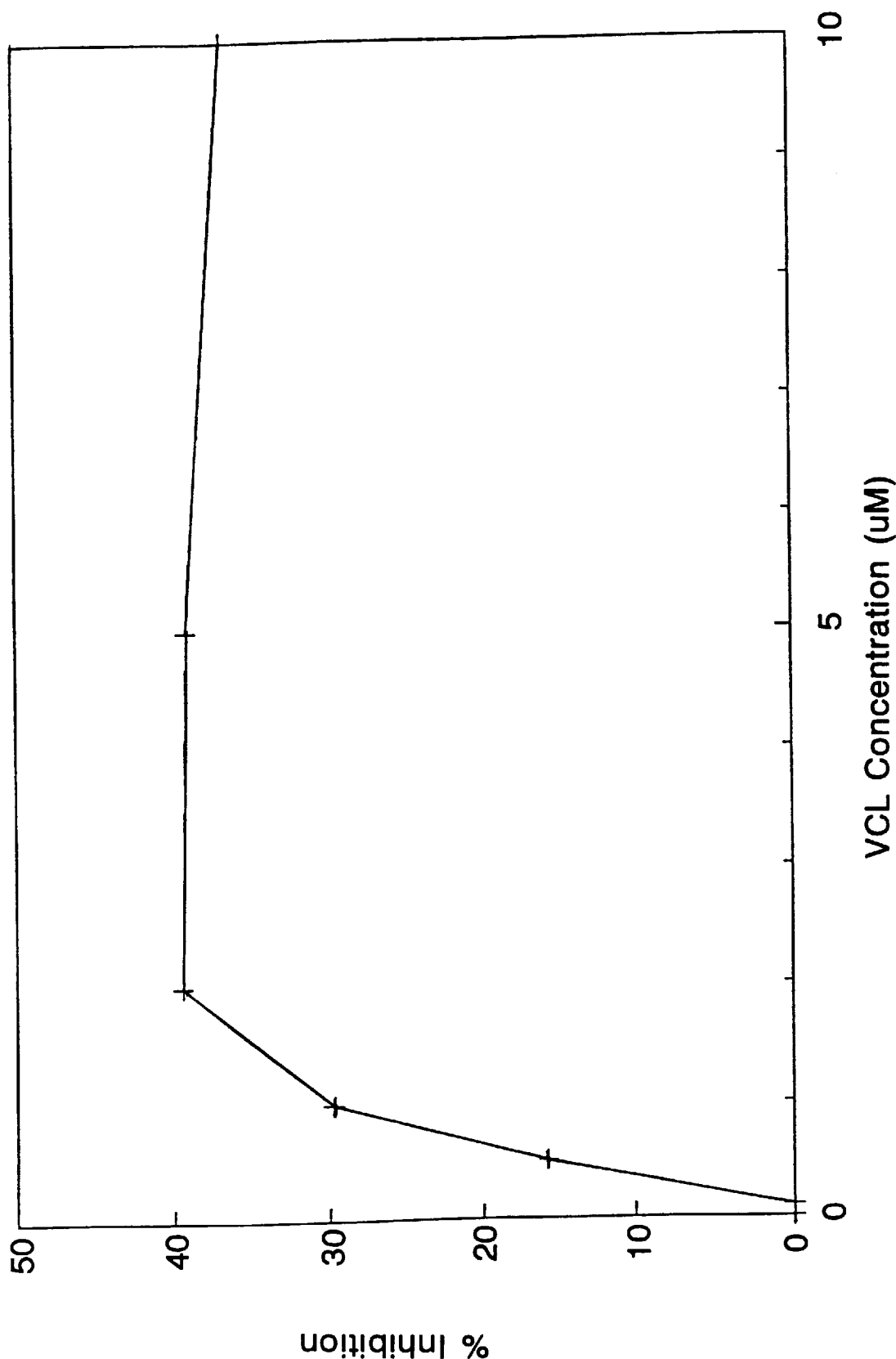

FIG. 22: Dose Response Curve of Inhibition of Platelet Adhesion to Endothelial Cell Extracellular Matrix (ECM) by the GPIb Binding Domain Polypeptide VCL A series of concentrations of VCL was tested to determine the $IC_{50}$ of VCL in vitro as described in Example 9. As seen in the figure, the $IC_{50}$ is about 0.8 $\mu$M VCL, while maximal inhibition is achieved at about 2 $\mu$M VCL.

Figure 23:
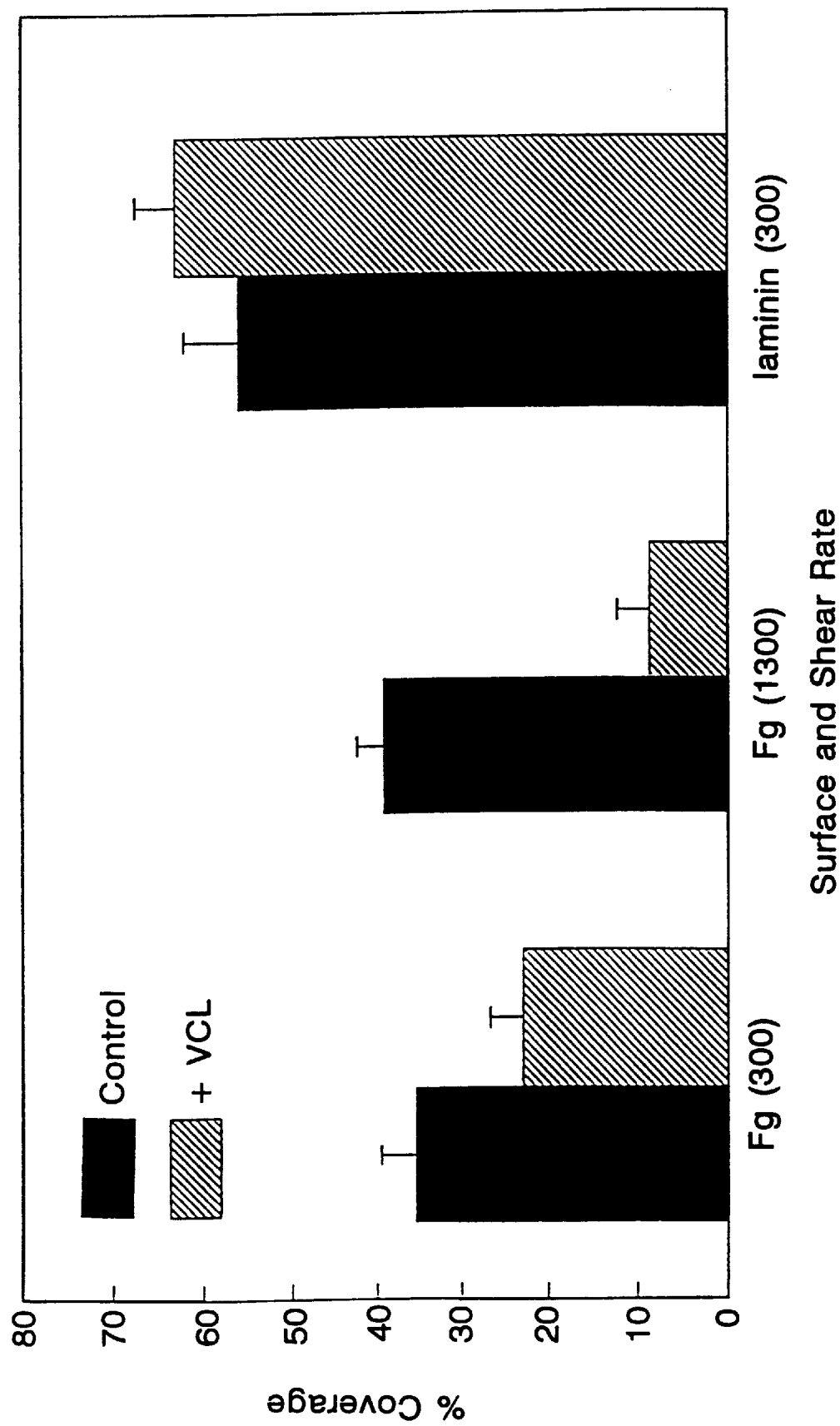

FIG. 23: Inhibition of Platelet Adhesion to Fibringen by the GPIb Binding Domain Polypeptide VCL Platelet adhesion to immobilized fibrinogen and laminin were tested in the glass cover slip model as described in Example 9. VCL was more inhibitory of platelet adhesion to fibrinogen at a high shear rate than at a low shear rate. VCL did not inhibit binding of platelets to laminin.

Figure 24:
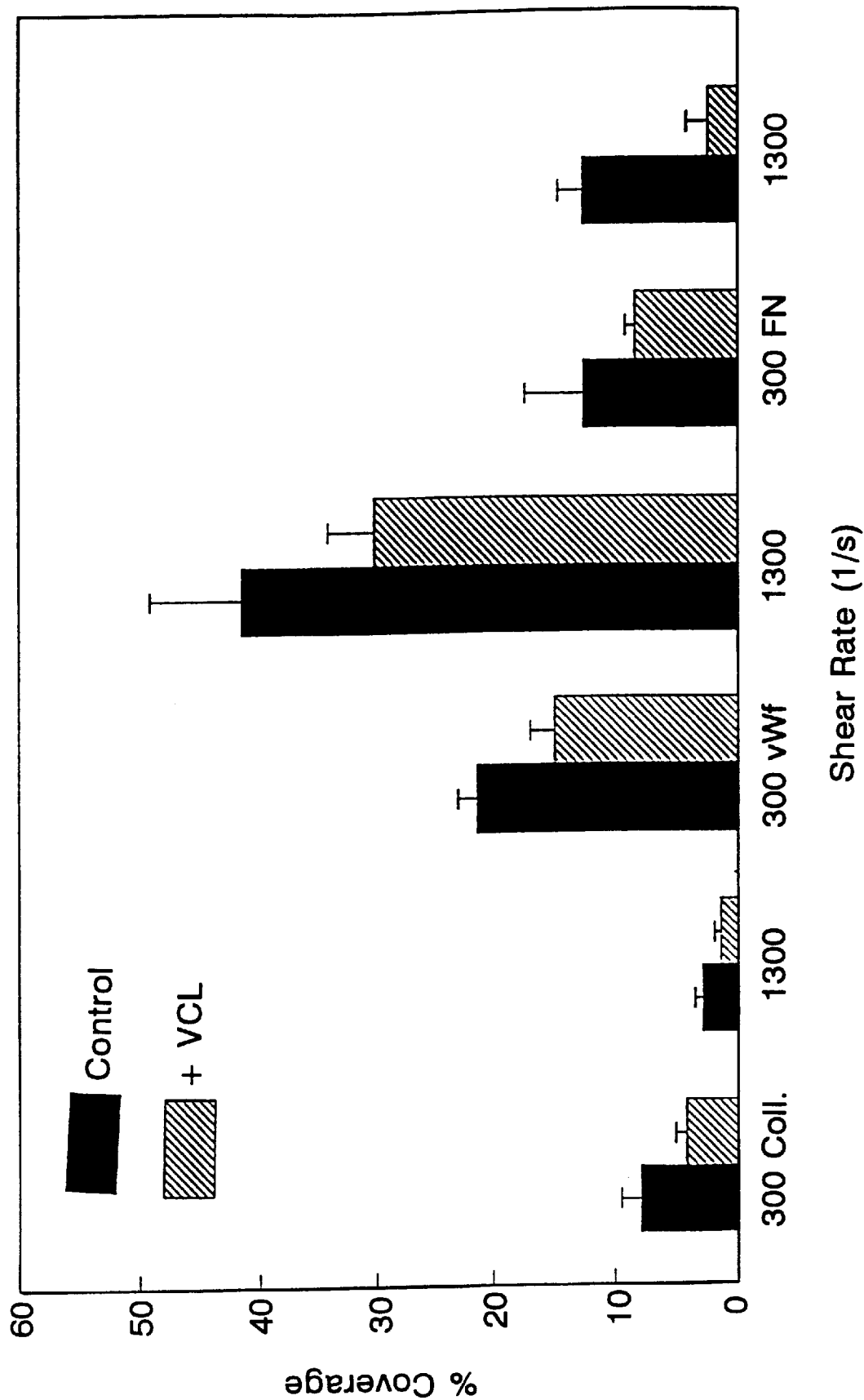

FIG. 24: Inhibition of Platelet Adhesion to Collagen, vWF, and Fibronectin by the GPIb Binding Domain Polypeptide VCL Platelet adhesion to immobilized collagen (Type I), immobilized vWF, and immobilized fibronectin was tested in the model as described in Example 9.

Figure 25:
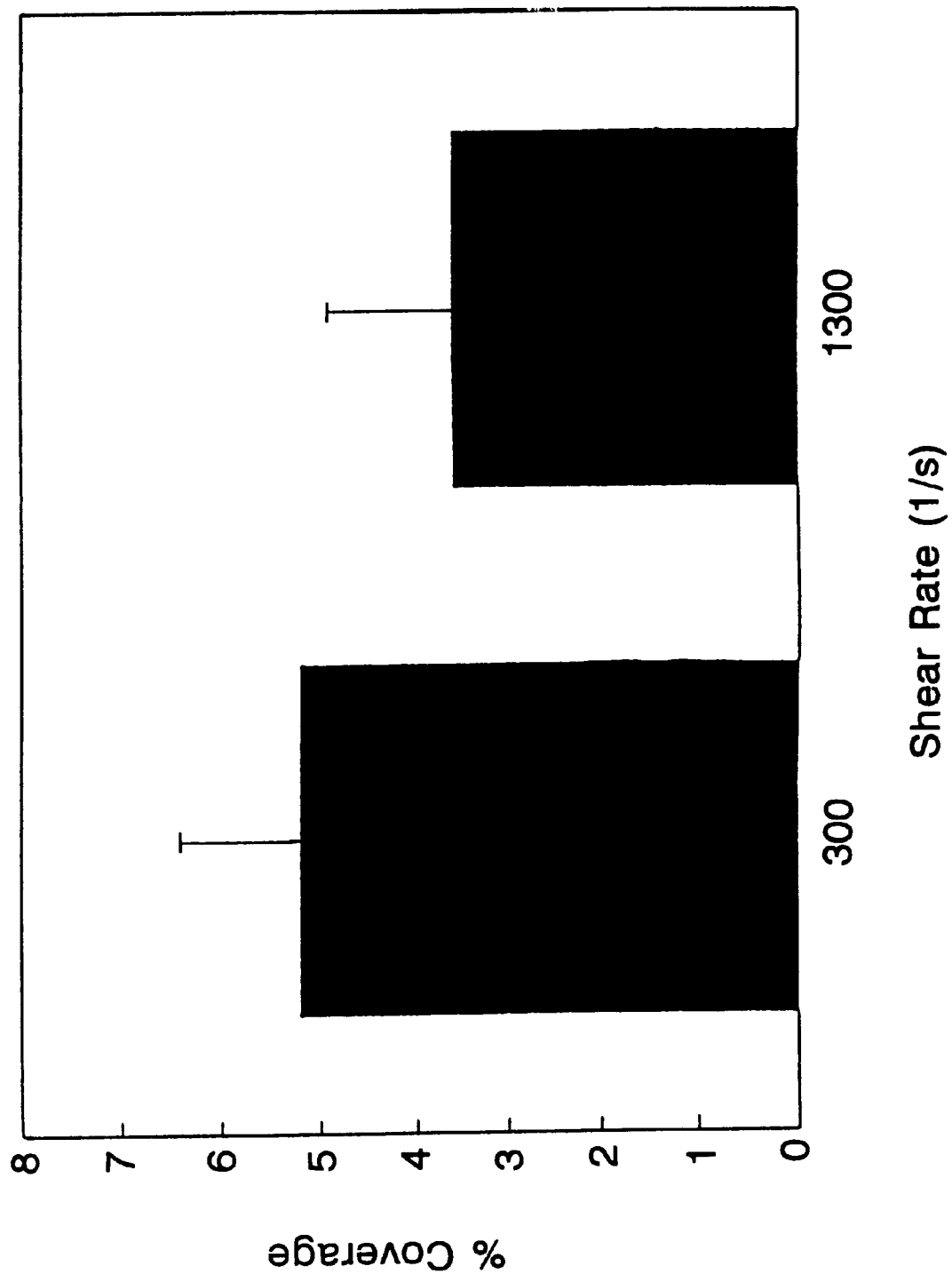

FIG. 25: Platelet Adhesion to VCL

VCL was also tested as a substrate in the model described in Example 9. Binding of platelets is low at both low and high shear rates ($\leq 5\%$ coverage).

DETAILED DESCRIPTION OF THE INVENTION

The plasmids pvWF-VC3, pvWF-VCL and pvWF-VA1 were deposited in *Escherichia coli* pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 68241, 68242 and 68530, respectively.

This invention provides a non-glycosylated, biologically active polypeptide having the amino acid sequence:

X-A-[Cys Ser Arg Leu Leu Asp Leu Val Phe Leu Leu Asp Gly Ser Ser Arg Leu Ser Glu Ala Glu Phe Glu Val Leu Lys Ala Phe Val Val Asp Met Met Glu Arg Leu Arg Ile Ser Gln Lys Trp Val Arg Val Ala Val Val Glu Tyr His Asp Gly Ser His Ala Tyr Ile Gly Leu Lys Asp Arg Lys Arg Pro Ser Glu Leu Arg Arg Ile Ala Ser Gln Val Lys Tyr Ala Gly Ser Gln Val Ala Ser Thr Ser Glu Val Leu Lys Tyr Thr Leu Phe Gln Ile Phe Ser Lys Ile Asp Arg Pro Glu Ala Ser Arg Ile Ala Leu Leu Leu Met Ala Ser Gln Glu Pro Gln Arg Met Ser Arg Asn Phe Val Arg Tyr Val Gln Gly Leu Lys Lys Lys Lys Val Ile Val Ile Pro Val Gly Ile Gly Pro His Ala Asn Leu Lys Gln Ile Arg Leu Ile Glu Lys Gln Ala Pro Glu Asn Lys Ala Phe Val Leu Ser Ser Val Asp Glu Leu Glu Gln Gln Arg Asp Glu Ile Val Ser Tyr Leu Cys](SEQ ID NO. 1)-B-COOH wherein X is NH$_2$-methionine- or NH$_2$-;

A is a sequence of at least 1, but less than 35 amino acids, which sequence is present in naturally occurring human vWF, the carboxy terminal amino acid of which is the tyrosine #508 shown in FIG. 12 (SEQ ID NO. 2);

B is a sequence of at least 1, but less than 211 amino acids, which sequence is present in naturally occurring human vWF, the amino terminal amino acid of which is the aspartic acid #696 shown in FIG. 12 (SEQ ID NO:2); and the two cysteines included within the bracketed sequence are joined by a disulfide bond. The bracketed sequence comprises amino acids #509–#695 of FIG. 12 (SEQ ID NO:2).

In one embodiment, this polypeptide has the amino acid sequence:

X-[Leu His Asp Phe Tyr Cys Ser Arg Leu Leu Asp Leu Val Phe Leu Leu Asp Gly Ser Ser Arg Leu Ser Glu Ala Glu Phe Glu Val Leu Lys Ala Phe Val Val Asp Met Met Glu Arg Leu Arg Ile Ser Gln Lys Trp Val Arg Val Ala Val Val Glu Tyr His Asp Gly Ser His Ala Tyr Ile Gly Leu Lys Asp Arg Lys Arg Pro Ser Glu Leu Arg Arg Ile Ala Ser Gln Val Lys Tyr Ala Gly Ser Gln Val Ala Ser Thr Ser Glu Val Leu Lys Tyr Thr Leu Phe Gln Ile Phe Ser Lys Ile Asp Arg Pro Glu Ala Ser Arg Ile Ala Leu Leu Leu Met Ala Ser Gln Glu Pro Gln Arg Met Ser Arg Asn Phe Val Arg Tyr Val Gln Gly Leu Lys Lys Lys Lys Val Ile Val Ile Pro Val Gly Ile Gly Pro His Ala Asn Leu Lys Gln Ile Arg Leu Ile Glu Lys Gln Ala Pro Glu Asn Lys Ala Phe Val Leu Ser Ser Val Asp Glu Leu Glu Gln Gln Arg Asp Glu Ile Val Ser Tyr Leu Cys Asp Leu Ala Pro Glu Ala Pro Pro Pro Thr Leu Pro Pro Asp Met Ala Gln Val Thr Val Gly Pro Gly Leu Leu Gly Val Ser Thr Leu Gly Pro Lys](SEQ ID NO. 5)-COOH wherein X is NH$_2$- or NH$_2$-methionine-, preferably NH$_2$-methionine-.

The bracketed sequence comprises amino acids #504–#728 of FIG. 12 (SEQ ID NO. 2).

One skilled in the art to which the subject invention pertains can readily make such polypeptides using recombinant or non-recombinant DNA techniques.

The polypeptides may be constructed using recombinant DNA technology. One means for obtaining the polypeptides is to express nucleic acid encoding the polypeptides in a suitable host, such as a bacterial, yeast, or mammalian cell, using methods well known in the art, and recovering the polypeptide after it has been expressed in such a host.

Examples of vectors that may be used to express the nucleic acid encoding the polypeptides are viruses such as bacteriophages (such as phage lambda), cosmids, plasmids, and other recombination vectors. Nucleic acid molecules are inserted into vector genomes by methods well known in the art. For example, using conventional restriction enzyme sites, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

Vectors comprising nucleic acid encoding the polypeptides may be adapted for expression in a bacterial cell, a yeast cell, or a mammalian cell which additionally comprise the regulatory elements necessary for expression of the nucleic acid in the bacterial, yeast, or mammalian cells so located relative to the nucleic acid encoding the polypeptide as to permit expression thereof. Regulatory elements required for expression include promoter sequences to bind RNA polymerase and transcription initiation sequences for ribosome binding.

For example, a bacterial expression vector may include a promoter such as the $\lambda$ P$_L$ or deo promoters and for transcription initiation the C$_{11}$ or deo ribosomal binding sites. Such vectors may be obtained commercially or assembled from the sequences described by methods well known in the art, for example the methods described above for constructing vectors in general.

In addition, non-recombinant techniques such as chemical synthesis, synthetic DNA or cDNA may be used to obtain the above-described polypeptides. One means of isolating the polypeptide is to probe a human genomic library with a natural or artificially designed DNA probe, using methods well known in the art. DNA and cDNA molecules which encode the polypeptides may be used to obtain complementary genomic DNA, cDNA or RNA from human, mammalian or other animal sources, or to isolate related cDNA or genomic clones by the screening of cDNA or genomic libraries.

The subject invention further provides a pharmaceutical composition comprising an amount of any of the above-described polypeptides effective to inhibit platelet aggregation and a pharmaceutically acceptable carrier.

As used herein, the term "pharmaceutically acceptable carrier" encompasses any of the standard pharmaceutical carriers. Such carriers are well known in the art and may include, but are in no way and are not intended to be limited to, any of the standard pharmaceutical carriers such as phosphate buffered saline solutions, water, emulsions such as oil/water emulsion, and various types of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The composition has an amount sufficient to result in a blood concentration of 0.06 to 58 $\mu$M, preferably between about 0.06 and 29 $\mu$M, for example 0.23 to 23 $\mu$M. Expressed in different terms, the amount should be 0.1 to 100 mg/Kg body weight, preferably 0.1 to 50 mg/Kg body weight, for example 0.4 to 40 mg/kG body weight.

The administration of the composition may be effected by any of the well known methods, including but not limited to intravenous, intramuscular, subcutaneous and oral administration.

This invention also provides a method of inhibiting platelet aggregation which comprises contacting platelets with an amount of any of the above-described polypeptides effective to inhibit platelet aggregation so as to inhibit platelet aggregation. The range of the amount effective to inhibit platelet aggregation is 0.1–200 mg/kg body weight, preferably 1–20 mg/kg body weight. The amount effective to inhibit platelet aggregation is an amount sufficient to maintain a blood concentration of 0.1–10 $\mu$M polypeptide. In a preferred embodiment, the blood concentration is maintained at about 1 $\mu$M polypeptide.

This invention also provides expression plasmids encoding the above-described polypeptides. In one embodiment, the expression plasmid encoding the polypeptide with the bracketed sequence, i.e. amino acids #504–#728 of FIG. 12, is designated pvWF-VC3 and is deposited under ATCC Accession No. 68241. In another embodiment, the expression plasmid encoding a polypeptide with the bracketed sequence, i.e. amino acids #504–#728 of FIG. 12 (SEQ ID NO. 2), is designated pvWF-VCL and is deposited under ATCC Accession No. 68242.

The expression plasmids of this invention further comprise suitable regulatory elements positioned within the plasmid relative to the DNA encoding the polypeptide so as to effect expression of the polypeptide in a suitable host cell, such as promoter and operators, e.g. deo $P_1P_2$ and $\lambda$ $P_LO_L$, ribosomal binding sites, e.g. deo and $C_{11}$, and repressors. Other suitable regulatory elements include, for example, the lac, trp, tac, and lpp promoters (European Patent Application Publication No. 0303972, published Feb. 22, 1989).

The suitable regulatory elements are positioned within the plasmid relative to the DNA encoding the polypeptide so as to effect expression of the polypeptide in a suitable host cell. In preferred embodiments of the invention, the regulatory elements are positioned close to and upstream of the DNA-encoding the polypeptide.

The expression plasmids of this invention may be introduced into suitable host cells, preferably bacterial host cells. Preferred bacterial host cells are *Escherichia coli* cells. Examples of suitable *Escherichia coli* cells are strains S$\phi$930 or 4300, but other *Escherichia coli* strains and other bacteria can also be used as host cells for the plasmids. Such bacteria include *Pseudomonas aeruginosa* and *Bacillus subtilis*.

The bacteria used as hosts may be any strain including auxotrophic (such as A1645), prototrophic (such as A4255), and lytic strains; $F^+$ and $F^-$ strains; strains harboring the $CI^{857}$ repressor sequence of the $\lambda$ prophage (such as A1645 and A4255); and strains deleted for the deo repressors and the deo gene (see European Patent Application Publication No. 0303972, published Feb. 22, 1989). *Escherichia coli* strain A4255 ($F^+$) has been deposited under ATCC Accession No. 53468, and *Escherichia coli* strain A1645 has been deposited under ATCC Accession No. 67829.

The invention provides a bacterial cell which comprises these expression plasmids. In one embodiment, the bacterial cell is an *Escherichia coli* cell. In preferred embodiments, the invention provides an *Escherichia coli* cell containing the plasmid designated pvWF-VA1, deposited in *E. coli* strain S$\phi$930 with the ATCC under ATCC Accession No. 68530; pvWF-VA3; pvWF-VB3; pvWF-VC3, deposited in *E. coli* strain S$\phi$930 with the ATCC under ATCC Accession No. 68241; pvWF-VD3; or pvWF-VCL, deposited in *E. coli* strain 4300($F^-$) with the ATCC under ATCC Accession No. 68242.

All the *E. coli* host strains described above can be "cured" of the plasmids they harbor by methods well-known in the art, e.g. the ethidium bromide method described by R. P. Novick in *Bacteriol. Review* 33, 210 (1969).

In addition, the subject invention provides a method of producing any of the above-described polypeptides which comprises transforming a bacterial cell with an expression plasmid encoding the polypeptide, culturing the resulting bacterial cell so that the cell produces the polypeptide encoded by the plasmid, and recovering the polypeptide so produced.

Furthermore, the invention provides a method of treating a subject with a cerebrovascular disorder which comprises administering to the subject an amount of any of the polypeptides of the invention effective to inhibit platelet aggregation.

Also provided is a method of treating a subject with a cardiovascular disorder which comprises administering to the subject an amount of a polypeptide effective to inhibit platelet aggregation. Examples of cardiovascular disorders susceptible to treatment include acute myocardial infarction or angina.

Further, the subject invention provides method of inhibiting platelet aggregation in a subject prior to, during, or after the subject has undergone angioplasty, thrombolytic treatment, or coronary bypass surgery which comprises administering to the subject an amount of a polypeptide of the invention effective to inhibit platelet aggregation.

The invention also provides a method of maintaining blood vessel patency in a subject prior to, during, or after the subject has undergone coronary bypass surgery, which comprises administering to the subject an amount of a polypeptide of the invention effective to inhibit platelet aggregation.

The invention also provides a method of treating a subject having cancer which comprises administering to the subject an amount of a polypeptide of the invention effective to retard tumor metastasis.

The invention also provides a method of inhibiting thrombosis in a subject which comprises administering to the subject an amount of a polypeptide of the invention effective to inhibit the thrombosis. The thrombosis may be associated with an inflammatory response.

In addition, the subject invention provides a polypeptide of the invention bound to a solid matrix.

The invention also provides a method of treating a subject suffering from platelet adhesion to damaged vascular surfaces which comprises administering to the subject an amount of the polypeptide of the invention effective to inhibit platelet adhesion to damaged vascular surfaces. The range of the amount effective to inhibit platelet adhesion is 0.1–200 mg/kg body weight, preferably 1–20 mg/kg body weight. The amount effective to inhibit platelet adhesion is the amount sufficient to maintain a blood concentration of 0.1–10 μM polypeptide. In a preferred embodiment, the blood concentration is maintained at about 1 μM polypeptide.

The invention also provides a method of preventing platelet adhesion to a prosthetic material or device in a subject which comprises administering to the subject an amount of the polypeptide of the invention effective to prevent platelet adhesion to the material or device.

The invention also provides a method of inhibiting re-occlusion in a subject following angioplasty or thrombolysis which comprises administering to the subject an amount of the polypeptide of the invention effective to inhibit re-occlusion.

The invention also provides a method of preventing vaso-occlusive crises in a subject suffering from sickle cell anemia which comprises administering to the subject an amount of the polypeptide of the invention effective to prevent vaso-occlusive crises.

The invention also provides a method of preventing arteriosclerosis in a subject which comprises administering to the subject an amount of the polypeptide of the invention effective to prevent arteriosclerosis.

The invention also provides a method of thrombolytic treatment of thrombi-containing, platelet-rich aggregates in a subject which comprises administering to the subject an amount of the polypeptide of the invention effective to treat thrombi-containing, platelet-rich aggregates.

The invention also provides a method of preventing platelet activation and thrombus formation due to high shear forces in a subject suffering from stenosed or partially obstructed arteries which comprises administering to the subject an amount of the polypeptide of the invention effective to prevent platelet activation and thrombus formation.

The invention also provides a method of preventing thrombin-induced platelet activation in a subject which comprises administering to the subject an amount of the polypeptide of the invention effective to prevent thrombin-induced platelet activation.

The invention also provides a method of preventing stenosis as a result of smooth muscle proliferation following vascular injury in a subject which comprises administering to the subject an amount of the polypeptide of the invention effective to prevent stenosis.

The invention also provides a method for recovering a purified, biologically active polypeptide of the invention which comprises:

(a) producing in a bacterial cell a first polypeptide having the amino acid sequence of the polypeptide but lacking the disulfide bond;

(b) disrupting the bacterial cell so as to produce a lysate containing the first polypeptide;

(c) treating the lysate so as to obtain inclusion bodies containing the first polypeptide;

(d) contacting the inclusion bodies from step (c) so as to obtain the first polypeptide in soluble form;

(e) treating the resulting first polypeptide so as to form the biologically active polypeptide;

(f) recovering the biologically active polypeptide so formed; and (g) purifying the biologically active polypeptide so recovered.

Step (e) may comprise contacting the polypeptide with a thiol-containing compound and disulfide so as to refold and reoxidize the polypeptide. Preferably, the thiol-containing compound is glutathione, thioredoxin, β-mercaptoethanol or cysteine.

The contacting of step (d) may be effected in the presence of a denaturant such as guanidine hydrochloride or urea.

The recovery of the polypeptide in step (f) may comprise removing the denaturant by dialysis.

In step (g), the biologically active polypeptide may be purified by cation exchange chromatography.

The first polypeptide may also be purified by cation exchange chromatography after step (d).

The invention also provides a method for treating a subject suffering from von Willebrand Disease type IIb which comprises administering to the subject an amount of the polypeptide of the invention effective to prevent binding of platelets to plasma vWF. Plasma vWF does not normally bind platelet GPIb in the circulation. GPIb binds to vWF only in the presence of an inducer such as ristocetin or botrocetin, or if the vWF is immobilized. Patients suffering from von Willebrand Disease type IIb (vWDIIb) have a mutant vWF which spontaneously binds platelet GPIb in the circulation, causing thrombocytopenia and a resultant bleeding disorder due to the lack of platelets.

The examples which follow are set forth to aid in understanding the invention but are not intended to, and should not be so construed as to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well-known to those skilled in the art and are described in numerous publications including Sambrook, Fritsch and Maniatis, *Molecular Cloning: A Laboratory Manual,* 2nd Edition, Cold Spring Harbor Laboratory Press, USA, (1989).

EXAMPLES

All the references to map positions correspond to the identically numbered positions along the translated nucleotide sequence of mature human von Willebrand Factor shown in FIG. 12 (SEQ ID NO. 2).

Example 1

Cloning and Expression of vWF GP1b Binding Domain Polypeptides

CDNA Cloning of Human vWF GP1b Binding Domain

A human endothelial cDNA library (obtained from CLONTECH Laboratories, Inc.) in λ gt11 was screened for human vWF positive sequences using two synthetic DNA probes. The probes were synthesized according to the published DNA sequence (Sadler et al., Proc. Nat. Acad. Sci. 82: 6394–8 (1985) and Verweij et al., EMBO J. 3: 1829–47 (1986)) of human vWF (flanking 5' end and 3' end of the vWF domain known to bind the GPIb receptor) (see FIG. 12).

The synthetic probes have the following sequences:

| Sequence | | Nucleotides |
|---|---|---|
| AAATCTGGCAGTGCTCAGGGTCACTGGGATTCAAGGTGAC | (SEQ ID NO:6) | 3863–3902 |
| CCAGGACGAACGCCACATCCAGAACCATGGAGTTCCTCTT | (SEQ ID NO:7) | 4700–4739 |

Figure 1:
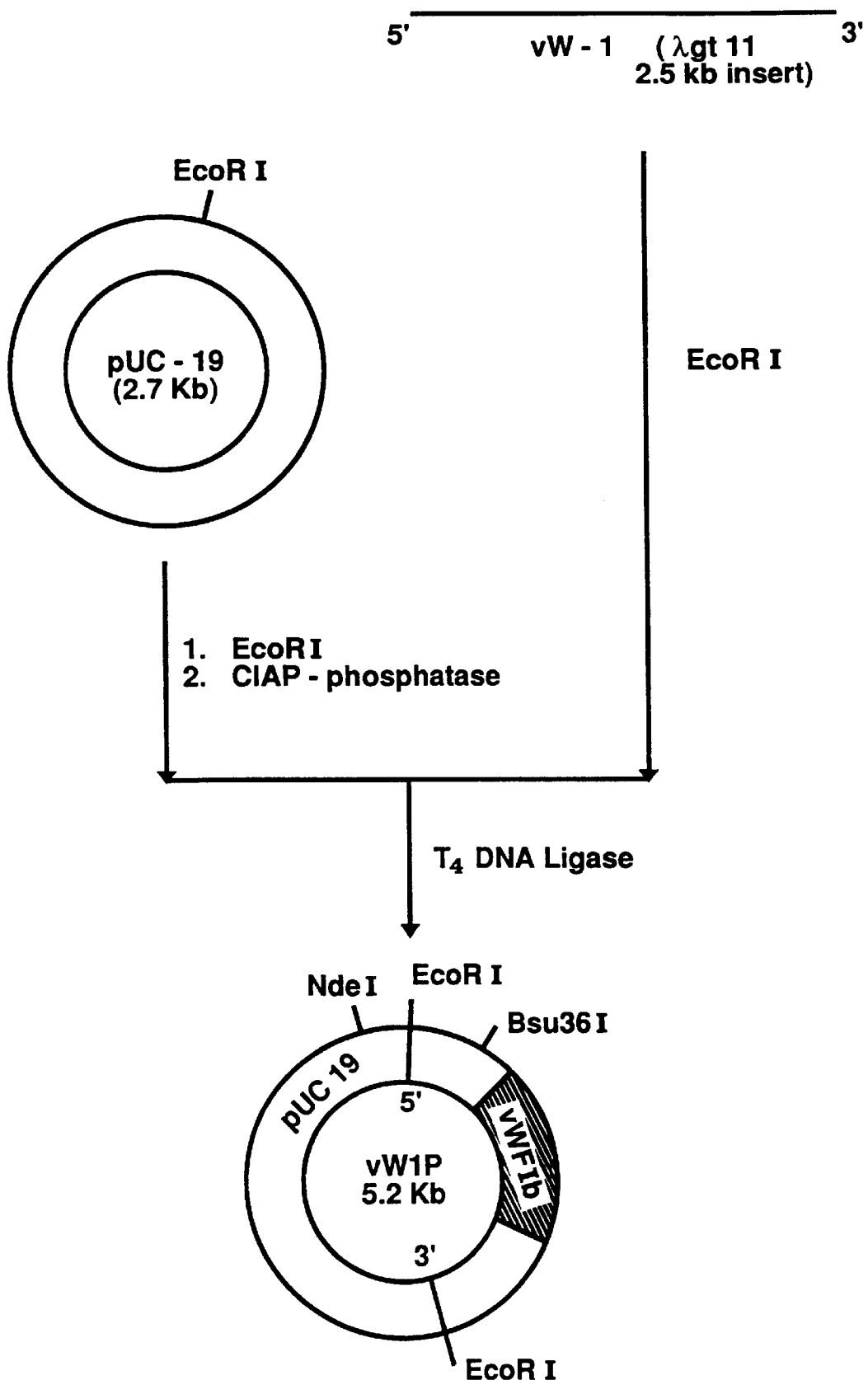
FIG. 1: Construction of pvW1P

A series of vWF CDNA clones covering the entire GPIb binding domain were identified and isolated. The CDNA fragments were subcloned into EcoRI site of pUC-19 (New England Biolabs, Inc.). One of the subclones, designated pvW1P (FIG. 1), contains a 2.5 Kb insert. This 2.5 Kb insert covers the entire GPIb binding domain extending from 550 bp upstream of the GPIb binding site to 1100 bp downstream of the GPIb binding site. (The subclone pvW1P has also been designated pvWF-1P).

Manipulation of DNA Coding for the vWF GPIb Binding Domain

In order to obtain expression of the GPIb binding domain in *Escherichia coli* under the regulation of the deo $P_1P_2$ promoter, the cDNA fragment of vWF, derived from plasmid pvW1P was used for further manipulations as described below. As indicated previously, the vWF tryptic digest fragment that binds the GPIb receptor is from amino acid Val 449 to amino acid Lys 728.

A. Subcloning of the 5' end of vWF GPIb binding domain and addition of a translation initiation codon ATG.

Plasmid pvW1P has two convenient restriction sites at the 5' end. Bsu36I which cuts at the DNA sequence corresponding to amino acid Ser (445), and Tth111I which cuts at amino acid Asp (514). Synthetic fragments of various size were designed that insert an ATG translation initiation codon at the 5' end as well as additional amino acids. This was done first, in order to maximize the chances of obtaining high levels of expression. Second, they are a first step towards reducing the size of the vWF GPIb binding domain peptide down to the minimal size needed, possibly eliminating collagen and heparin binding sites which may ultimately interfere with the function of the product.

A1. Amino acid Glu 437 at 5' end
    Synthetic oligomers with the sequences:

```
                                         (SEQ ID NO:8)
5' - TATGGAGGTGGCTGGCCGGCGTTTTGCC - 3'

(SEQ ID NO:9)
3' -    ACCTCCACCGACCGGCCGCAAAACGGAGT - 5'
     NdeI                        Bsu36I
``` were ligated to plasmid pvWF-1P digested with NdeI and Bsu36I (see FIG. 2). The plasmid obtained was designated pvWF-VA1. Plasmid pvWF-VA1 has been maintained in *E. coli* strain Sϕ930 and was deposited under ATCC Accession No. 68530.

A2. Amino acid Phe 443 at 5' end
    Synthetic oligomers with the sequences:
      5'-TATGTTTGCC-3' (SEQ ID NO:10)
        3'-ACAAACGGAGT-5' (SEQ ID NO:11)

```
5' - TATGTTGCACGATTTCTACTGCAGCAGGCTACTGGACC - 3'   (SEQ ID NO:16)

3' -  ACAACGTGCTAAAGATGACGTCGTCCGATGACCTGGA - 5'   (SEQ ID NO:17)
      NdeI                                Tth111I
``` were ligated to plasmid pvW1P digested with NdeI and Bsu36I (see FIG. 3 (SEQ ID NO:10 and SEQ ID NO:11)). The plasmid obtained was designated pvWF-VB1.

B. Subcloning of the 3' end of vWF GPIb binding domain, introduction of translation stop codon.

B1. Introduction of stop codon in plasmid pvWF-VA1
    A syn thetic oligomer with the sequence:
5'-CCGGGGCTCTTGGGGGTTTCGACCCTGGGGCC CAAG<u>TAA</u>GATATCA-3' (SEQ ID NO:12)
3'-CCGAGAACCCCCAAAGCTGGGACCCCGGGT TCATTCTATAGTTCGA-5' (SEQ ID NO:13)
    was ligated to an XmaI and HindIII digested plasmid pvWF-VA1 (see FIG. 4 (SEQ ID NO:12 and SEQ ID NO:13)). The plasmid obtained was designated pvWF-VA2. This newly constructed plasmid contains a translation termination codon TAA adjacent to amino acid 728 (Lys) and ECORV site.

B2. Introduction of translation sto codon in plasmid pvWF-VB1
    A synthetic oligomer with the sequence:
5'-CCGGGGCTCTTGGGGTTTCGACCCTGGGGCCC AAG<u>TAA</u>GATATCA-3' (SEQ ID NO:14)
3'-CCGAGAACCCCAAAGCTGGGACCCCGGGTT CATTCTATAGTTCGA-5' (SEQ ID NO:15)
    was ligated to plasmid pvWF-VB1 digested with XmaI and HindIII. The plasmid obtained was designated pvWF-VB2 (see FIG. 5(SEQ ID NO:14 and SEQ ID NO:15)).

Expression of the VWF GPIb binding domain in *Escherichia coli*

In order to obtain expression of the vWF GPIb binding domain various expression plasmids were constructed based on a deo $P_1P_2$ constitutive promoter system.

1. Expression of a vWF GPIb binding domain polyeptide including amino acid Glu 437 to amino acid Lys 728 (based on plasmid pvWF-VA2)

An NdeI-EcoRV fragment was isolated from plasmid pvWF-VA2 and ligated into plasmid pMF-945 (see FIG. 11) digested with NdeI and PvuII (see FIG. 6). The plasmid obtained was designated as pvWF-VA3 and was maintained in *Escherichia coli* strain Sϕ930.

2. Expression of a vWF GPIb binding domain polupeptide including amino acid Phe 443 to amino acid Lys 728 (based on plasmid pvWF-VB2)

An NdeI-EcoRV fragment was isolated from plasmid pvWF-VB2 and ligated into plasmid pMF-945 digested with NdeI and PvuII (see FIG. 7). The plasmid obtained was designated as pvWF-VB3 and was maintained in *Escherichia coli* strain Sϕ930.

3. Expression of a vWF GPIb binding domain polypeptide including amino acid Leu 504 to amino acid Lys 728 (based on expression plasmid pvWF-VA3)
    A synthetic oligomer with the sequence:

was ligated to plasmid pvWF-VA3 digested with NdeI and Tth111I. The plasmid obtained was designated as pvWF-VC3 (see FIG. 8(SEQ ID NO:16 and SEQ ID NO:17). Plasmid pvWF-VC3 is maintained in *Escherichia coli* strain Sϕ930 and has been deposited with the ATCC under Accession No. 68241 (also see FIG. 13 (SEQ ID NO:18).

4. Expression of a vWF GPIb binding domain polypeptide including amino acid Leu 513 to amino acid Lys 728 (based on expression plasmid pvWF-VA3)

A synthetic oligomer with the sequence:

```
5' - TATGCTGGACC - 3'

3' -   ACGACCTGGA - 5'
     NdeI    Tth111I
``` was ligated to plasmid pvWF-VA3 digested with NdeI and Tth111I. The plasmid obtained was designated pvWF-VD3 (see FIG. 9(SEQ ID NO:19 and SEQ ID NO:20). Plasmid pvWF-VD3 is maintained in *Escherichia coli* strain Sφ930.

Expression of vWF-GPIb binding domain polypeptides

The relative alignment of the expression plasmids is shown in FIG. 10. Plasmids pvWF-VA3, pvWF-VB3, pvWF-VC3 and pvWF-VD3 in *Escherichia coli* strain Sφ930 were used in order to analyze the levels of expression of the various vWF-GPIb binding domain peptides. The clones obtained were grown in LB medium containing Amp (100 μg/ml) at 37° C. for 48 hours.

After 48 hours growth bacterial cells were harvested and centrifuged for 2 minutes at 10,000 RPM. Pellets were dissolved in 1/10 volume of 50 mM Tris-HCl pH=8.0. Sample buffer (containing SDS and β-mercaptoethanol) was added. Samples were boiled for 10 minutes and loaded on a 10% SDS polyacrylamide gel. The expression of the vWF GPIb binding domain polypeptides in clones pvWF-VA3, pvWF-VB3 and pvWF-VD3 was low relative to the bacterial total proteins. The vWF polypeptides from these clones were detectable by Western blot analysis using commercially available polyclonal vWF antibody (Dekopatts a/s, Glostrup, Denmark). However, clones originated from *Escherichia coli* strain Sφ930 transformed with plasmid pvWF-VC3 expressed the vWF GPIb binding domain polypeptide (amino acid Leu 504 to amino acid Lys 728 plus methionine) at high levels (as a major band) detectable upon Coomassie staining.

*Escherichia coli* strain Sφ930 harboring plasmid pvWF-VC3 was deposited with the ATCC under Accession No. 68241. Subsequently, an inducible plasmid was constructed which contains the same vWF coding region as pvWF-VC3, expressed under the control of the λ P$_L$ promoter and the deo ribosomal binding site (see FIG. 14). This new plasmid, designated pvWF-VCL, proved to be a high expressor of VCL, the vWF GPIb binding domain polypeptide (methionine plus amino acid Leu 504 to amino acid Lys 728). This plasmid was deposited in *Escherichia coli* strain 4300 with the ATCC under Accession No. 68242. *Escherichia coli* strain 4300, constructed from *Escherichia coli* strain ATCC Accession No. 12435, is a wild-type, F⁻, biotin dependent strain, harboring the λ cI857 temperature-sensitive repressor. (A third plasmid construct harboring the same vWF coding region under the control of the λ promoter and the cII ribosomal binding site did not express any vWF peptide detectable by Coomassie staining.)

The NdeI-HindIII insert of pvWF-VCL can be conveniently subcloned into other expression vectors such as commercially available pUC19 for production of a series of polypeptides which include the same amino acid sequence from amino acid 509 (cys) to amino acid 695 (cys) and have the same biological activity.

Example 2

Fermentation of Bacteria Expressing vWF GPIb Binding Domain Polypeptides

During scale-up fermentations of clone pvWF-VC3 it was found that the host tends to lose the plasmid due to instability. The loss of plasmids caused a reduction in vWF GPIb binding domain polypeptide expression. It was found necessary to maintain continuous selective pressure (i.e., continuous addition of Ampicillin) in order to maintain plasmid copy number and to maintain the expression levels. Large scale fermentation was carried out for 12 hours.

Fermentation was carried out in the following growth medium:

| | |
|---|---|
| N-Z amino AS | 20 gr |
| Yeast extract | 10 gr |
| NaCl | 5 gr |
| K$_2$HPO$_4$ | 2.5 gr |
| MgSO$_4$7H$_2$O | 1.0 gr |
| Anti foam | 0.4 ml |

Fructose (50%) was added to the growth medium at final concentration of 150 ml/liter and Ampicillin (100 mg/ml) was pumped continuously into the fermentor (total of 8 ml/liter). Fermentation was carried out for 12 hours at 37° C.

Purification of polypeptides

Cells were harvested after 12 hours fermentation and centrifuged. The bacterial pellet obtained was resuspended in buffer [50 mM Tris pH=8.0, 50 mM NaCl, 1 mM EDTA, 1 mM DTT (dithiothreitol), 1 mM PMSF (Phenylmethylsulfonyl fluoride) and 10% Glycerol]. After additional centrifugation and sonication the vWF GPIb binding domain polypeptide was found in the pellet.

The vWF GPIb binding domain polypeptide was further purified by solubilization of the pellet in 8M Urea containing 10 mM DTT, 25 mM Tris pH=8 and 1 mM EDTA at room temperature. The solubilized pellet was fractionated on a DEAE cellulose ion exchange column chromatography. (Elution buffer as above except 0.5 mM DTT).

The vWF GPIb binding domain polypeptide was eluted at 150 mM NaCl. After dilution to 50 mM NaCl (in the above buffer) the partially purified peptide was loaded on a Q-Sepharose column. Elution from the Q-Sepharose column was carried out at various NaCl concentrations (step elution). The vWF GPIb binding domain peptide was pooled in four peaks which eluted at 100 mM, 200 mM, 250 mM and 500 mM NaCl. All four peaks were dialyzed against 150 mM NaCl and 50 mM Tris pH=8 for 36 hours. During the dialysis the Urea concentration of the dialysis solution was reduced in a linear gradient from 6M Urea to no Urea.

Example 3

Biological Activity of vWF GPIb Binding Domain Polypeptides

Platelet Aggregation Assays vWF preparation:

Human plasma-derived vWF was purified from human outdated blood bank plasma according to J. Loscalzo and R. I. Handin, Biochemistry 23: 3880–3886 (1984). The purified plasma-derived vWF was concentrated by Amicon 100,000 cut-off filter membrane, to a final concentration of 0.25 mg/ml.

Asialo-vWF preparation:

The purified plasma-derived human vWF was desialyated according to L. DeMarco and S. Shapiro, J. Clin. Invst. 68: 321–328 (1981) with the following modifications:

1. The Neuraminidase used was from *Vibrio cholera* type II (Sigma).
2. The reaction mixture contained 0.2 Units enzyme/mg protein and protease inhibitors according to the following concentrations: Benzamidine (20 mM), Leupeptin (15 μg/ml) and Aprotinin 20 (U/ml). The asialo-vWF was used for platelet aggregation without any further purification.

Platelet aggregation—Induced by Asialo-vWF

As stated above, soluble vWF does not bind to platelets via the GPIb receptor. Asialo-vWF, obtained by neuraminidase treatment to remove sialic acid residues, readily binds to platelets via GPIb. Presumably, the desialation lowers the net negative charge on the vWF, allowing it to bind to the negatively charged GPIb receptor. Asialo-vWF binding to platelets causes activation, release of ADP, and GP IIb/IIIa mediated aggregation. Platelet aggregation induced by asialo-vWF was carried out with 200 μl of PRP (Platelet-rich plasma) (Fujimura Y., et al., J. Biol. Chem. 261: 381–385 (1986)) and 39 μg/ml of asialo-vWF (final concentration) in a Lumi aggregometer. The results of inhibition of platelet aggregation with VC, the vWF GPIb binding domain polypeptide, are summarized in Table I.

VC (also referred to as VCL or VC3) is a vWF GPIb binding domain polypeptide which includes methionine plus amino acids 504–728 (see FIG. 12 (SEQ ID NO:2)).

vWF-Ristocetin induced platelet aggregation

Ristocetin-induced platelet aggregation in the presence of purified human intact vWF was carried out with washed human platelets according to Fujimura Y. et al., J. Biol. Chem. 261: 381–385 (1986).

The results of inhibition of platelet aggregation induced by ristocetin in the presence of intact vWF are summarized in Table II. Additional results using these assays are described in Example 5.

TABLE I

Inhibition of Asialo-vWF Induced Platelet Aggregation (In PRP) by VC, a vWF GPIb Binding Domain Polypeptide

| Q-Sepharose Fraction | vC concentration μM | % Inhibition of Platelet Aggregation | |
|---|---|---|---|
| 200 mM NaCl | 6 | 76 | 64 |
| 250 mM NaCl | 6 | 82 | 73 |
| 500 mM NaCl | 6 | 89 | 79 |

TABLE II

Inhibition of Ristocetin Induced Platelet Aggregation by VC, a vWF GPIb Binding Domain Polypeptide

| Q-Sepharose Fraction | vC concentration in μM | % Inhibition of Platelet Aggregation |
|---|---|---|
| 200 mM NaCl | 10 | 76 |
|  | 6 | 69 |
|  | 3 | 38 |
|  | 1 | 22 |
| 250 mM NaCl | 10 | 86 |
|  | 6 | 67 |
|  | 3 | 44 |
|  | 1 | 34 |
| 500 mM NaCl | 10 | 100 |
|  | 6 | 79 |
|  | 3 | 68 |
|  | 1 | 54 |
|  | 0.25 | 38 |
| Dialysis Buffer (control) | 0 | 0 |

Example 4

An Improved Method of Obtaining Pure, Oxidized, Folded and Biologically Active vWF GPIb Binding Domain Polypeptide In Example 2, fermentation of cells harboring plasmid pvWF-VC3 was described. Subsequently, a preferred plasmid, pvWF-VCL was constructed as described in Example 1 and maintained in E.coli strain A4300. This host/plasmid system was fermented essentially as known in the art for vectors containing a gene expressed under control of the $\lambda P_L$ promoter, see, for example coassigned EPO Patent Publication No. 173,280, published Mar. 5, 1986, Example 5, pages 73–74 (without added biotin, thiamine, trace elements, and ampicillin). In this improved method of purification of vWF GPIb binding domain polypeptide, a cell pellet of the above fermentation of A4300/pvWF-VCL was used.

In this improved method a purer and more active polypeptide is produced than by the method disclosed in Example 2. the general scheme of the downstream process consists of steps A through H as follows:

A. Cell disruption and suspension of oellet: A pellet containing the vWF GPIb binding domain polypeptide is obtained as described in Example 2, by sonication and centrifugation of a cell suspension in 50 mM Tris-HCl pH=8, 50 mM, NaCl, 1 mM EDTA, 1 mM DTT, 1 mM PMSF, and 10% Glycerol.

The pellet containing the inclusion bodies is dissolved at about 10% w/v in a solution such that the final concentrations after dissolution are 8M urea, 20 mM DTT, 20 mM HEPES pH 8, and 100 mM NaCl. The resulting solution may be further purified by ion exchange chromatography as described below. Alternatively, the inclusion bodies may be solubilized in a buffer containing 6M guanidine hydrochloride followed by buffer exchange to urea. The inclusion bodies may also be dissolved at different concentrations of urea, guanidine hydrochloride or any other denaturant or in the absence of denaturants, for example, at extremes of pH.

B. Cation exchange chromatography: This step eliminates most of the contaminants and produces the vWF GPIb binding domain polypeptide at greater than 90% purity. Any cation exchange (e.g. carboxymethyl) method may be used in this step, but CM-Sepharose fast flow (Pharmacia) chromatography is preferred. The functional group may be carboxymethyl, a phospho group or sulphonic groups such as sulphopropyl. The matrix may be based on inorganic compounds, synthetic resins, polysaccharides, or organic polymers; possible matrices are agarose, cellulose, trisacryl, dextran, glass beads, oxirane acrylic beads, acrylamide, agarose/polyacrylamide copolymer (Ultrogel) or hydrophilic vinyl polymer (Fractogel). In a specific embodiment, the polypeptide is loaded onto a CM-Sepharose FF column equilibrated with 8M urea, 1 mM DTT, 20 mM HEPES pH 8, 100 mM NaCl. Pure polypeptide elutes in 8M urea, 1 mM DTT, 20 mM HEPES pH 8 and 20 mM NaCl. Up to about 30 $OD_{280}$ units of solubilized inclusion bodies may be loaded per ml CM-Sepharose FF. At this ratio the eluted polypeptide typically has a concentration of 4–5 $OD_{280}$/ml.

C. Oxidation/Refolding: The polypeptide solution eluted from the cation exchange step above is treated with 6M guanidine hydrochloride (GuCl) to disrupt any aggregates. The polypeptide is then diluted to 0.05 $OD_{280}$/ml in 2M GuCl, pH 5–11, preferably 20 mM HEPES pH 8, 0.1 mM GSSG (glutathione, oxidized form). This mixture is allowed to stand overnight at room temperature. The products are analyzed by gel filtration on fast protein liquid chromatography (FPLC) such as Superose 12 before proceeding. Analysis shows that this protein concentration reproducibly yields about 30% correctly oxidized monomers, and 70% S-linked dimers and multimers, as well as reduced and incorrectly oxidized monomers. A higher protein concentration gives a higher absolute yield of correctly oxidized monomers but a lower percentage yield due to increased formation of S-linked dimers and multimers. For example, a protein concentration of 0.1 $OD_{280}$/ml yields only 20% correctly oxidized monomers. Reducing the concentration to 0.025 $OD_{280}$/ml yields 35–40% correctly oxidized monomers but a lower absolute yield per liter oxidation. Oxidations may also be performed in urea instead of in GuCl, or in any other denaturant or in the absence of denaturants under appropriate buffer conditions in which, for example, pH, ionic strength, and hydrophobicity are varied. The preferred concentration of urea is in the range 0.5M to 10M, preferably 4M, and the preferred oxidant is GSSG in the range 0.01 mM to 5 mM preferably 0.1 mM. Other oxidants such as $CuCl_2$ may be used or alternatively no oxidant may be added, thereby utilizing air oxidation only. For scale-up, 4M urea is the presently preferred solution for the oxidation step.

D. Concentration: The oxidation products are concentrated, preferably to about $OD_{280}=1$ by a tangential flow ultrafiltration system with a 30K cutoff membrane, such as a "MINITAN" or "PELLICON" system of Millipore. The filtrate is quite clear as the material is relatively clean and most of the contaminants are large enough not to pass through the 30K membrane. It is thus possible to reuse the filtrate for performing oxidations. This results in considerable savings since large volumes of 2M GuCl are quite expensive. No difference in the oxidation products of oxidations performed in reused versus freshly prepared 2M GuCl was detectable by FPLC analysis.

E. Dialysis: It is necessary to reduce the GuCl or urea concentration to less than 10 mM. This is achieved by dialysis against 20 mM HEPES pH8, 100 mM NaCl. The dialysis was performed in dialysis tubing with 2–3 changes of buffer, but may be alternatively performed by diafiltration against the same buffer in a tangential flow ultrafiltration system with a 10K MW cutoff membrane.

During dialysis, as the concentration of GuCl (or urea or other denaturant) decreases, a white precipitate forms. This precipitate contains about 80% of the protein yielded by step D comprising S—S linked dimers, reduced and incorrectly oxidized monomer and some contaminants which coeluted from the cation exchange step. The supernatant is nearly 100% correctly oxidized and refolded monomer at a concentration of 0.2 $OD_{280}$ ml, which is about 20% of the protein yield of step D. This selective precipitation of contaminants and undesirable forms of the protein as a result of dialysis was surprising and not predictable. The yield of correctly oxidized monomer can be greatly increased by recovery from the precipitate. This is done as follows: the solution is clarified by centrifugation. The supernatant is saved, and the pellet is treated with DTT to reduce S—S bonds and reoxidized as described above. The pellet is dissolved in a minimal volume of 6M GuCl, 20 ml HEPES pH 8, 150 mM NaCl, 20 mM DTT. The solution was passed through Sephadex G25 in a buffer similar to the dissolution buffer but containing only 1 mM DTT (instead of 20 mM). The eluate is then diluted to $OD_{280}=0.05$ and treated as in steps C, D and E above. This procedure may be repeated more than once as long as additional purified monomer is obtained. All of the supernatants are then combined.

F. Cation exchange: The combined supernatant of the dialysate of step E is concentrated by binding to CM Sepharose in 20 mM HEPES pH8, 100 mM NaCl. Elution is with 20 mM HEPES pH8, 400 mM NaCl. The eluate is exclusively monomeric despite the high salt concentration. Concentrations of up to 3 mg/ml have been achieved by this method and that is not the upper limit. This step can alternatively be performed with Heparin-Sepharose which also binds the purified monomer in 10 mM Tris pH 7.4, 150 mM NaCl. Elution from Heparin-Sepharose is performed using 10 mM Tris-HCl pH 7.4, 500 mM NaCl.

G. Dialysis: The product of the previous step is dialyzed against 20 mM HEPES pH8, 150 mM NaCl.

H. Storage: At this stage the purified vWF GPIb binding domain polypeptide may be lyophilized. Upon reconstitution in a volume of water equal to the volume before lyophilization, the resultant solution contains exclusively monomeric protein showing no traces of dimers or other multimers on FPLC.

In a specific embodiment of this method the following procedure was performed:

a) 10 gm inclusion bodies (comprising 0.43 g net dry weight) were dissolved in a final volume of 100 ml 8M urea, 20 mM DTT, 20 mM HEPES pH 8, 100 mM NaCl.

b) The protein was loaded onto a CM Sepharose column equilibrated with 8M urea, 1 mM DTT, 20 mM HEPES pH 8, 100 mM NaCl. The protein eluted at 200 mM NaCL in 8M urea, 20 mM HEPES pH 8, 1 mM DTT, and was saved.

c) The saved eluate of the previous step was treated with 6M GuCl to eliminate any aggregates, and was then diluted to 0.05 $OD_{280}$/ml in 2M GuCl, 20 mM HEPES pH 8, 0.1 mM GSSG. Oxidation was performed overnight at room temperature. (Note that the oxidation step can be performed in the presence of urea instead of GuCl.)

d) The oxidation products were concentrated to $OD_{280}=1$ by ultrafiltration on a "MINITAN" unit containing a 30K membrane.

e) The concentrate of the previous step was dialyzed with three buffer changes against 20 mM HEPES pH 8, 100 mM NaCl. During dialysis, as the GuCl concentration decreased, a white precipitate formed which was removed by centrifugation and reprocessed once as described above. The supernatants were combined.

f) The combined supernatants were concentrated by binding to CM Sepharose in 20 mM HEPES pH 8, 100 mM NaCl. The polypeptide was eluted in 20 mM HEPES, pH 8, 400 mM NaCl and stored at 4° C.

g) The saved eluate from the previous step was dialyzed against 20 mM HEPES pH 8, 150 mM NaCl at 4° C.

h) After dialysis, the purified vWF GPIb binding domain polypeptide, designated VCL, was lyophilized.

Analysis of VCL

1. Amino acid sequence analysis of VCL purified as described above revealed that the N-terminal sequence is Met-Leu-His-Asp-Phe which is the expected sequence according to FIG. 12 with the addition of an N-terminal methionine residue.

2. Examination of VCL on polyacrylamide gels revealed that VCL electrophoreses at lower apparent molecular weight under non-reducing conditions than under reducing conditions (beta-mercaptoethanol). This shift from compact to less compact configuration is consistent with the reduction of a disulfide bond. Such an intramolecular bond is formed between the cysteines at positions 509 and 695. (The shift in molecular weight is not large enough to be consistent with the reduction of an intermolecular bond.)

Example 5

Biological Activity of VCL. a vWF GPIb binding domain polypeotide

The vwF GPIb binding domain polypeptide produced as described in Example 4 was designated VCL and was assayed for biological activity as described below.

1. Ristocetin induced platelet aggregation (RIPA)

RIPA assay was performed as described in Example 3 in a reaction mix containing $2 \times 10^8$ platelets/ml, 1 µg/ml plasma vWF, and 1 mg/ml ristocetin. A series of concentrations of VCL was tested and the $IC_{50}$ of VCL in 3 assays was determined to be 0.2–0.3 µM. 100% inhibition was achieved with about 1 µM VCL.

2. Asialo vWF induced platelet aggregation

Asialo vWF induced platelet aggregation assay was performed as described in Example 3 with 200 µl platelet-rich plasma (PRP) and 10 µg/ml asialo-vWF in a Lumi aggregometer. A series of concentrations of VCL was tested and the $IC_{50}$ of VCL in this assay was determined to be 0.15 µM, and complete inhibition by 0.5 µM.

3. Effect of VCL on preformed aggregates

The effect of VCL on preformed aggregates made by RIPA was tested. Aggregates were formed as in paragraph (1) above in the absence of VCL. Addition of VCL to a concentration of 0.5 µM disrupted the aggregates instantaneously.

4. Inhibition of thrombin induced platelet aggregation

Thrombin induced platelet aggregation assay was performed using 0.025 unit/ml thrombin and stractan prepared platelets. A series of concentrations of VCL was tested and the $IC_{50}$ of VCL in this assay was determined to be 0.3 µM. This is a surprising effect, since in a parallel experiment, VCL was not effective in inhibiting direct binding of [$^{125}$I] labelled thrombin to platelets.

5. Effect on platelet deposition under conditions of flow

In a model system consisting of an everted denuded human umbilical artery in a flow cell, platelet deposition may be determined. Whole human blood flows over the artery fragment. After 10–15 minutes, the flow is stopped and platelet deposition is determined microscopically. The $IC_{50}$ of VCL in this system was determined to be about 1 µM.

All the above results are summarized in Table III.

The inhibitory activity of VCL on ristocetin-induced or asialo vWF-induced platelet aggregation, ristocetin-induced vWF binding, and platelet adhesion was lost upon reduction of the disulfide bond between the cysteines at positions 509 and 695. In some experiments, the reduced VCL precipitated out of solution.

TABLE III

Biological Activity of VCL, a vWF GPIb Binding Domain Polypeptide.

| Example 5 (Paragraph No.) | Assay | µM VCL |
|---|---|---|
| 1 | Ristocetin induced platelet aggregation | $IC_{50}$ = 0.2–0.3 |
| 2 | Asialo vWF induced platelet aggregation | $IC_{50}$ = 0.15 |
| 3 | Thrombin induced platelet aggregation | $IC_{50}$ = 0.3 |
| 4 | Dissolution of preformed aggregates | 0.5 |
| 5 | Platelet deposition under conditions of flow | $IC_{50}$ = 1 |

Example 6

Construction of Plasmid pvWF-VEL

It was decided to construct a plasmid which expresses a slightly longer portion of the vWF GPIb binding domain than pvWF-VCL. The construction is shown in FIGS. 15–18 and described in the brief descriptions of the figures.

A. Construction of nvWF-VE2

Plasmid pvWF-VA2 (constructed as shown in FIG. 4) was digested with NdeI and PstI and the large fragment isolated. Four synthetic oligomers shown in FIG. 16 (SEQ ID NO: 3 for NO. 1, SEQ ID NO: 4 for No. 2, SEQ ID NO: 21 for No. 3, SEQ ID NO: 22 for NO. 4) were prepared. Nos. 2 and 3 were treated with T4 polynucleotide kinase to add 5' phosphate. The above mentioned large fragment of pvWF-VA2 was ligated as shown in FIG. 15 with the four oligomers (two kinased, and two non-kinased). The resulting plasmid shown in FIG. 15 was designated pvWF-VE2.

B. Construction of plasmid pvWF-VE3

Plasmid pvWF-VE2 was digested with NdeI and HindIII and the 770 bp fragment containing the vWF GPIb binding domain was isolated. Plasmid pMLK-7891 was also digested with NdeI and HindIII and the large fragment was isolated. The resulting plasmid, shown in FIG. 17, was designated pvWF-VE3.

C. Construction of plasmid pvWF-VEL

Plasmid pvWF-VE3 was digested with XmnI, dephosphorylated with bacterial alkaline phosphatase (BAP) and then digested with NdeI and HindIII. Plasmid pMLK-100 was digested with NdeI and HindIII and dephosphorylated with BAP. The two digests were then ligated to yield plasmid pvWF-VEL as shown in FIG. 18. This plasmid expresses the DNA sequence corresponding to amino acids 469–728 of mature vWF under the control of the $\lambda P_L$ promoter and the cII ribosomal binding site. The protein probably also includes an additional N-terminal methionine residue. A conservative base change was introduced into ala-473 changing GCC to GCA which also encodes alanine. This introduced an SphI site into the gene by changing GCCTGC to GCATGC.

Expression of pvWF-VEL in *E. coli* 4300(F$^-$) yields a 29 kD protein which reacts strongly with a monoclonal anti-vWF antibody and will be referred to herein as VEL.

EXAMPLE 7

Pharmaceutical Uses of vWF GPIb Binding Domain Polypeptide

Examples 1 and 4 describe the production and purification of a novel vWF GPIb binding domain polypeptide designated VCL. Some of the uses envisaged for VCL or for other vWF GPIb binding domain polypeptides are described below. Pharmaceutical compositions containing VCL or such other polypeptides may be formulated with a suitable pharmaceutically acceptable carrier using methods and carriers well known in the art.

1. The VCL composition described above may be used for prevention of platelet adhesion to damaged vascular surfaces (see Example 5, sub-section 5).
2. The VCL composition described above may be used for disruption of platelet-rich aggregates (see Example 5, subsection 3).
3. The VCL composition described above may be used for prevention of re-occlusion following angioplasty or thrombolysis (see Bellinger et al., PNAS, USA, 84: 8100–8104 (1987), Prevention of occlusive coronary artery thrombosis by a murine monoclonal antibody to porcine von Willebrand Factor).
4. The VCL composition described above may be used for prevention of platelet activation and thrombus formation due to high shear forces such as in stenosed or partially obstructed arteries or at arterial bifurcations (see Peterson et al., Blood 2: 625–628 (1987), Shear-induced platelet aggregation requires von Willebrand Factor and platelet membrane glycoproteins Ib and IIb–IIIa).
5. The VCL composition described above may be used for prevention of thrombosis and re-occlusion after angioplasty or thrombolysis due to thrombin activation of platelets (see Fuster et al., J. Am. Coll. Cardiol. 12: 78A–84A (1988), Antithrombotic therapy after myocardial reperfusion in acute myocardial infarction).
6. The VCL composition described above may be used for prevention of platelet adhesion to and aggregation on prosthetic materials (see Badimon et al., J. of Biomaterials Applications, 5: 27–48 (1990), Platelet interaction to prosthetic materials—role of von Willebrand Factor in Platelet Interaction to PTFE).
7. The VCL composition described above may be used for prevention of intramyocardial platelet aggregation in patients with unstable angina (see Davies et al., Circulation 73: 418–427 (1986), Intramyocardial platelet aggregation in patients with unstable angina suffering sudden ischemic cardiac death).
8. The VCL composition described above may be used for prevention of vasospasm and vasoconstriction following arterial injury caused by angioplasty, thrombolysis or other causes (see Lam et al., Circulation 75: 243–248 (1987), Is vasospasm related to platelet deposition?) .
9. The VCL composition described above may be used for prevention of restenosis following angioplasty or thrombolysis (see McBride et al., N. Eng. J. of Med. 318: 1734–1737 (1988), Restenosis after successful coronary angioplasty).
10. The VCL composition described above may be used for prevention of vaso-occlusive crises in sickle-cell anemia (see Wick et al., J. Clin. Invest. 80: 905–910 (1987), Unusually large von Willebrand multimers increase adhesion of sickle erythrocytes to human endothelial cells under controlled flow).
11. The VCL composition described above may be used for prevention of thrombosis associated with inflammatory response (see Esmon, Science 235: 1348–1352 (1987), The regulation of natural anticoagulant pathways).
12. The VCL composition described above may be used for prevention of arteriosclerosis (see Fuster et al., Circulation Res. 51: 587–593 (1982), Arteriosclerosis in normal and von Willebrand pigs).
13. The VCL composition described above may be used as an antimetastatic agent (see Kitagawa et al., Cancer Res. 49: 537–541 (1989), Involvement of platelet membrane glycoprotein Ib and IIb/IIIa complex in thrombin-dependent and -independent platelet aggregations induced by tumor cells).

EXAMPLE 8

1. In Vitro studies

For these studies VCL, or vehicle control, was made up fresh in sterile water (2.2 mg/ml stock).

A. Platelet Agareaation (PRP)

This is a standardized von Willebrand Factor (vWF)-dependent aggregation assay using human or rat platelet rich plasma (PRP). The addition of various concentrations of unfractionated Bothrops jararaca venom (BJV), which includes botrocetin and an additional thrombin-like component, or ristocetin results in an aggregatory response in the absence of any additional agent. Using ristocetin (1.5 mg/ml) as the agonist 43 $\mu$g/ml VCL abolished the aggregation of human PRP. Ristocetin up to 5.0 mg/ml did not cause measurable aggregation of rat PRP. Using this assay system with BJV as the agonist VCL at 83 $\mu$g/ml slightly inhibited the response of human PRP (FIG. 19) but not rat PRP (FIG. 20).

It is concluded that ristocetin is not a suitable agonist for inducing vWF dependent aggregation in the rat. Further, it is not possible to monitor the effects of VCL ex vivo using BJV-induced aggregation of rat PRP. However, VCL does inhibit vWF-dependent aggregation in human PRP in vitro.

B. Platelet Thrombin Receptor Assay

This assay measures the inhibition of thrombin-induced platelet pro-coagulant expression and is briefly described below. Human washed platelets are incubated in a buffer which contains $CaCl_2$, factor Xa, prothrombin, and human alpha-thrombin for 60 min at 28° C. At the end of this period an aliquot is transferred into a buffer containing S2238 and EDTA (to prevent any further thrombin generation). The S2238 reaction is terminated after 15 minutes at room temperature with acetic acid and the absorbance at 405 nm read. The amount of S2238 cleavage directly due to the added human alpha-thrombin is estimated by including a control which contains no prothrombin and this value is subtracted from all results. VCL was tested in this assay at a final concentration of 0.1 mg/ml.

This assay is sensitive to both thrombin inhibitors and thrombin receptor antagonists. In the presence of VCL the thrombin generation was 114% of control (n=2).

We therefore conclude that VCL is not a thrombin receptor antagonist in this system.

2. In Vivo studies

Arterial Thrombosis Model (Rat)

This method is essentially a modification of the model of Shand et al., Thromb. Res. 45 505–515 (1987). The method we use routinely is outlined below.

Rats are labelled with $^{111}$In platelets and $^{125}$I fibrinogen. The dorsal aorta is clamped, using modified Spencer-Wells forceps, for 1 minute. After a 45 minute reperfusion period the damaged vessel is removed, washed in citrate and counted. Results are expressed as mg blood equivalents. Differences in radiolabel accumulation between placebo and drug-treated animals are calculated and expressed as a percentage inhibition.

For the purpose of the evaluation of VCL the route of administration was by bolus intravenous injection. VCL was used at doses of 2 mg/kg (n=5) and 4 mg/kg (n=3). It was administered 1 minute prior to clamping. The vessel was then reperfused for twenty minutes. The antithrombotic effect was assessed at the 20 minute end point of the reperfusion. The shortening of the reperfusion time (as compared to routine) was designed to save compound. Appropriate vehicle controls (n=5 for both doses) were assessed.

It can be seen that under these conditions VCL inhibits thrombus formation in this model (Table IV). The inhibition is seen for the platelet ($^{III}$n) components of the thrombus at the 4 mg/kg dose. The other changes do not reach statistical significance, thus VCL shows antithrombotic efficacy in this rat arterial model.

In conclusion, VCL exhibits an antithrombotic effect in this rat model of arterial thrombosis which may be dose dependent.

3. Discussion

From the present data it appears that the VCL interacts with the human platelet vWF receptor and hence inhibits platelet aggregation in human PRP. There is however a marked difference between species (rat vs. human) when comparing inhibition of platelet aggregation. The species specificity of this effect and the causal mechanism were not investigated further. At a practical level this meant we were unable to analyze ex vivo samples in order to correlate the effects of VCL on aggregation and arterial thrombosis. Hence the analysis and interpretation of the in vivo efficacy of VCL as an antithrombotic in the rat arterial thrombosis model is complicated by this factor.

Despite GP1b possessing binding sites for both vWF and thrombin it would appear that any effects of VCL on thrombin binding to GP1b do not translate into antagonism of thrombin-induced pro-coagulant expression.

Overall VCL shows an antithrombotic effect in the rat arterial thrombosis model. This inhibition may be due to its interference with the binding of vWF to its receptor.

TABLE IV

The Effect of VCL on Arterial Thrombus Formation in the Rat Dorsal Aorta
% INHIBITION

| DOSE (mg/kg) | PLATELETS | P | FIBRINOGEN | P | N |
|---|---|---|---|---|---|
| 4 | 61.3 ± 8.0 | .01 | 34.7 ± 8.7 | NS | 3 |
| 2 | 25.54 ± 20.98 | NS | 22.78 ± 13.48 | NS | 5 |

The results are expressed as mean percentage inhibition ± standard error. The number of experiments in the treated groups are denoted in the table and in all cases were compared to a group of 5 control animals. Statistical analysis was performed on the raw data prior to transformation to percentage inhibition. NS=not statistically significant.

Example 9

Effect of VCL on In Vitro Platelet Binding to Vascular Components in a Laminar FloW Call The GPIb binding domain polypeptide, VCL, produced as described in Example 2 and purified as described in Example 4, was tested for its effect on binding of platelets to different substrates naturally found in the human vascular system. The substrates tested were endothelial cell extracellular matrix (ECM), fibrinogen, collagen, vWF, and fibronectin.

The test model, which has been previously described (Sakariassen et al, J. Lab. Clin. Med. 102: 522–535 (1983)), consists of a laminar flow cell into which a glass cover slip containing the test surface is inserted. The test surface is formed by spraying or otherwise forming a layer of the substrate on the glass cover slip. After insertion into the flow cell, the cover slip is then subjected to perfusion with platelets under conditions of controlled flow and shear rates, and platelet adhesion is determined as percent coverage of the test surface by platelets.

1. ECM: Endothelial cells were grown on a glass cover slip and removed, leaving a layer of ECM as the test surface. Platelet binding was measured at two shear rates. The results are shown in FIG. 21. Platelet coverage was approximately 25% and 50% at shear rates of 300 and 1300 s$^{-1}$ respectively. The presence of 1 μM VCL in the perfusion solution inhibited platelet adhesion to levels of about 8% and 28% coverage respectively, which correspond to about 70% and 50% inhibition respectively. These figures show no significant difference in VCL inhibition at high and low shear rates.

FIG. 22 shows a dose-response curve to VCL at a shear rate of 1300 s$^{-1}$ from which it is possible to extrapolate a value for the IC$_{50}$=0.8 μM VCL.

2. Fibrinogen: Platelet binding to a test surface of immobilized fibrinogen was approximately equal at the two shear rates tested (300 and 1300 s$^{-1}$), and in both cases was between 35–40% as shown in FIG. 23. Inhibition by 1 μM VCL was approximately 40% at the lower shear rate and 75% at the higher shear rate, representing coverage of about 22% and 10% respectively. Hantgan et al, Blood 2:345–353, using monoclonal antibodies to α-GPIb and α-vWF (GPIb site) have shown that vWF is a major intermediate in platelet adhesion to fibrinogen. However, to the best of our knowledge,this is the first disclosure that a vWF polypeptide fragment inhibits platelet adhesion to fibrin. These results thus demonstrate the possible use of VCL in prevention of reocclusion following thrombolysis by blocking binding of platelets to the fibrin-rich residues present in blood after thrombolysis. VCL does not inhibit platelet binding to laminin (another subendothelial matrix protein) indicating that the platelet-fibrin interaction is indeed a specific vWF mediated reaction, while the platelet-laminin reaction is not mediated by vWF.

3. Collagen, vwF, and Fibronectin: These three substrates were compared by preparing test surfaces of each as described above. The results are shown in FIG. 24.

Platelet adhesion to immobilized collagen (type I) was low: about 8% coverage at 300 s$^{-1}$ shear rate and about 4% coverage at 1300 s$^{-1}$ shear rate. 1 μM VCL inhibited this adhesion by about 50%.

Platelet adhesion to test surfaces of immobilized vWF was quite high: about 20% at a shear rate of 300 s$^{-1}$, and about 40% at a shear rate of 1300 s$^{-1}$. 1 μM VCL inhibited adhesion by only about 25%. This is consistent with data demonstrating that platelet adhesion to immobilized vWF is primarily via GPIIb–IIIA and only partially via GPIb. Interactions between platelets and immobilized vWF, particularly purified vWF immobilized on a glass or plastic surface, are mainly through the GPIIb–IIIa sites rather than through the GPIb site which may be blocked by VCL.

Platelet adhesion to immobilized fibronectin was about 10% at both 300 s$^{-1}$ and 1300 s$^{-1}$ shear rates. However, VCL inhibition was only about 25% at the lower shear rate, but approximately 80% at the higher shear rate. This is an indication that vWF mediates platelet adhesion to immobilized fibronectin at high shear rates.

4. VCL: Platelet adhesion to immobilized VCL was also tested. Adhesion of platelets to VCL is shown by the data summarized in FIG. 25. Adhesion of platelets is ≦5% coverage at both low and high shear rates, which was ten-fold higher than adhesion to albumin under the same conditions. This indicates specific binding of VCL to platelets. The low coverage is probably a characteristic of the VCL substrate being immobilized on the glass surface. Behavior in solution may be expected to differ.

The above results give an indication that VCL is particularly effective at inhibiting platelet adhesion to specific substrates at high shear rates. From this, it may be inferred that vWF mediates platelet binding at high shear rates.

Since clinically relevant situations are often in regions of high shear (e.g. residual thrombus, percutaneous transluminal coronary angioplasty (PTCA)), a vWF polypeptide fragment such as the GPIb binding site polypeptide VCL may be of particular utility in such circumstances.

An example of the efficacy of VCL in inhibiting platelet adhesion ex vivo at high shear rates is shown in Example 10.

Example 10

Ex Vivo Inhibition of Platelet Adhesion by VCL in a Porcine Aorta model

The effect of VCL was tested in a model more closely approximating in vivo conditions (Badimon et al, Artiosclerosis 6:312–320, (1986). A section of porcine aorta was perfused in a flow cell with normal human blood containing 90 mM sodium citrate and additionally containing $^{111}$Indium labelled platelets. The aortic section was treated to mimic mild (MD) or severe (SD) vessel wall damage. The blood was incubated with saline or 0.5 μM VCL for 10 minutes prior to perfusion. Following perfusion for 5 minutes, and appropriate washing, platelet adhesion was determined by measuring the tissue radioactivity.

The results, summarized in Table V, show that VCL is effective in reducing platelet deposition at the high flow rate tested, but not at a low flow rate. The effect of VCL was particularly dramatic in the experiment mimicking severe damage where platelet deposition was reduced from $164 \pm 48 \times 10^5/cm^2$ to $64 \pm 15 \times 10^5/cm^2$, a reduction of approximately 60%. In mildly damaged tissue, the reduction was about 50%, from platelet deposition of $25 \pm 7 \times 10^5/cm^2$ to $13 \pm 4 \times 10^5/cm^2$. At the low flow rate tested, VCL did not inhibit platelet deposition to seriously damaged tissue.

TABLE V

Effect of VCL on Platelet Adhesion to Damaged Porcine Artery Ex Vivo

| Damage type | Shear rate | Inhibitor | |
|---|---|---|---|
| | | Saline | VCL |
| SD | 212 S$^{-1}$ | 55 ± 16 | 48 ± 18 |
| SD | 1690 S$^{-1}$ | 164 ± 48 | 64 ± 15 |
| MD | 1690 S$^{-1}$ | 25 ± 7 | 13 ± 4 |

As discussed in Example 9, since clinically relevant situations are often in regions of high shear, a vWF GPIb binding site polypeptide fragment such as VCL may be of particular utility in such circumstances.

These results suggest that VCL is effective in reducing mural thrombus formation by inhibiting interaction between platelets and blood vessel walls, and may be especially effective in clinical situations of high risk of thrombosis such as stenotic disrupted atherosclerotic plaque which is a condition comprising severe damage at high shear rate.

Example 11

Effect of VCL in Stabilizina Cardiovascular Function in an In Vivo Canine Coronarv Artery Model A mild stenosis was created in a canine coronary artery using a cylindrical, plastic constrictor. As a result of the stenosis, thrombi form and embolize spontaneously in a cyclic manner leading to cyclic flow variations (CFV) (Ashton et al, Circulation Research 59:568–578 (1986)).

The test material is administered after establishment of CFV. The result is expressed as the percentage of animals in which CFV is abolished as a result of administration of the material being tested. Subsequently, renewed platelet aggregation is induced by the administration of epinephrine. The percentage of treated animals in which epinephrine administration induces CFV as a result of renewed platelet aggregation is a further indication of the efficacy of the materials under evaluation.

Two materials, VCL, a GPIb binding domain polypeptide, and a thromboxane A$_2$ (TXA$_2$) receptor antagonist were tested to determine their effect in this model. VCL was administered at 0.5 mg/kg i.v. bolus plus 0.25 mg/kg/hr i.v infusion to maintain blood concentration of about 0.3 μM, based on 1 liter of blood representing approximately 14 kg of body weight.

The results are summarized in Table VI. VCL abolished CFV in 43% of the animals, the TXA$_2$ receptor antagonist in 71% of the animals, and the two materials in combination abolished CFV in 100% of the animals.

Subsequent administration of epinephrine reestablished CFV in 100% of the animals treated with only one of the two materials tested, but in only 50% of the animals treated with the combination of both materials.

Furthermore, as may be seen from Table VI, the dose of epinephrine required to restore CFV was higher in the animals treated with VCL (0.3 μg/kg/min) than in animals treated with the TXA$_2$ receptor antagonist (0.2 μg/kg/min), and at least double in the animals treated with both (0.6 μg/kg/min). Thus VCL provides greater protection against epinephrine induced CFV than TXA$_2$ receptor antagonist, and use of VCL in combination with TXA$_2$ receptor antagonist provides at least double the protection of either agent used alone.

TABLE VI

In Vivo Effect of VCL on CFV in Dogs

| Test Compound | % Abolition of CFV | Epinephrine Dosage μg/kg/min | % Restoration of CFV by Epinephrine Induced Platelet Aggregation |
|---|---|---|---|
| VCL | 43 | 0.3 | 100 |
| TXA$_2$ receptor antagonist | 71 | 0.2 | 100 |
| VCL + TXA$_2$ receptor antagonist | 100 | 0.6 | 50 |

These results are an indication that VCL confers increased protection against CFV and against epinephrine induced platelet aggregation.

Example 12

Effect of VCL on Bleeding in a Baboon

A model using a baboon for vascular studies has been described (Kelly et al, Blood 77:1006–1012, (March 1991)). Preliminary results indicate that administration of 10 μM VCL increased bleeding time from 4 minutes to 30 minutes without affecting platelet viability or causing thrombocytopenia. These are attributes required of an inhibitor of platelet adhesion to subendothelium.

Based on these results and the results presented in Example 11, probable dosages would be in range of 0.1–200 mg/kg body weight, preferably 1–20 mg/kg body weight, based on 1L blood representing about 14 kg body weight. It might be necessary for further i.v. administration to maintain a blood concentration of about 1 $\mu$M.

---

What is claimed is:

1. A method of preventing arteriosclerosis in a subject which comprises administering to the subject an amount of a composition comprising a polypeptide consistinq of the amino acid sequence, X-Leu His Asp Phe Tyr Cys Ser Arg Leu Leu Asp Leu Val Phe Leu Leu Asp Gly Ser Ser Arg Leu Ser Glu Ala Glu Phe Glu Val Leu Lys Ala Phe Val Val Asp Met Met Glu Arg Leu Arg Ile Ser Gln Lys Trp Val Arg Val Ala Val Val Glu Tyr His Asp Gly Ser His Ala Tyr Ile Gly Leu Lys Asp Arg Lys Arg Pro Ser Glu Leu Arg Arg Ile Ala Ser Gln Val Lys Tyr Ala Gly Ser Gln Val Ala Ser Thr Ser Glu Val Leu Lys Tyr Thr Leu Phe Gln Ile Phe Ser Lys Ile Asp Arg Pro Glu Ala Ser Arg Ile Ala Leu Leu Leu Met Ala Ser Gln Glu Pro Gln Arg Met Ser Arg Asn Phe Val Arg Tyr Val Gln Gly Leu Lys Lys Lys Lys Val Ile Val Ile Pro Val Gly Ile Gly Pro His Ala Asn Leu Lys Gln Ile Arg Leu Ile Glu Lys Gln Ala Pro Glu Asn Lys Ala Phe Val Leu Ser Ser Val Asp Glu Leu Glu Gln Gln Arg Asp Glu Ile Val Ser Tyr Leu Cys Asp Leu Ala Pro Glu Ala Pro Pro Pro Thr Leu Pro Pro Asp Met Ala Gln Val Thr Val Gly Pro Gly Leu Leu Gly Val Ser Thr Leu Gly Pro Lys-COOH" (SEQ ID NO: 23) wherein X is NH$_2$-methionine- or N$_2$H- and the two cysteines included in the sequence are joined by a disulfide bond, and wherein the amount of the polypeptide is effective to prevent arteriosclerosis.

2. A method of preventing stenosis as a result of smooth muscle proliferation following vascular injury in a subject which comprises administering to the subject an amount of a composition comprising a polypeptide consisting of the amino acid sequence, after "X-Leu His Asp Phe Tyr Cys Ser Arg Leu Leu Asp Leu Val Phe Leu Leu Asp Gly Ser Ser Arg Leu Ser Glu Ala Glu Phe Glu Val Leu Lys Ala Phe Val Val Asp Met Met Glu Arg Leu Arg Ile Ser Gln Lys Trp Val Arg Val Ala Val Val Glu Tyr His Asp Gly Ser His Ala Tyr Ile Gly Leu Lys Asp Arg Lys Arg Pro Ser Glu Leu Arg Arg Ile Ala Ser Gln Val Lys Tyr Ala Gly Ser Gln Val Ala Ser Thr Ser Glu Val Leu Lys Tyr Thr Leu Phe Gln Ile Phe Ser Lys Ile Asp Arg Pro Glu Ala Ser Arg Ile Ala Leu Leu Leu Met Ala Ser Gln Glu Pro Gln Arg Met Ser Arg Asn Phe Val Arg Tyr Val Gln Gly Leu Lys Lys Lys Lys Val Ile Val Ile Pro Val Gly Ile Gly Pro His Ala Asn Leu Lys Gln Ile Arg Leu Ile Glu Lys Gln Ala Pro Glu Asn Lys Ala Phe Val Leu Ser Ser Val Asp Glu Leu Glu Gln Gln Arg Asp Glu Ile Val Ser Tyr Leu Cys Asp Leu Ala Pro Glu Ala Pro Pro Pro Thr Leu Pro Pro Asp Met Ala Gln Val Thr Val Gly Pro Gly Leu Leu Gly Val Ser Thr Leu Gly Pro Lys-COOH (SEQ ID NO: 24) wherein X is the NH$_2$-methionine- or NH$_2$- and the two cysteines included in the sequence are joined by a disulfide bond, and wherein the amount of the polypeptide is effective to prevent stenosis.

3. A method of preventing arteriosclerosis in a subject which comprises administering to the subject an amount of a composition comprising a polypeptide consisting of the amino acid sequence X-A-Cys Ser Arg Leu Leu Asp Leu Val Phe Leu Leu Asp Gly Ser Ser Arg Leu Ser Glu Ala Glu Phe Glu Val Leu Lys Ala Phe Val Val Asp Met Met Glu Arg Leu Arg Ile Ser Gln Lys Trp Val Arg Val Ala Val Val Glu Tyr His Asp Gly Ser His Ala Tyr Ile Gly Leu Lys Asp Arg Lys Arg Pro Ser Glu Leu Arg Arg Ile Ala Ser Gln Val Lys Tyr Ala Gly Ser Gln Val Ala Ser Thr Ser Glu Val Leu Lys Tyr Thr Leu Phe Gln Ile Phe Ser Lys Ile Asp Arg Pro Glu Ala Ser Arg Ile Ala Leu Leu Leu Met Ala Ser Gln Glu Pro Gln Arg Met Ser Arg Asn Phe Val Arg Tyr Val Gln Gly Leu Lys Lys Lys Lys Val Ile Val Ile Pro Val Gly Ile Gly Pro His Ala Asn Leu Lys Gln Ile Arg Leu Ile Glu Lys Gln Ala Pro Glu Asn Lys Ala Phe Val Leu Ser Ser Val Asp Glu Leu Glu Gln Gln Arg Asp Glu Ile Val Ser Tyr Leu Cys Asp Leu Ala Pro Glu Ala Pro Pro Pro Thr Leu Pro Pro Asp Met Ala Gln Val Thr Val Gly Pro Gly Leu Leu Gly Val Ser Thr Leu Gly Pro Lys" (SEQ ID NO: 23)

wherein X is NH$_2$-methionine- or NH$_2$-;

A is a sequence of at least 1, but no more than 5 amino acids, which sequence is present in naturally-occurring human vWF, the carboxy terminal amino acid of which is the tyrosine #508 shown in FIG. 12 and each succeeding amino acid of which is the next successive N-terminal amino acid shown in FIG. 12 (SEQ ID NO:2); and the two cysteines included in the sequence are joined by a disulfide bond, and wherein the amount of the polypeptide is effective to prevent arteriosclerosis.

4. A method of preventing stenosis as a result of smooth muscle proliferation following vascular injury in a subject which comprises administering to the subject an amount of a composition comprising a polypeptide consisting of the amino acid sequence X-A-Cys Ser Arg Leu Leu Asp Leu Val Phe Leu Leu Asp Gly Ser Ser Arg Leu Ser Glu Ala Glu Phe Glu Val Leu Lys Ala Phe Val Val Asp Met Met Glu Arg Leu Arg Ile Ser Gln Lys Trp Val Arg Val Ala Val Val Glu Tyr His Asp Gly Ser His Ala Tyr Ile Gly Leu Lys Asp Arg Lys Arg Pro Ser Glu Leu Arg Arg Ile Ala Ser Gln Val Lys Tyr Ala Gly Ser Gln Val Ala Ser Thr Ser Glu Val Leu Lys Tyr Thr Leu Phe Gln Ile Phe Ser Lys Ile Asp Arg Pro Glu Ala Ser Arg Ile Ala Leu Leu Leu Met Ala Ser Gln Glu Pro Gln Arg Met Ser Arg Asn Phe Val Arg Tyr Val Gln Gly Leu Lys Lys Lys Lys Val Ile Val Ile Pro Val Gly Ile Gly Pro His Ala Asn Leu Lys Gln Ile Arg Leu Ile Glu Lys Gln Ala Pro Glu Asn Lys Ala Phe Val Leu Ser Ser Val Asp Glu Leu Glu Gln Gln Arg Asp Glu Ile Val Ser Tyr Leu Cys Asp Leu Ala Pro Glu Ala Pro Pro Pro Thr Leu Pro Pro Asp Met Ala Gln Val Thr Val Gly Pro Gly lieu Leu Gly Val Ser Thr Leu Gly Pro Lys (SEQ ID NO: 24) wherein X is NH$_2$-methionine- or NH$_2$-;

A is a sequence of at least 1, but no more than 5 amino acids, which sequence is present in naturally-occurring human vWF, the carboxy terminal amino acid of which is the tyrosine #508 shown in FIG. 12 (SEQ ID NO: 2) and each succeeding amino acid of which is the next successive N-terminal amino acid shown in FIG. 12 (SEQ ID NO:2); and the two cysteines included in the sequence are joined by a disulfide bond, and wherein the amount of the polypeptide is effect to prevent stenosis.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
       (A) LENGTH: 187 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

```
Cys Ser Arg Leu Leu Asp Leu Val Phe Leu Leu Asp Gly Ser Ser Arg
1               5                   10                  15

Leu Ser Glu Ala Glu Phe Glu Val Leu Lys Ala Phe Val Val Asp Met
            20                  25                  30

Met Glu Arg Leu Arg Ile Ser Gln Lys Trp Val Arg Val Ala Val Val
            35                  40                  45

Glu Tyr His Asp Gly Ser His Ala Tyr Ile Gly Leu Lys Asp Arg Lys
50                  55                  60

Arg Pro Ser Glu Leu Arg Arg Ile Ala Ser Gln Val Lys Tyr Ala Gly
65                  70                  75                  80

Ser Gln Val Ala Ser Thr Ser Glu Val Leu Lys Tyr Thr Leu Phe Gln
            85                  90                  95

Ile Phe Ser Lys Ile Asp Arg Pro Glu Ala Ser Arg Ile Ala Leu Leu
            100                 105                 110

Leu Met Ala Ser Gln Glu Pro Gln Arg Met Ser Arg Asn Phe Val Arg
            115                 120                 125

Tyr Val Gln Gly Leu Lys Lys Lys Lys Val Ile Val Ile Pro Val Gly
            130                 135                 140

Ile Gly Pro His Ala Asn Leu Lys Gln Ile Arg Leu Ile Glu Lys Gln
145                 150                 155                 160

Ala Pro Glu Asn Lys Ala Phe Val Leu Ser Ser Val Asp Glu Leu Glu
            165                 170                 175

Gln Gln Arg Asp Glu Ile Val Ser Tyr Leu Cys
            180                 185
```

(2) INFORMATION FOR SEQ ID NO:2:

(i) SEQUENCE CHARACTERISTICS:
       (A) LENGTH: 6153 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (ix) FEATURE:
    (A) NAME/KEY: CDS
    (B) LOCATION: 1..6153

(xi) SEQUENCE DESCRIPTION: SEQ ID NO:2:

```
AGC CTA TCC TGT CGG CCC CCC ATG GTC AAG CTG GTG TGT CCC GCT GAC        48
Ser Leu Ser Cys Arg Pro Pro Met Val Lys Leu Val Cys Pro Ala Asp
 1               5                  10                  15

AAC CTG CGG GCT GAA GGG CTC GAG TGT ACC AAA ACG TGC CAG AAC TAT        96
Asn Leu Arg Ala Glu Gly Leu Glu Cys Thr Lys Thr Cys Gln Asn Tyr
             20                  25                  30

GAC CTG GAG TGC ATG AGC ATG GGC TGT GTC TCT GGC TGC CTC TGC CCC       144
Asp Leu Glu Cys Met Ser Met Gly Cys Val Ser Gly Cys Leu Cys Pro
         35                  40                  45

CCG GGC ATG GTC CGG CAT GAG AAC AGA TGT GTG GCC CTG GAA AGG TGT       192
Pro Gly Met Val Arg His Glu Asn Arg Cys Val Ala Leu Glu Arg Cys
     50                  55                  60

CCC TGC TTC CAT CAG GGC AAG GAG TAT GCC CCT GGA GAA ACA GTG AAG       240
Pro Cys Phe His Gln Gly Lys Glu Tyr Ala Pro Gly Glu Thr Val Lys
 65                  70                  75                  80

ATT GGC TGC AAC ACT TGT GTC TGT CGG GAC CGG AAG TGG AAC TGC ACA       288
Ile Gly Cys Asn Thr Cys Val Cys Arg Asp Arg Lys Trp Asn Cys Thr
                 85                  90                  95

GAC CAT GTG TGT GAT GCC ACG TGC TCC ACG ATC GGC ATG GCC CAC TAC       336
Asp His Val Cys Asp Ala Thr Cys Ser Thr Ile Gly Met Ala His Tyr
            100                 105                 110

CTC ACC TTC GAC GGG CTC AAA TAC CTG TTC CCC GGG GAG TGC CAG TAC       384
Leu Thr Phe Asp Gly Leu Lys Tyr Leu Phe Pro Gly Glu Cys Gln Tyr
        115                 120                 125

GTT CTG GTG CAG GAT TAC TGC GGC AGT AAC CCT GGG ACC TTT CGG ATC       432
Val Leu Val Gln Asp Tyr Cys Gly Ser Asn Pro Gly Thr Phe Arg Ile
    130                 135                 140

CTA GTG GGG AAT AAG GGA TGC AGC CAC CCC TCA GTG AAA TGC AAG AAA       480
Leu Val Gly Asn Lys Gly Cys Ser His Pro Ser Val Lys Cys Lys Lys
145                 150                 155                 160

CGG GTC ACC ATC CTG GTG GAG GGA GGA GAG ATT GAG CTG TTT GAC GGG       528
Arg Val Thr Ile Leu Val Glu Gly Gly Glu Ile Glu Leu Phe Asp Gly
                165                 170                 175

GAG GTG AAT GTG AAG AGG CCC ATG AAG GAT GAG ACT CAC TTT GAG GTG       576
Glu Val Asn Val Lys Arg Pro Met Lys Asp Glu Thr His Phe Glu Val
            180                 185                 190

GTG GAG TCT GGC CGG TAC ATC ATT CTG CTG CTG GGC AAA GCC CTC TCC       624
Val Glu Ser Gly Arg Tyr Ile Ile Leu Leu Leu Gly Lys Ala Leu Ser
        195                 200                 205

GTG GTC TGG GAC CGC CAC CTG AGC ATC TCC GTG GTC CTG AAG CAG ACA       672
Val Val Trp Asp Arg His Leu Ser Ile Ser Val Val Leu Lys Gln Thr
    210                 215                 220

TAC CAG GAG AAA GTG TGT GGC CTG TGT GGG AAT TTT GAT GGC ATC CAG       720
Tyr Gln Glu Lys Val Cys Gly Leu Cys Gly Asn Phe Asp Gly Ile Gln
225                 230                 235                 240

AAC AAT GAC CTC ACC AGC AGC AAC CTC CAA GTG GAG GAG GAC CCT GTG       768
Asn Asn Asp Leu Thr Ser Ser Asn Leu Gln Val Glu Glu Asp Pro Val
                245                 250                 255

GAC TTT GGG AAG TCC TGG GAA GTG AGC TCG CAG TGT GCT GAC ACC AGA       816
Asp Phe Gly Lys Ser Trp Glu Val Ser Ser Gln Cys Ala Asp Thr Arg
            260                 265                 270

AAA GTG CCT CTG GAC TCA TCC CCT GCC ACC TGC CAT AAC AAC ATC ATG       864
Lys Val Pro Leu Asp Ser Ser Pro Ala Thr Cys His Asn Asn Ile Met
        275                 280                 285

AAG CAG ACG ATG GTG GAT TCC TCC TGT AGA ATC CTT ACC AGT GAC GTC       912
Lys Gln Thr Met Val Asp Ser Ser Cys Arg Ile Leu Thr Ser Asp Val
```

```
                              290                     295                     300
TTC CAG GAC TGC AAC AAG CTG GTG GAC CCC GAG CCA TAT CTG GAT GTC        960
Phe Gln Asp Cys Asn Lys Leu Val Asp Pro Glu Pro Tyr Leu Asp Val
305                     310                     315                     320

TGC ATT TAC GAC ACC TGC TCC TGT GAG TCC ATT GGG GAC TGC GCC TGC       1008
Cys Ile Tyr Asp Thr Cys Ser Cys Glu Ser Ile Gly Asp Cys Ala Cys
                325                     330                     335

TTC TGC GAC ACC ATT GCT GCC TAT GCC CAC GTG TGT GCC CAG CAT GGC       1056
Phe Cys Asp Thr Ile Ala Ala Tyr Ala His Val Cys Ala Gln His Gly
                340                     345                     350

AAG GTG GTG ACC TGG AGG ACG GCC ACA TTG TGC CCC CAG AGC TGC GAG       1104
Lys Val Val Thr Trp Arg Thr Ala Thr Leu Cys Pro Gln Ser Cys Glu
                355                     360                     365

GAG AGG AAT CTC CGG GAG AAC GGG TAT GAG TGT GAG TGG CGC TAT AAC       1152
Glu Arg Asn Leu Arg Glu Asn Gly Tyr Glu Cys Glu Trp Arg Tyr Asn
370                     375                     380

AGC TGT GCA CCT GCC TGT CAA GTC ACG TGT CAG CAC CCT GAG CCA CTG       1200
Ser Cys Ala Pro Ala Cys Gln Val Thr Cys Gln His Pro Glu Pro Leu
385                     390                     395                     400

GCC TGC CCT GTG CAG TGT GTG GAG GGC TGC CAT GCC CAT TGC CCT CCA       1248
Ala Cys Pro Val Gln Cys Val Glu Gly Cys His Ala His Cys Pro Pro
                405                     410                     415

GGC AAA ATC CTG GAT GAG CTT TTG CAG ACC TGC GTT GAC CCT GAA GAC       1296
Gly Lys Ile Leu Asp Glu Leu Leu Gln Thr Cys Val Asp Pro Glu Asp
                420                     425                     430

TGT CCA GTG TGT GAG GTG GCT GGC CGG CGT TTT GCC TCA GGA AAG AAA       1344
Cys Pro Val Cys Glu Val Ala Gly Arg Arg Phe Ala Ser Gly Lys Lys
                435                     440                     445

GTC ACC TTG AAT CCC AGT GAC CCT GAG CAC TGC CAG ATT TGC CAC TGT       1392
Val Thr Leu Asn Pro Ser Asp Pro Glu His Cys Gln Ile Cys His Cys
450                     455                     460

GAT GTT GTC AAC CTC ACC TGT GAA GCC TGC CAG GAG CCG GGA GGC CTG       1440
Asp Val Val Asn Leu Thr Cys Glu Ala Cys Gln Glu Pro Gly Gly Leu
465                     470                     475                     480

GTG GTG CCT CCC ACA GAT GCC CCG GTG AGC CCC ACC ACT CTG TAT GTG       1488
Val Val Pro Pro Thr Asp Ala Pro Val Ser Pro Thr Thr Leu Tyr Val
                485                     490                     495

GAG GAC ATC TCG GAA CCG CCG TGG CAC GAT TTC TAC TGC AGC AGG CTA       1536
Glu Asp Ile Ser Glu Pro Pro Trp His Asp Phe Tyr Cys Ser Arg Leu
                500                     505                     510

CTG GAC CTG GTC TTC CTG CTG GAT GGC TCC TCC AGG CTG TCC GAG GCT       1584
Leu Asp Leu Val Phe Leu Leu Asp Gly Ser Ser Arg Leu Ser Glu Ala
                515                     520                     525

GAG TTT GAA GTG CTG AAG GCC TTT GTG GTG GAC ATG ATG GAG CGG CTG       1632
Glu Phe Glu Val Leu Lys Ala Phe Val Val Asp Met Met Glu Arg Leu
530                     535                     540

CGC ATC TCC CAG AAG TGG GTC CGC GTG GCC GTG GTG GAG TAC CAC GAC       1680
Arg Ile Ser Gln Lys Trp Val Arg Val Ala Val Val Glu Tyr His Asp
545                     550                     555                     560

GGC TCC CAC GCC TAC ATC GGG CTC AAG GAC CGG AAG CGA CCA TCA GAG       1728
Gly Ser His Ala Tyr Ile Gly Leu Lys Asp Arg Lys Arg Pro Ser Glu
                565                     570                     575

CTG CGG CGC ATT GCC AGC CAG GTG AAG TAT GCG GGC AGC CAG GTG GCC       1776
Leu Arg Arg Ile Ala Ser Gln Val Lys Tyr Ala Gly Ser Gln Val Ala
                580                     585                     590

TCC ACC AGC GAG GTC TTG AAA TAC ACA CTG TTC CAA ATC TTC AGC AAG       1824
Ser Thr Ser Glu Val Leu Lys Tyr Thr Leu Phe Gln Ile Phe Ser Lys
                595                     600                     605

ATC GAC CGC CCT GAA GCC TCC CGC ATC GCC CTG CTC CTG ATG GCC AGC       1872
Ile Asp Arg Pro Glu Ala Ser Arg Ile Ala Leu Leu Leu Met Ala Ser
```

-continued

|     |     |     |     | 610 |     |     |     |     | 615 |     |     |     |     | 620 |     |      |
|-----|-----|-----|-----|-----|-----|-----|-----|-----|-----|-----|-----|-----|-----|-----|-----|------|
| CAG | GAG | CCC | CAA | CGG | ATG | TCC | CGG | AAC | TTT | GTC | CGC | TAC | GTC | CAG | GGC | 1920 |
| Gln | Glu | Pro | Gln | Arg | Met | Ser | Arg | Asn | Phe | Val | Arg | Tyr | Val | Gln | Gly |      |
| 625 |     |     |     | 630 |     |     |     |     | 635 |     |     |     |     | 640 |     |      |

| CTG | AAG | AAG | AAG | AAG | GTC | ATT | GTG | ATC | CCG | GTG | GGC | ATT | GGG | CCC | CAT | 1968 |
|-----|-----|-----|-----|-----|-----|-----|-----|-----|-----|-----|-----|-----|-----|-----|-----|------|
| Leu | Lys | Lys | Lys | Lys | Val | Ile | Val | Ile | Pro | Val | Gly | Ile | Gly | Pro | His |      |
|     |     |     |     | 645 |     |     |     |     | 650 |     |     |     |     | 655 |     |      |

| GCC | AAC | CTC | AAG | CAG | ATC | CGC | CTC | ATC | GAG | AAG | CAG | GCC | CCT | GAG | AAC | 2016 |
|-----|-----|-----|-----|-----|-----|-----|-----|-----|-----|-----|-----|-----|-----|-----|-----|------|
| Ala | Asn | Leu | Lys | Gln | Ile | Arg | Leu | Ile | Glu | Lys | Gln | Ala | Pro | Glu | Asn |      |
|     |     |     | 660 |     |     |     |     | 665 |     |     |     |     | 670 |     |     |      |

| AAG | GCC | TTC | GTG | CTG | AGC | AGT | GTG | GAT | GAG | CTG | GAG | CAG | CAA | AGG | GAC | 2064 |
|-----|-----|-----|-----|-----|-----|-----|-----|-----|-----|-----|-----|-----|-----|-----|-----|------|
| Lys | Ala | Phe | Val | Leu | Ser | Ser | Val | Asp | Glu | Leu | Glu | Gln | Gln | Arg | Asp |      |
|     |     | 675 |     |     |     |     | 680 |     |     |     |     | 685 |     |     |     |      |

| GAG | ATC | GTT | AGC | TAC | CTC | TGT | GAC | CTT | GCC | CCT | GAA | GCC | CCT | CCT | CCT | 2112 |
|-----|-----|-----|-----|-----|-----|-----|-----|-----|-----|-----|-----|-----|-----|-----|-----|------|
| Glu | Ile | Val | Ser | Tyr | Leu | Cys | Asp | Leu | Ala | Pro | Glu | Ala | Pro | Pro | Pro |      |
|     | 690 |     |     |     |     | 695 |     |     |     |     | 700 |     |     |     |     |      |

| ACT | CTG | CCC | CCC | GAC | ATG | GCA | CAA | GTC | ACT | GTG | GGC | CCG | GGG | CTC | TTG | 2160 |
|-----|-----|-----|-----|-----|-----|-----|-----|-----|-----|-----|-----|-----|-----|-----|-----|------|
| Thr | Leu | Pro | Pro | Asp | Met | Ala | Gln | Val | Thr | Val | Gly | Pro | Gly | Leu | Leu |      |
| 705 |     |     |     |     | 710 |     |     |     |     | 715 |     |     |     |     | 720 |      |

| GGG | GTT | TCG | ACC | CTG | GGG | CCC | AAG | AGG | AAC | TCC | ATG | GTT | CTG | GAT | GTG | 2208 |
|-----|-----|-----|-----|-----|-----|-----|-----|-----|-----|-----|-----|-----|-----|-----|-----|------|
| Gly | Val | Ser | Thr | Leu | Gly | Pro | Lys | Arg | Asn | Ser | Met | Val | Leu | Asp | Val |      |
|     |     |     |     | 725 |     |     |     |     | 730 |     |     |     |     | 735 |     |      |

| GCG | TTC | GTC | CTG | GAA | GGA | TCG | GAC | AAA | ATT | GGT | GAA | GCC | GAC | TTC | AAC | 2256 |
|-----|-----|-----|-----|-----|-----|-----|-----|-----|-----|-----|-----|-----|-----|-----|-----|------|
| Ala | Phe | Val | Leu | Glu | Gly | Ser | Asp | Lys | Ile | Gly | Glu | Ala | Asp | Phe | Asn |      |
|     |     |     | 740 |     |     |     |     | 745 |     |     |     |     | 750 |     |     |      |

| AGG | AGC | AAG | GAG | TTC | ATG | GAG | GAG | GTG | ATT | CAG | CGG | ATG | GAT | GTG | GGC | 2304 |
|-----|-----|-----|-----|-----|-----|-----|-----|-----|-----|-----|-----|-----|-----|-----|-----|------|
| Arg | Ser | Lys | Glu | Phe | Met | Glu | Glu | Val | Ile | Gln | Arg | Met | Asp | Val | Gly |      |
|     |     | 755 |     |     |     |     | 760 |     |     |     |     | 765 |     |     |     |      |

| CAG | GAC | AGC | ATC | CAC | GTC | ACG | GTG | CTG | CAG | TAC | TCC | TAC | ATG | GTG | ACC | 2352 |
|-----|-----|-----|-----|-----|-----|-----|-----|-----|-----|-----|-----|-----|-----|-----|-----|------|
| Gln | Asp | Ser | Ile | His | Val | Thr | Val | Leu | Gln | Tyr | Ser | Tyr | Met | Val | Thr |      |
|     | 770 |     |     |     |     | 775 |     |     |     |     | 780 |     |     |     |     |      |

| GTG | GAG | TAC | CCC | TTC | AGC | GAG | GCA | CAG | TCC | AAA | GGG | GAC | ATC | CTG | CAG | 2400 |
|-----|-----|-----|-----|-----|-----|-----|-----|-----|-----|-----|-----|-----|-----|-----|-----|------|
| Val | Glu | Tyr | Pro | Phe | Ser | Glu | Ala | Gln | Ser | Lys | Gly | Asp | Ile | Leu | Gln |      |
| 785 |     |     |     |     | 790 |     |     |     |     | 795 |     |     |     |     | 800 |      |

| CGG | GTG | CGA | GAG | ATC | CGC | TAC | CAG | GGC | GGC | AAC | AGG | ACC | AAC | ACT | GGG | 2448 |
|-----|-----|-----|-----|-----|-----|-----|-----|-----|-----|-----|-----|-----|-----|-----|-----|------|
| Arg | Val | Arg | Glu | Ile | Arg | Tyr | Gln | Gly | Gly | Asn | Arg | Thr | Asn | Thr | Gly |      |
|     |     |     |     | 805 |     |     |     |     | 810 |     |     |     |     | 815 |     |      |

| CTG | GCC | CTG | CGG | TAC | CTC | TCT | GAC | CAC | AGC | TTC | TTG | GTC | AGC | CAG | GGT | 2496 |
|-----|-----|-----|-----|-----|-----|-----|-----|-----|-----|-----|-----|-----|-----|-----|-----|------|
| Leu | Ala | Leu | Arg | Tyr | Leu | Ser | Asp | His | Ser | Phe | Leu | Val | Ser | Gln | Gly |      |
|     |     |     | 820 |     |     |     |     | 825 |     |     |     |     | 830 |     |     |      |

| GAC | CGG | GAG | CAG | GCG | CCC | AAC | CTG | GTC | TAC | ATG | GTC | ACC | GGA | AAT | CCT | 2544 |
|-----|-----|-----|-----|-----|-----|-----|-----|-----|-----|-----|-----|-----|-----|-----|-----|------|
| Asp | Arg | Glu | Gln | Ala | Pro | Asn | Leu | Val | Tyr | Met | Val | Thr | Gly | Asn | Pro |      |
|     |     | 835 |     |     |     |     | 840 |     |     |     |     | 845 |     |     |     |      |

| GCC | TCT | GAT | GAG | ATC | AAG | AGG | CTG | CCT | GGA | GAC | ATC | CAG | GTG | GTG | CCC | 2592 |
|-----|-----|-----|-----|-----|-----|-----|-----|-----|-----|-----|-----|-----|-----|-----|-----|------|
| Ala | Ser | Asp | Glu | Ile | Lys | Arg | Leu | Pro | Gly | Asp | Ile | Gln | Val | Val | Pro |      |
| 850 |     |     |     |     | 855 |     |     |     |     | 860 |     |     |     |     |     |      |

| ATT | GGA | GTG | GGC | CCT | AAT | GCC | AAC | GTG | CAG | GAG | CTG | GAG | AGG | ATT | GGC | 2640 |
|-----|-----|-----|-----|-----|-----|-----|-----|-----|-----|-----|-----|-----|-----|-----|-----|------|
| Ile | Gly | Val | Gly | Pro | Asn | Ala | Asn | Val | Gln | Glu | Leu | Glu | Arg | Ile | Gly |      |
| 865 |     |     |     |     | 870 |     |     |     |     | 875 |     |     |     |     | 880 |      |

| TGG | CCC | AAT | GCC | CCT | ATC | CTC | ATC | CAG | GAC | TTT | GAG | ACG | CTC | CCC | CGA | 2688 |
|-----|-----|-----|-----|-----|-----|-----|-----|-----|-----|-----|-----|-----|-----|-----|-----|------|
| Trp | Pro | Asn | Ala | Pro | Ile | Leu | Ile | Gln | Asp | Phe | Glu | Thr | Leu | Pro | Arg |      |
|     |     |     | 885 |     |     |     |     | 890 |     |     |     |     | 895 |     |     |      |

| GAG | GCT | CCT | GAC | CTG | GTG | CTG | CAG | AGG | TGC | TGC | TCC | GGA | GAG | GGG | CTG | 2736 |
|-----|-----|-----|-----|-----|-----|-----|-----|-----|-----|-----|-----|-----|-----|-----|-----|------|
| Glu | Ala | Pro | Asp | Leu | Val | Leu | Gln | Arg | Cys | Cys | Ser | Gly | Glu | Gly | Leu |      |
|     |     | 900 |     |     |     |     | 905 |     |     |     |     | 910 |     |     |     |      |

| GAC | ATC | CCC | ACC | CTC | TCC | CCA | GAC | CCT | GAC | TGC | AGC | CAG | CCC | CTG | GAC | 2784 |
|-----|-----|-----|-----|-----|-----|-----|-----|-----|-----|-----|-----|-----|-----|-----|-----|------|
| Asp | Ile | Pro | Thr | Leu | Ser | Pro | Asp | Pro | Asp | Cys | Ser | Gln | Pro | Leu | Asp |      |
|     | 915 |     |     |     |     | 920 |     |     |     |     | 925 |     |     |     |     |      |

| GTG | ATC | CTT | CTC | CTG | GAT | GGC | TCC | TCC | AGT | TTC | CCA | GCT | TCT | TAT | TTT | 2832 |
|-----|-----|-----|-----|-----|-----|-----|-----|-----|-----|-----|-----|-----|-----|-----|-----|------|
| Val | Ile | Leu | Leu | Leu | Asp | Gly | Ser | Ser | Ser | Phe | Pro | Ala | Ser | Tyr | Phe |      |

-continued

```
            930                 935                 940
GAT GAA ATG AAG AGT TTC GCC AAG GCT TTC ATT TCA AAA GCC AAT ATA      2880
Asp Glu Met Lys Ser Phe Ala Lys Ala Phe Ile Ser Lys Ala Asn Ile
945                 950                 955                 960

GGG CCT CGT CTC ACT CAG GTG TCA GTG CTG CAG TAT GGA AGC ATC ACC      2928
Gly Pro Arg Leu Thr Gln Val Ser Val Leu Gln Tyr Gly Ser Ile Thr
                965                 970                 975

ACC ATT GAC GTG CCA TGG AAC GTG GTC CCG GAG AAA GCC CAT TTG CTG      2976
Thr Ile Asp Val Pro Trp Asn Val Val Pro Glu Lys Ala His Leu Leu
            980                 985                 990

AGC CTT GTG GAC GTC ATG CAG CGG GAG GGA GGC CCC AGC CAA ATC GGG      3024
Ser Leu Val Asp Val Met Gln Arg Glu Gly Gly Pro Ser Gln Ile Gly
        995                 1000                1005

GAT GCC TTG GGC TTT GCT GTG CGA TAC TTG ACT TCA GAA ATG CAT GGT      3072
Asp Ala Leu Gly Phe Ala Val Arg Tyr Leu Thr Ser Glu Met His Gly
        1010                1015                1020

GCC AGG CCG GGA GCC TCA AAG GCG GTG GTC ATC CTG GTC ACG GAC GTC      3120
Ala Arg Pro Gly Ala Ser Lys Ala Val Val Ile Leu Val Thr Asp Val
1025                1030                1035                1040

TCT GTG GAT TCA GTG GAT GCA GCA GCT GAT GCC GCC AGG TCC AAC AGA      3168
Ser Val Asp Ser Val Asp Ala Ala Ala Asp Ala Ala Arg Ser Asn Arg
                1045                1050                1055

GTG ACA GTG TTC CCT ATT GGA ATT GGA GAT CGC TAC GAT GCA GCC CAG      3216
Val Thr Val Phe Pro Ile Gly Ile Gly Asp Arg Tyr Asp Ala Ala Gln
            1060                1065                1070

CTA CGG ATC TTG GCA GGC CCA GCA GGC GAC TCC AAC GTG GTG AAG CTC      3264
Leu Arg Ile Leu Ala Gly Pro Ala Gly Asp Ser Asn Val Val Lys Leu
        1075                1080                1085

CAG CGA ATC GAA GAC CTC CCT ACC ATG GTC ACC TTG GGC AAT TCC TTC      3312
Gln Arg Ile Glu Asp Leu Pro Thr Met Val Thr Leu Gly Asn Ser Phe
        1090                1095                1100

CTC CAC AAA CTG TGC TCT GGA TTT GTT AGG ATT TGC ATG GAT GAG GAT      3360
Leu His Lys Leu Cys Ser Gly Phe Val Arg Ile Cys Met Asp Glu Asp
1105                1110                1115                1120

GGG AAT GAG AAG AGG CCC GGG GAC GTC TGG ACC TTG CCA GAC CAG TGC      3408
Gly Asn Glu Lys Arg Pro Gly Asp Val Trp Thr Leu Pro Asp Gln Cys
                1125                1130                1135

CAC ACC GTG ACT TGC CAG CCA GAT GGC CAG ACC TTG CTG AAG AGT CAT      3456
His Thr Val Thr Cys Gln Pro Asp Gly Gln Thr Leu Leu Lys Ser His
            1140                1145                1150

CGG GTC AAC TGT GAC CGG GGG CTG AGG CCT TCG TGC CCT AAC AGC CAG      3504
Arg Val Asn Cys Asp Arg Gly Leu Arg Pro Ser Cys Pro Asn Ser Gln
        1155                1160                1165

TCC CCT GTT AAA GTG GAA GAG ACC TGT GGC TGC CGC TGG ACC TGC CCC      3552
Ser Pro Val Lys Val Glu Glu Thr Cys Gly Cys Arg Trp Thr Cys Pro
        1170                1175                1180

TGC GTG TGC ACA GGC AGC TCC ACT CGG CAC ATC GTG ACC TTT GAT GGG      3600
Cys Val Cys Thr Gly Ser Ser Thr Arg His Ile Val Thr Phe Asp Gly
1185                1190                1195                1200

CAG AAT TTC AAG CTG ACT GGC AGC TGT TCT TAT GTC CTA TTT CAA AAC      3648
Gln Asn Phe Lys Leu Thr Gly Ser Cys Ser Tyr Val Leu Phe Gln Asn
                1205                1210                1215

AAG GAG CAG GAC CTG GAG GTG ATT CTC CAT AAT GGT GCC TGC AGC CCT      3696
Lys Glu Gln Asp Leu Glu Val Ile Leu His Asn Gly Ala Cys Ser Pro
            1220                1225                1230

GGA GCA AGG CAG GGC TGC ATG AAA TCC ATC GAG GTG AAG CAC AGT GCC      3744
Gly Ala Arg Gln Gly Cys Met Lys Ser Ile Glu Val Lys His Ser Ala
        1235                1240                1245

CTC TCC GTC GAG CTG CAC AGT GAC ATG GAG GTG ACG GTG AAT GGG AGA      3792
Leu Ser Val Glu Leu His Ser Asp Met Glu Val Thr Val Asn Gly Arg
```

-continued

```
           1250                1255                 1260
CTG GTC TCT GTT CCT TAC GTG GGT GGG AAC ATG GAA GTC AAC GTT TAT      3840
Leu Val Ser Val Pro Tyr Val Gly Gly Asn Met Glu Val Asn Val Tyr
1265                1270                1275                1280

GGT GCC ATC ATG CAT GAG GTC AGA TTC AAT CAC CTT GGT CAC ATC TTC      3888
Gly Ala Ile Met His Glu Val Arg Phe Asn His Leu Gly His Ile Phe
            1285                1290                1295

ACA TTC ACT CCA CAA AAC AAT GAG TTC CAA CTG CAG CTC AGC CCC AAG      3936
Thr Phe Thr Pro Gln Asn Asn Glu Phe Gln Leu Gln Leu Ser Pro Lys
                1300                1305                1310

ACT TTT GCT TCA AAG ACG TAT GGT CTG TGT GGG ATC TGT GAT GAG AAC      3984
Thr Phe Ala Ser Lys Thr Tyr Gly Leu Cys Gly Ile Cys Asp Glu Asn
                    1315                1320                1325

GGA GCC AAT GAC TTC ATG CTG AGG GAT GGC ACA GTC ACC ACA GAC TGG      4032
Gly Ala Asn Asp Phe Met Leu Arg Asp Gly Thr Val Thr Thr Asp Trp
                        1330                1335                1340

AAA ACA CTT GTT CAG GAA TGG ACT GTG CAG CGG CCA GGA CAG ACG TGC      4080
Lys Thr Leu Val Gln Glu Trp Thr Val Gln Arg Pro Gly Gln Thr Cys
1345                1350                1355                1360

CAG CCC ATC CTG GAG GAG CAG TGT CTT GTC CCC GAC AGC TCC CAC TGC      4128
Gln Pro Ile Leu Glu Glu Gln Cys Leu Val Pro Asp Ser Ser His Cys
                1365                1370                1375

CAG GTC CTC CTC TTA CCA CTG TTT GCT GAA TGC CAC AAG GTC CTG GCT      4176
Gln Val Leu Leu Leu Pro Leu Phe Ala Glu Cys His Lys Val Leu Ala
                    1380                1385                1390

CCA GCC ACA TTC TAT GCC ATC TGC CAG CAG GAC AGT TCG CAC CAG GAG      4224
Pro Ala Thr Phe Tyr Ala Ile Cys Gln Gln Asp Ser Ser His Gln Glu
                        1395                1400                1405

CAA GTG TGT GAG GTG ATC GCC TCT TAT GCC CAC CTC TGT CGG ACC AAC      4272
Gln Val Cys Glu Val Ile Ala Ser Tyr Ala His Leu Cys Arg Thr Asn
         1410                1415                1420

GGG GTC TGC GTT GAC TGG AGG ACA CCT GAT TTC TGT GCT ATG TCA TGC      4320
Gly Val Cys Val Asp Trp Arg Thr Pro Asp Phe Cys Ala Met Ser Cys
1425                1430                1435                1440

CCA CCA TCT CTG GTC TAC AAC CAC TGT GAG CAT GGC TGT CCC CGG CAC      4368
Pro Pro Ser Leu Val Tyr Asn His Cys Glu His Gly Cys Pro Arg His
                1445                1450                1455

TGT GAT GGC AAC GTG AGC TCC TGT GGG GAC CAT CCC TCC GAA GGC TGT      4416
Cys Asp Gly Asn Val Ser Ser Cys Gly Asp His Pro Ser Glu Gly Cys
                    1460                1465                1470

TTC TGC CCT CCA GAT AAA GTC ATG TTG GAA GGC AGC TGT GTC CCT GAA      4464
Phe Cys Pro Pro Asp Lys Val Met Leu Glu Gly Ser Cys Val Pro Glu
                        1475                1480                1485

GAG GCC TGC ACT CAG TGC ATT GGT GAG GAT GGA GTC CAG CAC CAG TTC      4512
Glu Ala Cys Thr Gln Cys Ile Gly Glu Asp Gly Val Gln His Gln Phe
        1490                1495                1500

CTG GAA GCC TGG GTC CCG GAC CAC CAG CCC TGT CAG ATC TGC ACA TGC      4560
Leu Glu Ala Trp Val Pro Asp His Gln Pro Cys Gln Ile Cys Thr Cys
1505                1510                1515                1520

CTC AGC GGG CGG AAG GTC AAC TGC ACA ACG CAG CCC TGC CCC ACG GCC      4608
Leu Ser Gly Arg Lys Val Asn Cys Thr Thr Gln Pro Cys Pro Thr Ala
                1525                1530                1535

AAA GCT CCC ACG TGT GGC CTG TGT GAA GTA GCC CGC CTC CGC CAG AAT      4656
Lys Ala Pro Thr Cys Gly Leu Cys Glu Val Ala Arg Leu Arg Gln Asn
                    1540                1545                1550

GCA GAC CAG TGC TGC CCC GAG TAT GAG TGT GTG TGT GAC CCA GTG AGC      4704
Ala Asp Gln Cys Cys Pro Glu Tyr Glu Cys Val Cys Asp Pro Val Ser
                        1555                1560                1565

TGT GAC CTG CCC CCA GTG CCT CAC TGT GAA CGT GGC CTC CAG CCC ACA      4752
Cys Asp Leu Pro Pro Val Pro His Cys Glu Arg Gly Leu Gln Pro Thr
```

-continued

|  |  |  |
|---|---|---|
| 1570 | 1575 | 1580 |

| | |
|---|---|
| CTG ACC AAC CCT GGC GAG TGC AGA CCC AAC TTC ACC TGC GCC TGC AGG<br>Leu Thr Asn Pro Gly Glu Cys Arg Pro Asn Phe Thr Cys Ala Cys Arg<br>1585                       1590                     1595                     1600 | 4800 |
| AAG GAG GAG TGC AAA AGA GTG TCC CCA CCC TCC TGC CCC CCG CAC CGT<br>Lys Glu Glu Cys Lys Arg Val Ser Pro Pro Ser Cys Pro Pro His Arg<br>                     1605                     1610                     1615 | 4848 |
| TTG CCC ACC CTT CGG AAG ACC CAG TGC TGT GAT GAG TAT GAG TGT GCC<br>Leu Pro Thr Leu Arg Lys Thr Gln Cys Cys Asp Glu Tyr Glu Cys Ala<br>                     1620                     1625                     1630 | 4896 |
| TGC AAC TGT GTC AAC TCC ACA GTG AGC TGT CCC CTT GGG TAC TTG GCC<br>Cys Asn Cys Val Asn Ser Thr Val Ser Cys Pro Leu Gly Tyr Leu Ala<br>                 1635                     1640                     1645 | 4944 |
| TCA ACC GCC ACC AAT GAC TGT GGC TGT ACC ACA ACC ACC TGC CTT CCC<br>Ser Thr Ala Thr Asn Asp Cys Gly Cys Thr Thr Thr Thr Cys Leu Pro<br>                     1650                     1655                     1660 | 4992 |
| GAC AAG GTG TGT GTC CAC CGA AGC ACC ATC TAC CCT GTG GGC CAG TTC<br>Asp Lys Val Cys Val His Arg Ser Thr Ile Tyr Pro Val Gly Gln Phe<br>1665                       1670                     1675                     1680 | 5040 |
| TGG GAG GAG GGC TGC GAT GTG TGC ACC TGC ACC GAC ATG GAG GAT GCC<br>Trp Glu Glu Gly Cys Asp Val Cys Thr Cys Thr Asp Met Glu Asp Ala<br>                     1685                     1690                     1695 | 5088 |
| GTG ATG GGC CTC CGC GTG GCC CAG TGC TCC CAG AAG CCC TGT GAG GAC<br>Val Met Gly Leu Arg Val Ala Gln Cys Ser Gln Lys Pro Cys Glu Asp<br>                 1700                     1705                     1710 | 5136 |
| AGC TGT CGG TCG GGC TTC ACT TAC GTT CTG CAT GAA GGC GAG TGC TGT<br>Ser Cys Arg Ser Gly Phe Thr Tyr Val Leu His Glu Gly Glu Cys Cys<br>               1715                     1720                     1725 | 5184 |
| GGA AGG TGC CTG CCA TCT GCC TGT GAG GTG GTG ACT GGC TCA CCG CGG<br>Gly Arg Cys Leu Pro Ser Ala Cys Glu Val Val Thr Gly Ser Pro Arg<br>       1730                     1735                     1740 | 5232 |
| GGG GAC TCC CAG TCT TCC TGG AAG AGT GTC GGC TCC CAG TGG GCC TCC<br>Gly Asp Ser Gln Ser Ser Trp Lys Ser Val Gly Ser Gln Trp Ala Ser<br>1745                       1750                     1755                     1760 | 5280 |
| CCG GAG AAG CCC TGC CTC ATC AAT GAG TGT GTC CGA GTG AAG GAG GAG<br>Pro Glu Lys Pro Cys Leu Ile Asn Glu Cys Val Arg Val Lys Glu Glu<br>                     1765                     1770                     1775 | 5328 |
| GTC TTT ATA CAA CAA AGG AAC GTC TCC TGC CCC CAG CTG GAG GTC CCT<br>Val Phe Ile Gln Gln Arg Asn Val Ser Cys Pro Gln Leu Glu Val Pro<br>                 1780                     1785                     1790 | 5376 |
| GTC TGC CCC TCG GGC TTT CAG CTG AGC TGT AAG ACC TCA GCG TGC TGC<br>Val Cys Pro Ser Gly Phe Gln Leu Ser Cys Lys Thr Ser Ala Cys Cys<br>               1795                     1800                     1805 | 5424 |
| CCA AGC TGT CGC TGT GAG CGC ATG GAG GCC TGC ATG CTC AAT GGC ACT<br>Pro Ser Cys Arg Cys Glu Arg Met Glu Ala Cys Met Leu Asn Gly Thr<br>       1810                     1815                     1820 | 5472 |
| GTC ATT GGG CCC GGG AAG ACT GTG ATG ATC GAT GTG TGC ACG ACC TGC<br>Val Ile Gly Pro Gly Lys Thr Val Met Ile Asp Val Cys Thr Thr Cys<br>1825                       1830                     1835                     1840 | 5520 |
| CGC TGC ATG GTG CAG GTG GGG GTC ATC TCT GGA TTC AAG CTG GAG TGC<br>Arg Cys Met Val Gln Val Gly Val Ile Ser Gly Phe Lys Leu Glu Cys<br>                     1845                     1850                     1855 | 5568 |
| AGG AAG ACC ACC TGC AAC CCC TGC CCC CTG GGT TAC AAG GAA GAA AAT<br>Arg Lys Thr Thr Cys Asn Pro Cys Pro Leu Gly Tyr Lys Glu Glu Asn<br>                 1860                     1865                     1870 | 5616 |
| AAC ACA GGT GAA TGT TGT GGG AGA TGT TTG CCT ACG GCT TGC ACC ATT<br>Asn Thr Gly Glu Cys Cys Gly Arg Cys Leu Pro Thr Ala Cys Thr Ile<br>               1875                     1880                     1885 | 5664 |
| CAG CTA AGA GGA GGA CAG ATC ATG ACA CTG AAG CGT GAT GAG ACG CTC<br>Gln Leu Arg Gly Gly Gln Ile Met Thr Leu Lys Arg Asp Glu Thr Leu | 5712 |

```
                     1890                1895                1900
CAG GAT GGC TGT GAT ACT CAC TTC TGC AAG GTC AAT GAG AGA GGA GAG      5760
Gln Asp Gly Cys Asp Thr His Phe Cys Lys Val Asn Glu Arg Gly Glu
1905             1910                1915                1920

TAC TTC TGG GAG AAG AGG GTC ACA GGC TGC CCA CCC TTT GAT GAA CAC      5808
Tyr Phe Trp Glu Lys Arg Val Thr Gly Cys Pro Pro Phe Asp Glu His
            1925                1930                1935

AAG TGT CTG GCT GAG GGA GGT AAA ATT ATG AAA ATT CCA GGC ACC TGC      5856
Lys Cys Leu Ala Glu Gly Gly Lys Ile Met Lys Ile Pro Gly Thr Cys
        1940                1945                1950

TGT GAC ACA TGT GAG GAG CCT GAG TGC AAC GAC ATC ACT GCC AGG CTG      5904
Cys Asp Thr Cys Glu Glu Pro Glu Cys Asn Asp Ile Thr Ala Arg Leu
    1955                1960                1965

CAG TAT GTC AAG GTG GGA AGC TGT AAG TCT GAA GTA GAG GTG GAT ATC      5952
Gln Tyr Val Lys Val Gly Ser Cys Lys Ser Glu Val Glu Val Asp Ile
1970                1975                1980

CAC TAC TGC CAG GGC AAA TGT GCC AGC AAA GCC ATG TAC TCC ATT GAC      6000
His Tyr Cys Gln Gly Lys Cys Ala Ser Lys Ala Met Tyr Ser Ile Asp
1985             1990                1995                2000

ATG AAC GAT GTG CAG GAC CAG TGC TCC TGC TGT TCT CCG ACA CGG ACG      6048
Met Asn Asp Val Gln Asp Gln Cys Ser Cys Cys Ser Pro Thr Arg Thr
            2005                2010                2015

GAG CCC ATG CAG GTG GCC CTG CAC TGC ACC AAT GGC TCT GTT GTG TAC      6096
Glu Pro Met Gln Val Ala Leu His Cys Thr Asn Gly Ser Val Val Tyr
        2020                2025                2030

CAT GAG GTT CTC AAT GCC ATG GAG TGC AAA TGC TCC CCC AGG AAG TGC      6144
His Glu Val Leu Asn Ala Met Glu Cys Lys Cys Ser Pro Arg Lys Cys
    2035                2040                2045

AGC AAG TGA                                                          6153
Ser Lys *
    2050

(2) INFORMATION FOR SEQ ID NO:3:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:3:

TATGCTCACC TGTGAAGCAT GCCAGGAGCC GGGAGGCCTG GTGGTGCCTC CCACAGATGC      60

CCCGGTG                                                               67

(2) INFORMATION FOR SEQ ID NO:4:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:4:
```

```
ACGAGTGGAC ACTTCGTACG GTCCTCGGCC CTCCGGACCA CCACGGAGGG TGTCTACGGG         60
G                                                                        61
```

(2) INFORMATION FOR SEQ ID NO:5:

(i) SEQUENCE CHARACTERISTICS:
        (A) LENGTH: 226 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:5:

```
Leu His Asp Phe Tyr Cys Ser Arg Leu Leu Asp Leu Val Phe Leu Leu
 1               5                  10                  15

Asp Gly Ser Ser Arg Leu Ser Glu Ala Glu Phe Glu Val Leu Lys Ala
            20                  25                  30

Phe Val Val Asp Met Met Glu Arg Leu Arg Ile Ser Gln Leu Trp Val
        35                  40                  45

Arg Val Ala Val Val Glu Tyr His Asp Gly Ser His Ala Tyr Val Ile
50                  55                  60

Gly Leu Lys Asp Arg Lys Arg Pro Ser Glu Leu Arg Arg Ile Ala Ser
65                  70                  75                  80

Gln Val Lys Tyr Ala Gly Ser Gln Val Ala Ser Thr Ser Glu Val Leu
                85                  90                  95

Lys Tyr Thr Leu Phe Gln Ile Phe Ser Lys Ile Asp Arg Pro Glu Ala
            100                 105                 110

Ser Arg Ile Ala Leu Leu Leu Met Ala Ser Gln Glu Pro Gln Arg Met
        115                 120                 125

Ser Arg Asn Phe Val Arg Tyr Val Gln Gly Leu Lys Lys Lys Lys Val
    130                 135                 140

Ile Val Ile Pro Val Gly Ile Gly Pro His Ala Asn Leu Lys Gln Ile
145                 150                 155                 160

Arg Leu Ile Glu Lys Gln Ala Pro Glu Asn Lys Ala Phe Val Leu Ser
                165                 170                 175

Ser Val Asp Glu Leu Glu Gln Gln Arg Asp Glu Ile Val Ser Tyr Leu
            180                 185                 190

Cys Asp Leu Ala Pro Glu Ala Pro Pro Pro Thr Leu Pro Pro Asp Met
        195                 200                 205

Ala Gln Val Thr Val Gly Pro Gly Leu Leu Gly Val Ser Thr Leu Gly
    210                 215                 220

Pro Lys
225
```

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:6:

AAATCTGGCA GTGCTCAGGG TCACTGGGAT TCAAAGGTGA C                                41

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:7:

CCAGGACGAA CGCCACATCC AGAACCATGG AGTTCCTCTT                                  40

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:8:

TATGGAGGTG GCTGGCCGGC GTTTTGCC                                               28

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:9:

ACCTCCACCG ACCGGCCGCA AAACGGAGT                                              29

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:10:

TATGTTTGCC                                                                  10

(2) INFORMATION FOR SEQ ID NO:11:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:11:

ACAAACGGAG T                                                    11

(2) INFORMATION FOR SEQ ID NO:12:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:12:

CCGGGGCTCT TGGGGGTTTC GACCCTGGGG CCCAAGTAAG ATATCA          46

(2) INFORMATION FOR SEQ ID NO:13:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:13:

CCGAGAACCC CCAAAGCTGG GACCCCGGGT TCATTCTATA GTTCGA          46

(2) INFORMATION FOR SEQ ID NO:14:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:14:

CCGGGGCTCT TGGGGTTTCG ACCCTGGGGC CCAAGTAAGA TATCA           45

(2) INFORMATION FOR SEQ ID NO:15:

51

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:15:

```
CCGAGAACCC CAAAGCTGGG ACCCCGGGTT CATTCTATAG TTCGA              45
```

(2) INFORMATION FOR SEQ ID NO:16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:16:

```
TATGTTGCAC GATTTCTACT GCAGCAGGCT ACTGGACC                      38
```

(2) INFORMATION FOR SEQ ID NO:17:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:17:

```
ACAACGTGCT AAAGATGACG TCGTCCGATG ACCTGGA                       37
```

(2) INFORMATION FOR SEQ ID NO:18:

(i) SEQUENCE CHARACTERISTICS:
        (A) LENGTH: 681 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (ix) FEATURE:
        (A) NAME/KEY: CDS
        (B) LOCATION: 1..681

(xi) SEQUENCE DESCRIPTION: SEQ ID NO:18:

```
ATG TTG CAC GAT TTC TAC TGC AGC AGG CTA CTG GAC CTG GTC TTC CTG     48
Met Leu His Asp Phe Tyr Cys Ser Arg Leu Leu Asp Leu Val Phe Leu
  1               5                  10                  15

CTG GAT GGC TCC TCC AGG CTG TCC GAG GCT GAG TTT GAA GTG CTG AAG     96
```

```
Leu Asp Gly Ser Ser Arg Leu Ser Glu Ala Glu Phe Glu Val Leu Lys
        20                  25                  30

GCC TTT GTG GTG GAC ATG ATG GAG CGG CTG CGC ATC TCC CAG AAG TGG      144
Ala Phe Val Val Asp Met Met Glu Arg Leu Arg Ile Ser Gln Lys Trp
        35                  40                  45

GTC CGC GTG GCC GTG GTG GAG TAC CAC GAC GGC TCC CAC GCC TAC ATC      192
Val Arg Val Ala Val Val Glu Tyr His Asp Gly Ser His Ala Tyr Ile
 50                  55                  60

GGG CTC AAG GAC CGG AAG CGA CCA TCA GAG CTG CGG CGC ATT GCC AGC      240
Gly Leu Lys Asp Arg Lys Arg Pro Ser Glu Leu Arg Arg Ile Ala Ser
 65                  70                  75                  80

CAG GTG AAG TAT GCG GGC AGC CAG GTG GCC TCC ACC AGC GAG GTC TTG      288
Gln Val Lys Tyr Ala Gly Ser Gln Val Ala Ser Thr Ser Glu Val Leu
            85                  90                  95

AAA TAC ACA CTG TTC CAA ATC TTC AGC AAG ATC GAC CGC CCT GAA GCC      336
Lys Tyr Thr Leu Phe Gln Ile Phe Ser Lys Ile Asp Arg Pro Glu Ala
                100                 105                 110

TCC CGC ATC GCC CTG CTC CTG ATG GCC AGC CAG GAG CCC CAA CGG ATG      384
Ser Arg Ile Ala Leu Leu Leu Met Ala Ser Gln Glu Pro Gln Arg Met
            115                 120                 125

TCC CGG AAC TTT GTC CGC TAC GTC CAG GGC CTG AAG AAG AAG AAG GTC      432
Ser Arg Asn Phe Val Arg Tyr Val Gln Gly Leu Lys Lys Lys Lys Val
        130                 135                 140

ATT GTG ATC CCG GTG GGC ATT GGG CCC CAT GCC AAC CTC AAG CAG ATC      480
Ile Val Ile Pro Val Gly Ile Gly Pro His Ala Asn Leu Lys Gln Ile
145                 150                 155                 160

CGC CTC ATC GAG AAG CAG GCC CCT GAG AAC AAG GCC TTC GTG CTG AGC      528
Arg Leu Ile Glu Lys Gln Ala Pro Glu Asn Lys Ala Phe Val Leu Ser
                165                 170                 175

AGT GTG GAT GAG CTG GAG CAG CAA AGG GAC GAG ATC GTT AGC TAC CTC      576
Ser Val Asp Glu Leu Glu Gln Gln Arg Asp Glu Ile Val Ser Tyr Leu
            180                 185                 190

TGT GAC CTT GCC CCT GAA GCC CCT CCT CCT ACT CTG CCC CCC GAC ATG      624
Cys Asp Leu Ala Pro Glu Ala Pro Pro Pro Thr Leu Pro Pro Asp Met
        195                 200                 205

GCA CAA GTC ACT GTG GGC CCG GGG CTC TTG GGG GTT TCG ACC CTG GGG      672
Ala Gln Val Thr Val Gly Pro Gly Leu Leu Gly Val Ser Thr Leu Gly
210                 215                 220

CCC AAG TAA                                                          681
Pro Lys *
225

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:19:

TATGCTGGAC C                                                          11

(2) INFORMATION FOR SEQ ID NO:20:

(i) SEQUENCE CHARACTERISTICS:
        (A) LENGTH: 10 base pairs
        (B) TYPE: nucleic acid
```

(C) STRANDEDNESS: single
           (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:20:

ACGACCTGGA                                                                                10

(2) INFORMATION FOR SEQ ID NO:21:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:21:

AGCCCCACCA CTCTGTATGT GGAGGACATC TCGGAACCGC CGTTGCACGA TTTCTACTGC      60
A                                                                     61

(2) INFORMATION FOR SEQ ID NO:22:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:22:

CCACTCGGGG TGGTGAGACA TACACCTCCT GTAGAGCCTT GGCGGCAACG TGCTAAAGAT      60
G                                                                     61

(2) INFORMATION FOR SEQ ID NO:23:

(i) SEQUENCE CHARACTERISTICS:
        (A) LENGTH: 225 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

Leu His Asp Phe Tyr Cys Ser Arg Leu Leu Asp Leu Val Phe Leu Leu
1               5                   10                  15

Asp Gly Ser Ser Arg Leu Ser Glu Ala Glu Phe Glu Val Leu Lys Ala
            20                  25                  30

Phe Val Val Asp Met Met Glu Arg Leu Arg Ile Ser Gln Lys Trp Val
        35                  40                  45

```
Arg Val Ala Val Val Glu Tyr His Asp Gly Ser His Ala Tyr Ile Gly
            50                  55                  60

Leu Lys Asp Arg Lys Arg Pro Ser Glu Leu Arg Arg Ile Ala Ser Gln
 65                  70                  75                  80

Val Lys Tyr Ala Gly Ser Gln Val Ala Ser Thr Ser Glu Val Leu Lys
                    85                  90                  95

Tyr Thr Leu Phe Gln Ile Phe Ser Lys Ile Asp Arg Pro Glu Ala Ser
                100                 105                 110

Arg Ile Ala Leu Leu Met Ala Ser Gln Glu Pro Gln Arg Met Ser
                115                 120                 125

Arg Asn Phe Val Arg Tyr Val Gln Gly Leu Lys Lys Lys Val Ile
130                 135                 140

Val Ile Pro Val Gly Ile Gly Pro His Ala Asn Leu Lys Gln Ile Arg
145                 150                 155                 160

Leu Ile Glu Lys Gln Ala Pro Glu Asn Lys Ala Phe Val Leu Ser Ser
                165                 170                 175

Val Asp Glu Leu Glu Gln Gln Arg Asp Glu Ile Val Ser Tyr Leu Cys
                180                 185                 190

Asp Leu Ala Pro Glu Ala Pro Pro Thr Leu Pro Pro Asp Met Ala
                195                 200                 205

Gln Val Thr Val Gly Pro Gly Leu Leu Gly Val Ser Thr Leu Gly Pro
210                 215                 220

Lys
225

(2) INFORMATION FOR SEQ ID NO:24:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

Cys Ser Arg Leu Leu Asp Leu Val Phe Leu Leu Asp Gly Ser Ser Arg
 1               5                  10                  15

Leu Ser Glu Ala Glu Phe Glu Val Leu Lys Ala Phe Val Val Asp Met
                20                  25                  30

Met Glu Arg Leu Arg Ile Ser Gln Lys Trp Val Arg Val Ala Val Val
                35                  40                  45

Glu Tyr His Asp Gly Ser His Ala Tyr Ile Gly Leu Lys Asp Arg Lys
 50                  55                  60

Arg Pro Ser Glu Leu Arg Arg Ile Ala Ser Gln Val Lys Tyr Ala Gly
 65                  70                  75                  80

Ser Gln Val Ala Ser Thr Ser Glu Val Leu Lys Tyr Thr Leu Phe Gln
                85                  90                  95

Ile Phe Ser Lys Ile Asp Arg Pro Glu Ala Ser Arg Ile Ala Leu Leu
                100                 105                 110

Leu Met Ala Ser Gln Glu Pro Gln Arg Met Ser Arg Asn Phe Val Arg
                115                 120                 125

Tyr Val Gln Gly Leu Lys Lys Lys Val Ile Val Ile Pro Val Gly
130                 135                 140
```

```
Ile Gly Pro His Ala Asn Leu Lys Gln Ile Arg Leu Ile Glu Lys Gln
145                 150                 155                 160

Ala Pro Glu Asn Lys Ala Phe Val Leu Ser Ser Val Asp Glu Leu Glu
                165                 170                 175

Gln Gln Arg Asp Glu Ile Val Ser Tyr Leu Cys Asp Leu Ala Pro Glu
            180                 185                 190

Ala Pro Pro Pro Thr Leu Pro Pro Asp Met Ala Gln Val Thr Val Gly
        195                 200                 205

Pro Gly Leu Leu Gly Val Ser Thr Leu Gly Pro Lys
    210                 215                 220
```